US006576221B1

(12) United States Patent
Kresse et al.

(10) Patent No.: US 6,576,221 B1
(45) Date of Patent: Jun. 10, 2003

(54) IRON-CONTAINING NANOPARTICLES WITH DOUBLE COATING AND THEIR USE IN DIAGNOSIS AND THERAPY

(75) Inventors: Mayk Kresse, Berlin (DE); Detlev Pfefferer, Berlin (DE); Rüdiger Lawaczek, Berlin (DE); Susanne Wagner, Berlin (DE); Wolfgang Ebert, Berlin (DE); Volker Elste, Berlin (DE); Wolfhard Semmler, Glienicke (DE); Matthias Taupitz, Berlin (DE); Josef Gaida, Berlin (DE); Anja Herrmann, Berlin (DE); Monika Jukl, Berlin (DE); Udo Swiderski, Berlin (DE)

(73) Assignees: Institut fur Diagnostikforschung GmbH, Berlin (DE); Der Freien Universitat Berline, Berlin (DE)

( * ) Notice: Subject to any disclaimer, the term of this patent is extended or adjusted under 35 U.S.C. 154(b) by 0 days.

(21) Appl. No.: 09/451,822

(22) Filed: Nov. 30, 1999

Related U.S. Application Data

(62) Division of application No. 08/776,958, filed as application No. PCT/DE95/00924 on Jul. 10, 1995, now Pat. No. 6,048,515.

(30) Foreign Application Priority Data

Aug. 4, 1994 (DE) .......................................... 44 28 851

(51) Int. Cl.⁷ .............................................. A61B 5/055
(52) U.S. Cl. .................. 424/9.322; 424/9.32; 424/9.3; 424/9.1; 424/1.11; 424/646; 514/6; 514/54; 514/59; 514/60
(58) Field of Search .............................. 424/1.11, 1.65, 424/9.1, 9.3, 9.32, 9.321, 9.322, 9.4, 9.5, 9.6, 9.7, 9.8, 9.323, 646; 514/53, 54, 55, 56, 57, 58, 59, 60, 61

(56) References Cited

U.S. PATENT DOCUMENTS

| 5,174,987 A | * | 12/1992 | Takaichi et al. | ............. 424/9.1 |
| 5,219,552 A | * | 6/1993 | Dietlin et al. | ................ 424/9.1 |
| 5,492,814 A | * | 2/1996 | Weissleder | .................. 435/725 |
| 6,048,515 A | * | 4/2000 | Kresse et al. | ............ 424/9.322 |

FOREIGN PATENT DOCUMENTS

DE 4301871 A1 * 7/1994

* cited by examiner

Primary Examiner—Dameron L. Jones
(74) Attorney, Agent, or Firm—Millen, White, Zelano & Branigan, P.C.

(57) ABSTRACT

The present invention relates to iron-containing nanoparticles having a modular structure, their production, and their use for diagnostic and therapeutic purposes.

The nanoparticles according to the invention are characterized in that they consist of an iron-containing core, a primary coat (synthesis polymer), and a secondary coat (targeting polymer) and, optionally, of pharmaceutic adjuvants, pharmaceuticals, and/or adsorption mediators/enhancers.

16 Claims, 35 Drawing Sheets

General overview of the process to produce the nanoparticles according to the invention.

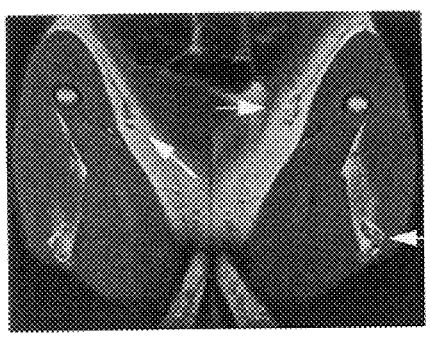
Ln. inguinales
Ln. popliteales
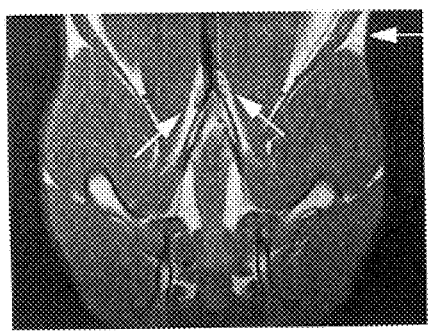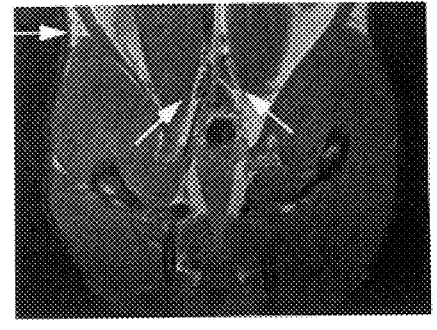
Ln. subiliacales
Ln. iliacales
prae                                              24 h p.i.
FIG. 8

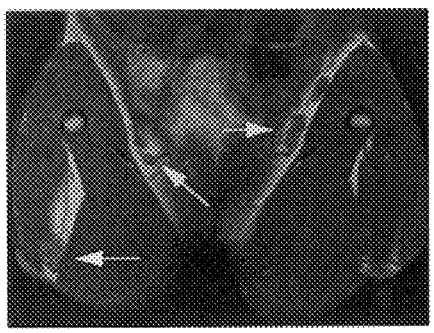 
Ln. inguinales
Ln. popliteales
 
Ln. subiliacales
Ln. iliacales
prae
24 h p.i.
FIG. 9

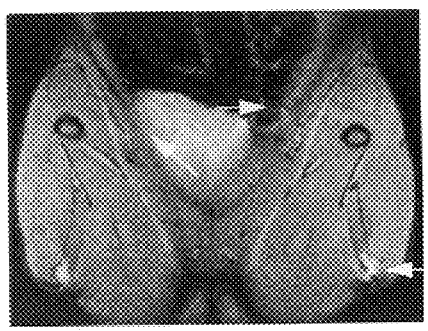 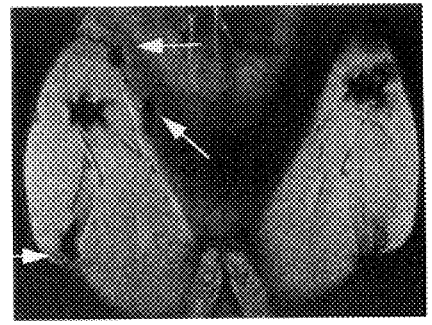
Ln. inguinales
Ln. popliteales
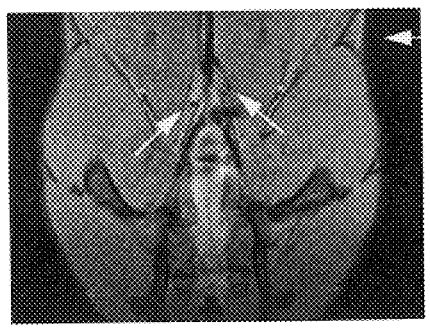 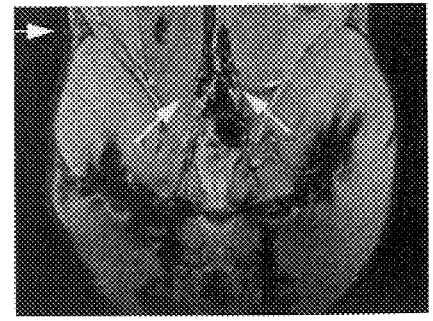
Ln. subiliacales
Ln. iliacales
prae          24 h p.i.
FIG. 11 unspecific nanoparticles (C2)     specific nanoparticles (D2)

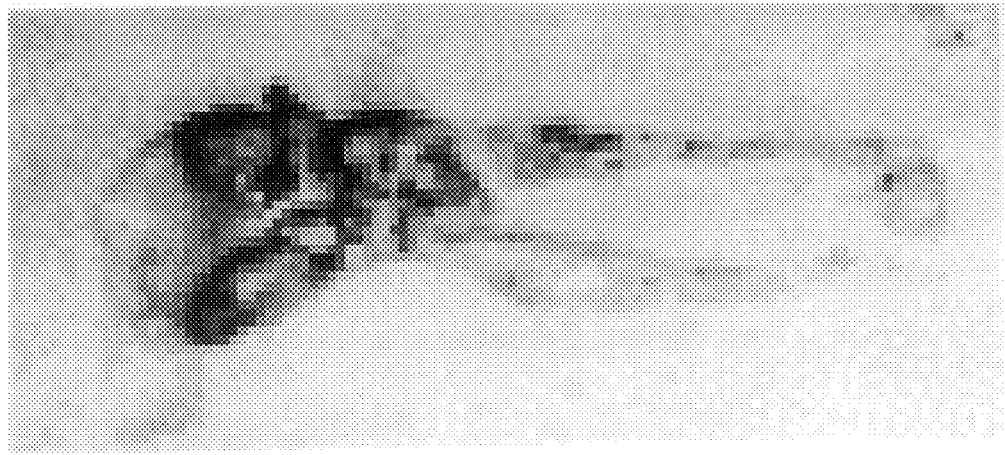
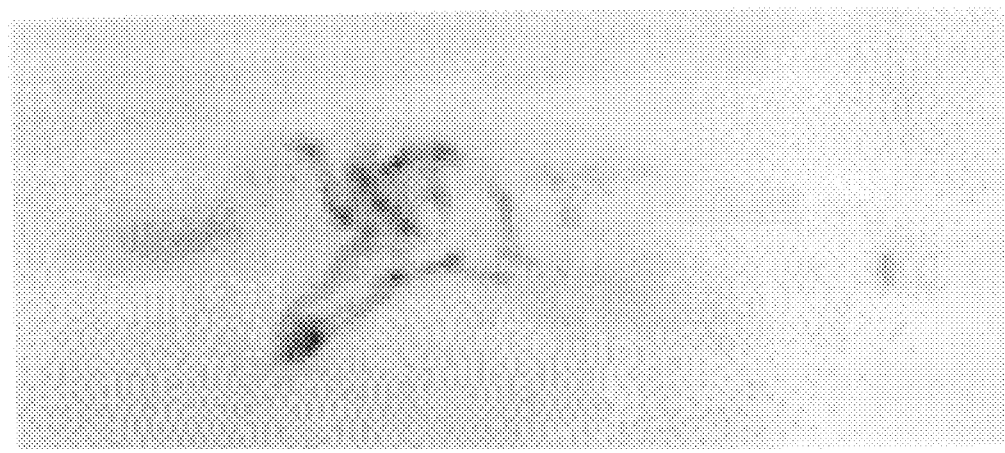
FIG. 32

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      Artificially synthesized short peptide.

<400> SEQUENCE: 1

Arg Arg Thr Val Lys His His Val Asn
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:
      Artificially synthesized short peptide.

<400> SEQUENCE: 2

Arg Arg Ser Arg His His
 1               5

<210> SEQ ID NO 3
```

```
-continued

<211> LENGTH: 6
<212> TYPE: PRT
<213> ORGANISM: Artificial Sequence
<220> FEATURE:
<223> OTHER INFORMATION: Description of Artificial Sequence:
      Artificially synthesized short peptide.

<400> SEQUENCE: 3

Arg Ser Lys Arg Gly Arg
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:
      Artificially synthesized short peptide.

<400> SEQUENCE: 4

Cys His Leu Asp Ile Ile Trp
 1               5
```

IRON-CONTAINING NANOPARTICLES WITH DOUBLE COATING AND THEIR USE IN DIAGNOSIS AND THERAPY

CROSS-REFERENCE TO RELATED APPLICATION

This is a division of application Ser. No. 08/776,958, filed Feb. 4, 1997 now U.S. Pat. No. 6,048,515, which is a 371 of PCT/DE95/00924, filed Jul. 10, 1995.

FIELD OF THE INVENTION

This invention relates to iron-containing nanoparticles having a modular structure, their production, and their use for diagnostic and therapeutic purposes.

BACKGROUND OF THE INVENTION

Substances that show maximum magnetization even at a low field strength (high saturation magnetization) but no remanence after the external magnetic field is switched off, as the thermal energy counteracts the permanent alignment of spontaneously magnetized Weiss' domains, are called superparamagnetic substances. This category includes iron-containing crystals that are developed as parenteral MR contrast materials. A characteristic property of said substances is their strong impact on proton relaxation times and thus their great efficacy as a contrast medium in this diagnostic procedure. In medical diagnostics, the focus of examining superparamagnetic substances was placed on iron oxides having a "magnetite-like" crystal structure of the kind found in magnetite or maghemite (spinel, inverse spinel).

The superparamagnetic iron oxides to be used as MR contrast materials have similar properties in that they strongly influence proton relaxation in their close range (high relaxivity), and that they are particles having a "magnetite-like" crystal structure.

A great number of methods have been described for the production of iron-containing crystals (iron oxides) having superparamagnetic properties. These methods can be classified according to various aspects. Two basic methods to produce superparamagnetic crystals can be distinguished between: sintering at high temperatures and subsequent mechanical comminution, or wet chemical synthesis in solution. Up to now, only those particles that were produced by wet synthesis have been investigated for medical applications, while the sintering method has been described for the manufacture of iron oxides for technological (sound carriers, paint pigments and toners) and biotechnological applications such as the magnetic separating method [Schostek S, Beer A; DE 3,729,697 A1; Borelli N F, Luderer A A, Panzarino J N; U.S. Pat. No. 4,323,056; Osamu I, Takeshi H, Toshihiro M et al.; JP 60,260,463 A2]. Wet chemical synthesis can be subcategorized. There is "two-pot synthesis", which first produces an iron-containing core (iron oxide) to which a stabilizer is added to ensure the physical and galenic quality. The production of an iron core using ion exchangers is a variant of "two-pot synthesis". With "single-pot synthesis", the iron oxides are produced in the presence of the stabilizer which already coats the cores during nucleation and precipitation of the iron salts, thereby preventing aggregation and sedimentation of the nanocrystals.

Apart from distinguishing "two-pot" and "single-pot" methods according to the processes involved, there is another distinction based on the type of solvent used, namely between aqueous (Hasegawa M, Hokukoku S; U.S. Pat. No. 4,101,435; Fuji Rebio K. K.; JP 59,195,1611 and non-aqueous methods [Porath J, Mats L; EP 179,039 A2; Shigeo A, Mikio K, Toshikatzu M; J. Mater. Chem. 2(3); 277–280; 1992; Norio H, Saturo O; JP 05,026,879 A2].

Particles that were produced in a "two-pot" process using non-aqueous solvents are mainly used in engineering. Magnetic iron oxides for use as contrast materials in human diagnostics require an aqueous dispersing agent for medical and toxicological reasons. A special place is held in this categorization by those particles that were produced in a non-aqueous solvent but can be stable when dispersed in an aqueous medium after production. Such particles are currently used, in general, in ex-vivo diagnostics, e.g. in magnetic separation engineering [Chagnon M S, Groman E V, Josephson L, et al.; U.S. Pat. No. 4,554,088] but have also been proposed for in-vivo diagnostics [Pilgrimm H; U.S. Pat. No. 5,160,725].

Particles produced in a "two-pot" process were mainly used in the early experimental examinations up to the mid-1980s, while today's tests involving iron oxides are described only for materials produced by a "single-pot synthesis". The "single-pot" method has been generally accepted for the production of superparamagnetic iron-containing oxides for human diagnostic applications as they are superior to those produced by a "two-pot" method from the point of view of their physical and chemical quality as well as pharmaceutical/galenic stability.

Pharmaceutically stable suspensions/solutions of particles produced in aqueous media according to the "single-pot method" may be subdivided into iron oxides of different sizes. Biotechnological applications were proposed for particles in the micrometer range [Schröder U, Mosbach K; WO 83/01738 or Schröder U; WO 83/03426], and their application even claimed in in-vivo diagnostics and therapy [Widder K J, Senyei A E; U.S. Pat. No. 4,247,406 or Jacobsen T. Klaveness J; WO 85/04330]. For approaches in medical diagnostics, however, particles in the nanometer range are the main ones described today. This range may also be subdivided according to the preferred use into "large" (overall diameter ca. >50 nm) and "small" (overall diameter ca. <50 nm) particles. MR diagnostics of the liver and the spleen is the main field of application, as particles of this size are rapidly and nearly completely taken up by the macrophages of these organs [Kresse M, Pfefferer D, Lawaczeck R; EP 516,252 A2 or Groman E V, Josephson L; U.S. Pat. No. 4,770,183]. Furthermore, proposals were made for uses as reinforcing substances in clinical hyperthermia [Hasegawa M, Hirose K, Hokukoku S, et al.; WO 92/22586 A1 and Gordon R T; U.S. Pat. No. 4,731,239].

Nearly all the particles currently proposed for medical applications are iron oxides that were produced in the presence of dextran as the stabilizing substance [Bacic G, Niesmann M R, Magin R L et al.; SMRM—Book of abstracts 328; 1987; Ohgushi M, Nagayama K, Wada A et al.; J. Magnetic Resonance 29; 599–601; 1978; Pouliquen D, Le Jeune J J, Perdrisot R et al.; Magnetic Resonance Imaging 9; 275–283; 1991 or Ferrucci J T and Stark D D; AJR 155; 311–325; 1990] but the use of other polysaccharides has also been described, for example, for arabinogalactan [Josephson L, Groman E V, Menz E et al; Magnetic Resonance Imaging 8; 616–637; 1990], starch [Fahlvik A K, Holtz E, Schröder U et al; Invest. Radiol. 25; 793–797; 1990], glycosaminoglycans [Pfefferer D, Schimpfky C, Lawaczeck R; SMRM—Book of abstracts 773; 1993], or proteins [Widder D J, Grief W L, Widder K J et al.; AJR 148; 399–404; 1987].

The exact conditions for synthesis such as those involving iron salts, temperature, coating polymer (stabilizer), titration rate, alkali selection, purification, etc. affect the chemical and physical properties of the products and, therefore, their pharmaceutical and galenic quality as well as medical value.

An important step in the development leading to an effective use in specific applications was made by Weissleder and Papisov [Weissleder R; Papisov M I; Reviews of Magnetic Resonance in Medicine 4; 1–20; 1992] who were able to show that the "targetability" of the magnetic iron oxides is reciprocally proportional to particle size. A problem in this respect is the fact that efficacy (MR effect) decreases with smaller particle sizes. The production of particularly small magnetic iron oxides without any fractionating stages has recently been described [Hasegawa M, Ito Y, Yamada H, et al.; JP 4,227,792]. Experiments on "functional imaging" were reported for particularly small particles called MIONs. The dextran coating of said particles (magnetic labels) were oxidized using periodate and then coupled with specific molecules (antimyosin; polyclonal antibody) [Weissleder R, Lee A S, Khaw B A et al.; Radiology 182; 381–385; 1992, or Weissleder R, Lee A S, Fishman A et al.; Radiology 181; 245–249; 1991].

A special course is taken by Menz et al. [Menz ET, Rothenberg J M, Groman E V, et al.; WO 90/01295] who coat their large nanometer particles with polymers (arabinogalactan) having physiological effector cells and claim a specific uptake mechanism via receptor-mediated endocytosis just like Gordon [Gordon R T; U.S. Pat. No. 4,735,796], who oxidizes dextran-stabilized particles using periodate and then couples them with transferrin by reductive amination.

Production of "large" superparamagnetic iron oxides for use as contrast materials in MR diagnostics of the liver and the spleen is the state of the art, and the diagnostic benefit of said materials has been proved. Some of these iron oxides are being developed for clinical purposes (AMI-25; Advanced Magnetics Inc.; Cambridge; Mass.; USA; Phase III/IV and SHU 555A; Schering AG Berlin; Germany; Phase II). The importance of the hydrodynamic diameters of iron oxides for specific (extrahepatic) approaches such as MR lymphography or MR angiography are known and are being examined. The half-life in the blood should increase with smaller diameters for particles that are otherwise identical. Synthesis variants for producing small iron oxides are known from the literature.

An essential problem encountered in the development of specific contrast materials based on superparamagnetic iron oxides is that it has been impossible so far to improve targeting properties, i.e. accumulation and distribution in the target tissue, without having to accept simultaneous drawbacks in physical and chemical parameters, as the stabilizers that are most suitable for producing iron-containing cores are very limited for targeting purposes. In addition, reaction conditions during synthesis (acid to alkaline pH, temperatures, redox reactions involving the iron salts) reduce the choice of potential stabilizers in that whole groups of important and highly specific molecules (proteins, peptides, oligonucleotides, but also most oligo- and polysaccharides) cannot be used as stabilizers in the manufacturing phase whenever said substances have to retain any targeting properties (bioactivity) after the synthesis.

It is known from the (chemically) "insensitive" polymers used up to now, mainly from dextran, that various non-controllable reactions occur in synthesis conditions, for example, depolymerization in the acidic range of pH values (low-molecular weight dextran, for example, is yielded in technical quality by acid hydrolysis) and various other reactions that may result in complete destruction of the (glyco-) polymer in the alkaline range (precipitation step). It may be assumed, taking into account sucro-/glycochemistry and the reaction conditions required, that state-of-the-art "dextran magnetites" are not dextran magnetites at all because dextran was used for stabilizing, but no dextran remained after synthesis. If this is viewed from the pharmaceutical and approval point of view, this means that an essential ingredient—as the stabilizer forms the coat and thus determines biological behavior to a major extent—is unknown or undeclared.

Another practical problem resulting therefrom is that surface properties cannot be optimized during future development if the surface itself is unknown.

A specific application such as MR lymphography, which has been studied the best, can be used to show that size optimization of state-of-the-art particles using dextran as the stabilizer (nothing has been published so far about other polymers for the production of small iron oxides) does, on the one hand, improve applicability, since it facilitates considerable particle accumulation in the lymphatic tissue, but that its distribution throughout lymphatic nodes, on the other, is not sufficiently homogeneous for clinical application [Taupitz, M et al.; SMRM—Book of abstracts 500; New York; USA; 1993]. This strong but inhomogeneous accumulation makes additional improvement by repeated optimization of the hydrodynamic diameters not very likely.

The small size of the target organ is an important problem for developing specific diagnostic substances. The overall weight of the lymphatic nodes, for example, makes up less than 1 percent of the body weight. Diagnostic substances must therefore have substantial accumulation potential in the target tissue (specificity) and facilitate a strong contrast-enhancing effect at low concentrations.

As superparamagnetic iron oxides currently represent the group of substances having the strongest contrast in MR, these particles appear particularly appropriate for specific applications. The crystal core of the iron oxides, which causes the particular character of said substances, is a problem, however, as particle size has an essential influence on biological behavior. Smaller particle sizes improve targetability, but the efficiency of the contrast material diminishes due to the interdependency of particle size and magnetic moment, so that a compromise must be found between the (physical) contrastive effect and (biological) targetability. As a rule, the iron-containing core should be required to be as large as possible to achieve high efficacy, whereas the overall diameter should be kept small.

The problem dealt with by the invention is to provide iron-containing nanoparticles that match physical and biological requirements with a specific nanoparticle in optimum fashion.

SUMMARY OF THE INVENTION

Surprisingly, it was found that the targeting capabilities of the nanoparticles according to the invention are superior to those of state-of-the-art iron oxide particles. Contrast materials and/or therapeutic substances/supporting systems of unprecedented "targetability" can be produced by combining physical quality with improved targeting capabilities of the nanoparticles.

The nanoparticles are produced from individual blocks (modular design), which ensures maximum flexibility when the iron-containing cores (physical effect; contrast)are combined with the target component (biological behavior). This modular structure is advantageous in that it allows "just-in-time" assembly of the complete nanoparticle from a component that can be stored (iron-containing core) and targeting molecules that may be highly sensitive. This similarity with cold kits known from clinical radiopharmacy also facilitates, for example, the use of individual patients' serum components as target molecules (e.g. autologous antibodies).

The nanoparticles of the invention can also be detected visually due to their intense coloring, which is desirable, for example, when they are used as a visual labeling substance in surgery.

Furthermore, the nanoparticles described are also suitable for therapeutic uses, for example, for magnetic targeting using external magnets above a target volume in conjunction with a magnetically linked release of active substances. Nanoparticles may, for example, accumulate in tumors, and thus be used as specific reinforcing agents in local hyperthermia.

The nanoparticles of the invention consist of an iron-containing core, a primary coat (synthesis polymer) which is responsible for optimal sized nanoparticles, and a secondary coat (targeting polymer) and, optionally, pharmaceutical adjuvants, pharmaceuticals and/or adsorption mediators/enhancers.

The iron-containing core can have the form of a particle, a colloid or a crystal. The nanoparticles contain synthesis polymer from the production of the core which coats the core as a primary coat and is required during production for control of the physical and/or pharmaceutical/galenic quality. The ratio of synthesis polymer to iron is then adjusted to a desired value by means of a desorption process. A targeting polymer is adsorbed for use in specific diagnostics that represents the surface of the nanoparticles and envelops the basic structural unit of the core and primary coat. Adsorption mediators/enhancers may be present between the primary and the secondary coat for improved adsorption. Other ingredients of the nanoparticles may be pharmaceutical adjuvants or drugs.

FIG. 1 shows a sectional view of the structure of a nanoparticle according to the invention.

The hydrodynamic diameter of said basic structural unit (iron-containing core plus primary coat) in solution is smaller than 100 nm, preferably smaller than 50 nm, and not more than five times the diameter of the iron-containing core.

The nanoparticles according to the invention are further characterized in that they are available in the form of stable colloidal sols, which is preferred, but they can also be formulated as lyophilized powders which can easily be put into solution again using solvents common in medicine (electrolyte solution, plasma expander, glucose solution, physiological saline, etc.), or in that the basic structural unit as well as targeting component and optional adjuvants are separate solutions or lyophilizates that can be mixed at any desired point in time to obtain the solution for administration.

The iron-containing core has a magnetic moment greater than that of iron(II) or iron(III) ions. The iron-containing core, due to its magnetic properties, facilitates the contrast-enhancing effect when the substance is used as contrast material in MR tomography. It should be superparamagnetic, or at least contain superparamagnetic portions, to achieve optimum contrast rendering. This means that the core should either be a crystal or a polyatomic complex ("particle") as this type of magnetism only occurs in solid matter.

The iron-containing core of the invention may consist of, or contain, magnetite or maghemite.

Up to 25 percent of the iron by weight contained in the core may be substituted by other metallic ions.

Said non-iron metallic ions are paramagnetic, diamagnetic, or a mixture of both.

The nanoparticles according to the invention are further characterized in that the iron-containing core comprises a diameter determined by way of electron microscopy that is smaller than 30 nm, preferably smaller than 15 nm, contains a minimum of 50 metallic atoms with a particle size distribution in which at least 90% of the iron-containing cores are in the range of 0.7×average to 1.3×average.

The nanoparticles contain a quantity of synthesis polymer between 0.01 to 1 times the total weight of metallic ions present. The preferred quantity is between 0.25 and 0.75 times that weight.

A monomeric or polymeric substance, or a mixture of these substances or derivatives, or derivatives comprising functional groups, or derivatives that were additionally substituted and have a molecular weight smaller than 100,000 Da are used as synthesis polymer. Preferred substances have molecular weights smaller than 10,000 or 5000 Da.

A dextran derivative or a mixture of dextran and/or dextran derivatives, are particularly preferred for use as synthesis polymers.

The synthesis polymer may contain in its molecule one or several acid groups, or several functional groups, which preferably contain N, S, P, or O atoms.

The substances or mixtures of substances used as targeting and synthesis polymers may be the same or different, with the targeting polymer having retained its physiological state as it was not exposed to synthesis and the side reactions of the synthesis polymer during synthesis.

The parent substance of the iron-containing core and primary coat determines the physical quality of the nanoparticle, while the targeting polymer determines the biological behavior of said nanoparticles.

The weight of targeting polymer contained in the nanoparticle is 0.5 times to 50 times, preferably 1 to 25 times the weight of the metallic ions present.

The nanoparticles according to the invention may contain adsorption mediators/enhancers in a quantity smaller than, or equal to, the total weight of metallic ions contained. These adsorption mediators/enhancers reinforce or enable the adsorption of targeting polymer by the basic structural unit consisting of the iron-containing core/(remaining) synthesis polymer.

Preferred adsorption mediators/enhancers and peptides having the following structures: Arg-Arg-Thr-Val-Lys-His-His-Val-Asn (SEQ ID NO:1), Arg-Arg-Ser-Arg-His-His (SEQ ID NO:2), or Arg-Ser-Lys-Arg-Gly-Arg (SEQ ID NO:3), or partial structures thereof.

The hydrodynamic diameter, including all the components of the nanoparticles, is not more than ten times the diameter of the iron-containing core and not more than 20% greater than the diameter of the basic structural unit.

The nanoparticles according to the invention are composed of individual modules such as a basic structural unit, a targeting polymer, a pharmacon and an adsorption mediator that can be combined at any time.

The nanoparticle preparations are low-viscosity, aqueous colloidal solutions or suspensions of stabilized iron-containing particles in the nanometer range. The nanoparticle solutions do not contain any larger aggregates and can be administered intravenously, which meets with particle size requirements for parenterals found in international pharmacopoeia.

In general, the basic structural unit can be sterilized by heat treatment. The "sterilization" process of the final nanoparticles is dependent on the sensitivity of the secondary coat, but sterile, aseptic manufacture is guaranteed in any case. Sterilization by filtration is always feasible due to the small size of the particles. Another way to guarantee a practically sterile solution for administration is the option that combines a sensitive targeting polymer with the sterilizable basic structural unit shortly before use.

The nanoparticles are well-tolerated and comprise a very favorable margin of safety between the diagnostic and lethal dose when used, for example, as MR contrast media. The diagnostic dose, depending on the specific application, is between 5 $\mu$mol and 200 $\mu$mol (iron) per kilogram of body weight, while the approximate lethal dose is between 20 mmol and 50 mmol/kg body weight (in mice). The substances are completely biodegradable. The iron-containing core is dissolved, and the iron is incorporated into the physiological iron pool. The molecules used as synthesis and targeting polymers can in general be catabolized to decomposable elementary units (sugars, amino acids).

The nanoparticle solutions are very stable; there is no detectable change in physical parameters (particle size, magnetic properties) after their preparation. The solutions can be stored for an extended period of time when they are produced in sterile conditions; for example, no instabilities such as aggregation or sedimentation were visible within 12 months.

The solutions or suspensions have a reddish-brown to black coloring due to the intense color of the iron-containing crystals. This characteristic coloring can be utilized for visual detection purposes so that said substances can be used for labeling in surgical medicine. The nanoparticles are superparamagnetic or contain superparamagnetic portions when used as contrast media in MR tomography. The particles show high saturation magnetization even at low field strengths and have no remanence after the external magnet has been switched off.

The nanoparticles are formulated as solutions (suspensions) and can be applied without further preparation. As the nanoparticle solutions are compatible with common medical solvents such as physiological saline, electrolyte solution or glucose solution, particles can be diluted as may be desired and injected or infused for specific applications.

Lyophilizates are an alternative to formulating a solution from the point of view of storage. Either the basic structural unit is lyophilized and later resuspended in the dissolved targeting polymer, or the basic structural unit and nanoparticle are lyophilized after adsorption and dissolved again before use in physiological saline or sterile water for injection. Another way of keeping a stock of said substances is to store the basic structural unit and the targeting polymer in separate solutions and mix them before use.

The particular or colloidal iron-containing cores are produced from unimolecularly dissolved iron precursors by changing, following single-pot synthesis, their pH value and causing them to precipitate in the presence of a stabilizer substance (synthesis polymer). The synthesis polymer separates the crystal cores during production and may therefore be used to control particle size. The synthesis polymer is responsible for the physical and pharmaceutical/galenic properties not only of the crystal core but of the whole nanoparticle. The synthesis polymer facilitates a stable solution (suspension) as the cores are separated to such an extent that aggregation cannot occur (steric stabilization).

When the iron-containing core particles are obtained, the synthesis polymer is adjusted by desorption to a given ratio of synthesis polymer to iron. The solution (suspension) of the iron core and the synthesis polymer residue that envelops and stabilizes the iron-containing core as a primary coat represent the basic structural unit of the modular system. This basic structural unit is characterized by high physical and galenic quality.

A second important component is the targeting polymer that is adsorbed by the basic structural unit after synthesis and envelops the core and primary coat as a secondary coat. The secondary coat is the surface of the nanoparticles and determines in-vivo behavior. The basic structural unit and targeting polymer can be mixed at any time, which also allows "just-in-time" production.

The adsorption process between synthesis polymer residue and targeting polymer may be improved or facilitated by an intermediate step: addition of adsorption mediators/enhancers. An adsorption mediator/enhancer can also be added to a mixture with the targeting polymer. Pharmaceutical adjuvants or drugs may be added at any time in a similar way.

The special advantages of the invention are obvious as the production method according to the invention makes it possible for the first time to meet both physical and biological requirements for a specific nanoparticle in an optimum way.

The synthesis polymer having the most appropriate physical properties may be chosen for synthesis because of the modular structure of the particle, i.e. separate production of the basic structural unit (iron-containing core+primary coat) and targeting polymer (secondary coat), without any limitation by the desired biological targetability of the nanoparticles; so, for the first time, no compromises must be made regarding the physical and pharmaceutical quality of the nanoparticles and their desired biological effect. The targeting polymer is not exposed to the destructive synthesis conditions. This allows the use of many substances for targeting that are ruled out as a primary coat. Similarly, there is no need for post-synthetic chemical reactions that would require adequate reaction conditions and reduce the integrity of the ligand; for example, there are no redox reactions that involve proteins containing disulfide bridges as in periodate oxidation and subsequent reductive amination: biological activity is maintained.

Another essential advantage is the fact that there is no need for Purification of the basic structural unit/targeting polymer, as no reaction solutions such as periodate have to be separated. The method allows instant production, including "just-in-time" production of nanoparticles immediately before use, which may be required or desirable, for example, for "individual" contrast media (e.g. autologous antibodies) or if the targeting polymer remains stable in solution only for a short time.

The method according to the invention has advantages for further optimization as the "surface" of the nanoparticles can be modified/optimized separately, and an analysis can be carried out using advanced methods of analysis such as NMR or IR spectroscopy. These methods cannot be applied if particular cores are present.

As the surface is produced in a defined way and can be adequately analyzed, systematic optimization of surface properties becomes possible whereas with each state-of-the-art production method, in which a particle is treated as a whole, the surface is unknown and can only be optimized by trial and error.

The nanoparticles are thus produced in several steps. The iron-containing core is generally synthesized by means of a "single-pot" process, i.e. in the presence of a stabilizer (synthesis polymer). The stabilizer (synthesis polymer) is dissolved in water and mixed with the unimolecular iron compounds. The iron salts are converted into the preferred oxides by increasing the pH value. Alternatively, the stabilizer solution can be alkalized and then mixed with the iron salts. The mixture is heated under reflux and neutralized, or vice versa. The crude substance is purified and the surplus or not firmly adsorbed/bound synthesis polymer is adjusted to an exact iron-to-stabilizer weight ratio by means of a desorption process. This purified and desorbed base substance consisting of an iron oxide core and (residual) synthesis polymer represents the basic structural unit of the (modular structured) nanoparticles. Sterilization by heat may follow as an option. The selected targeting polymer is adsorbed, either when required or for maintenance "in stock", by the basic structural unit, optionally with intermediate adsorption or co-adsorption of an adsorption mediator/enhancer. Other ingredients such as pharmaceutical adjuvants or drugs may be added optionally. An overview of the general production method is given in FIG. 2.

Note that synthesis always takes place in the presence of a stabilizer according to the "single-pot" process for the following description of the iron-containing core.

Stoichiometric quantities of iron(II) and iron(III) salts are mixed as precursors to produce iron-containing cores. The quality of the resulting crystals is influenced by the salts used; according to the literature, salts of hydrochloric acid, i.e. ferrous and ferric chlorides, are mainly used. But in general, all salts of strong acids including sulfates and nitrates may be used. When these salts are used it is difficult to ensure exact stoichiometry because iron(II) salts are highly sensitive to oxidation. It is advantageous here to use more complex salts such as Mohr's salt, which is less sensitive to oxidation.

Surprisingly, it turned out that organic salts are superior to inorganic salts as the organic anions act as stabilizers or auxiliary stabilizers. Iron(II) gluconate or Iron(III) citrate proved to be particularly suitable; but other organic anions such as fumarates, tartrates, lactates, or salicylates may be used as well.

A synthesis variant that relies only on iron(III) salt facilitates production without having to resort to highly oxidation-sensitive iron(II) salts and reduces the number of "foreign ions". This synthesis variant starts only from iron (III) salt from which iron(II) salt is generated in situ during reaction only by means of a calculated amount of a reducing agent. Although, in general, it is possible to use all reducing agents that reduce iron(III) with stoichiometrical accuracy, hydroxylamine is preferred, as the reacted hydroxylamine quantitatively converts into laughing-gas and thus is easily, and completely, removed from the reaction mixture.

$$4Fe^{3+}+2NH_2OH \rightarrow 4Fe^{2+}+N_2O+4H^++H_2O$$

A disadvantage of previously described methods becomes obvious if one takes a closer look at the chemistry of iron salts. It is the goal of the precipitation step to convert iron(II) and iron(III) in stoichiometric composition into a crystal having a defined structure. The respective oxides are formed by increasing the pH value. But if one considers that the iron(III) ions [$pK_L$ Fe(OH)3 ca. 37[1]][1] form sparingly soluble hydroxides at a pH value of about 2 while the iron(II) ions start to precipitate as hydroxides [$pK_L$ Fe(OH)$_2$ ca. 13.5] at pH 8, it becomes apparent that direct formation of the desired crystals seems hardly possible and that the reaction path must include a successive reaction of the hydroxides. It is possible, however, to shift the precipitation points of the iron compounds in relation to each other using appropriate complexing agents, thus achieving simultaneous precipitation and insertion at the various lattice sites in the iron oxide crystal. The precipitation points of the iron compounds used can be controlled over a wide range by selecting an appropriate complexing agent.

[1]$pK_L$ values are dependent on concentration. The data refer to a solution of $10^{-2}$ mol/l.

Apart from "classical" substances according to Table 1, the above organic anions may be used as complexing agents. Complex salts, organic anion salts and inorganic salts of the iron(II) and iron(III) ions may be combined in whatever way may be desired.

TABLE 1

Selection of complexing and chelating agents for shifting precipitation points when pH values are increased during magnetite synthesis

| Complexing agents (chelate) | iron II logK1* | iron III logK1* |
|---|---|---|
| CDTA trans-1,2-diamino-cyclohexan-N,N,N',N'-tetraacetic acid | 16.27 | 28.05 |
| EDTA ethylenediamine-tetraacetic acid | 14.33 | 25.10 |
| EGTA ethyleneglycol-O,O'-bis-(2-aminoethyl)-N,N,N',N'-tetraacetic acid | 11.92 | 20.50 |
| DTPA diethylenetriamine-pentaacetic acid | 16.50 | 28.60 |
| HEDTA N-(2-hydroxyethyl)-ethylenediamine-N,N',N'-triacetic acid | 12.20 | 19.80 |
| NTA nitrilotriacetic acid | 8.84 | 15.87 |
| TTHA triethylentetramin-N,N,N',N'',N''',N'''-hexaacetic acid | 17.10 | 26.80 |

*$K_1$ is the absolute stability constant and is independent of pH. It refers to the deprotonated form of the chelating agent: $K_1 = [ML]/[M] \cdot [L]$, where [ML], [M] and [L] are the concentrations of chelate, metallic ion and chelating agent (ligand).

The chelates listed in Table 1 are only supposed to demonstrate the range of suitable compounds and should not be construed as restricted to these substances only.

In a synthesis variant, iron(II) hydroxide and iron(III) hydroxide are first produced separately. Surprisingly, the iron oxide crystals are successfully produced by combining the separately prepared hydroxide solutions; transformation and crystallization are accelerated when the combined solutions are heated.

Precipitation is an important step in the production of the iron-containing cores. The particular iron compounds are formed from low-molecular weight iron compounds by increasing the pH value; colloidal iron hydroxides may be an optional intermediate product during particle formation. Any substance that can raise the pH value of the dissolved acidic iron precursors is suitable for increasing the pH. Apart from soda lye, pH values are preferably increased using ammonia, either gaseous or as a salt, or alkaline amines and volatile buffers. It turned out, surprisingly, that the base used for precipitation affects the overall properties in such a way that "biological" effects become visible as, for example, differences in the distribution of the particles throughout body organs.

The concentration of the alkaline substance should be between 0.1 to 10 N; concentrated solutions of about 1 to 4 N are preferred because particles having small core sizes preferably form when the pH increase takes place at a faster rate. Bases are added within 30 minutes, preferably within 30 seconds.

The iron compounds are precipitated onto the particles at a temperature range of 0–120° C., with 50–80° C. being the preferred range. As a general rule, temperature can be low when the iron oxide is formed directly, and should be high when formation involves hydroxides as an intermediate step. The product is neutralized after precipitation and, subsequently, the crude substance is refluxed, in particular, when hydroxides form as intermediate products; heating time should be between 0 minutes and 24 hours, preferably between 30 minutes and one hour. Neutralisation and refluxing may be carried out in reverse order.

Self-coloring of the substance is desirable for its use as a contrast medium (optical labeling substance) for visual detection in surgery.

The application for MR tomography requires high effectiveness that is determined by the magnetic properties of the nanoparticles. The iron oxides magnetite and maghemite seem to be particularly appropriate when the nanoparticles are used as an MR contrast material, as they show high saturation magnetization at the field strengths applied in clinical MR tomography. The special magnetic properties are determined by the crystal structure of the particular iron cores. But, surprisingly, foreign ions can be inserted in this crystal core, with a magnetite-like crystal structure still being arrived at. This doping with non-ferruginous metallic ions may generally be carried out in two ways. On the one hand, iron(II) and/or iron(III) ions are replaced at their lattice sites by other paramagnetic metallic ions while, on the other, diamagnetic ions can be used for substitution. It should be kept in mind for better comprehension that magnetization in the magnetite crystal stems from iron(II) ions only, as iron(III) ions occupy parallel/antiparallel lattice positions so that their individual magnetic vectors are neutralized. The net amount of magnetization can be increased by using ions that have a higher magnetic moment than iron, or by changing the equilibrium of parallel/antiparallel lattice site occupation by iron(III) ions using para- or diamagnetic ions. If substitution involves paramagnetic metals with high magnetic moments such as gadolinium, an increase may be yielded that equals the difference in magnetic moments when compared to the iron replaced. If iron(III) is substituted by diamagnetic metals, the no longer compensated moment of an iron(III) ion can contribute to the overall moment. As a variant, dia- and paramagnetic ions can be inserted in the magnetite-like crystal lattice together. Doping with non-iron ions is carried out by partial substitution of the low-molecular iron-containing parent compounds during synthesis.

The general method for producing the iron-containing cores is to synthesize a magnetite-like crystal lattice. Iron(II) and iron(III) ions are used for this purpose at ratios ranging from 1:1 to 1:20. Synthesis is achieved most easily using an exactly stoichiometric ratio of 1:2. Iron(II)-to-iron(III) ratios can be maintained during synthesis by means of a reducing agent. Iron(II) and iron(III) ions can be replaced by other metallic ions up to the equivalent of 25% of the total iron content (weight). Besides paramagnetic ions such as gadolinium or manganese, diamagnetic ions such as lithium, magnesium, or calcium, or a mixture of para- and diamagnetic ions, may be used. Magnetite or magnetite-like structures are the preferred crystal structures. This so-called spinel or inverse-spinel crystal can be formed as a secondary product, for example, if the production first yields hydroxides, or the magnetite crystal is converted into other crystals, as, for example, from magnetite into maghemite by oxidation. The special quality of the nanoparticles used as contrast materials for MRT requires superparamagnetic properties. Superparamagnetism only occurs in solid matter; thus another requirement is that the crystals have the properties of solids, i.e. that they are particular crystals or, at least, polyatomic clusters. Minimum iron content should be 50 iron atoms (or metal atoms) per crystal. The size of the iron-containing cores can be controlled by variation during synthesis throughout a wide range (from 1 to about 30 nm), but synthesis of smaller cores with diameters of less than 15 nm and a minimum of 90% of particles within a range of $0.7 \times mean < mean < 1.3 \times mean$ (mean being the mean diameter determined using electron microscopy) is preferred.

It is one of the specific advantages of the production method according to the invention that it offers great flexibility in the selection of synthesis polymers; the term "polymer" is not to be taken literally, as both low-molecular weight substances and mixtures of low- and polymolecular weight substances can be used for producing iron-containing cores. Particularly preferred is the use of low-molecular and polymolecular substances that contain negative charge carriers in their molecule. The following are preferred: carboxylates or analogues, phosphates (or other P-containing groups) and sulfates (or other S-containing groups). These derivatives may simply carry one single functional group or contain several functional groups. The theory upon which this is based assumes that affinity to the surface of the iron-containing core is due to interaction of the positive iron oxide surface and the negative charge in the synthesis polymer. If the synthesis polymer contains several of these groups, interaction is particularly distinct ("multi-side attachment"). As there is a great number of suitable substances, they cannot all be listed here. Some classes of substances that are specially suitable for stabilization during synthesis are: Low-molecular weight substances such as carboxypolyalcohols, polycarboxypolyalcohols, polycarboxyalcohols, carboxyalcohols, alcohols, monosugars, oligosugars, and synthesis polymers such as polyethylene glycol, polypropylene glycol and mixtures (block and copolymers), polyacrylic acid, polyvinyl alcohol, polylactic acid (polylactide and polylactide glycide), and natural or, specifically, partially synthetic or chemically and/or enzymatically modified natural polymers such as dextrans and its derivatives, arabinic acid, glycosaminoglycan and synthetic analogues, starch and its derivatives as well as gelatin derivatives.

It is particularly preferable to use low-molecular weight derivatives of dextran that contain negative charge carriers. (Mono)carboxydextran can serve as an example here; its manufacture is described, for example, in Bremner et al. [Bremner, I.; Cox, JSG; Moss, GF; Carbohydrate Research 11; 77–84; 1969], and another preferred example is the use of polycarboxydextran, which is produced by an ether bond between 6-bromohexanoic acid and the hydroxy groups of the dextran. [Noguchi, A.; Takahashi, T; Yamaguchi, T.; Kitamura, Y.; Takakura, T.; Hashida, M.; Sezaki, H.; Bioconjugate chemistry 3; 132–137; 1992]. The poly-carboxydextran is able, due to its many negative charges, to interact with the surface of the iron oxide through "multi-side attachment".

The quantity of synthesis polymer required for stabilization during production is 0.5 to 20 times the total weight of the metallic ions contained in the batch; its overall percentage in the reaction mixture is selected to ensure that the viscosity still allows thorough mixing of the batch when polymeric synthesis polymers are used (<50% g/v). The weight of the synthesis polymer used should preferably exceed the total weight of the metallic ions by 3 to 15 times.

After the crude substance has been produced, the synthesis polymer component in the batch is reduced by means of a desorption process. Chromatographic procedures, a magnetic separation method, dialysis, centrifugation or ultrafiltration, or other appropriate methods can be employed for desorption. Desorption can be carried out at increased temperatures in conjunction with one of the desorption processes. Another way to influence the extent of desorption is the use of desorbing substances such as buffer solutions or tensides.

After desorbing the crude substance, a stable, physically optimal solution/suspension is obtained which represents the basic structural unit for the manufacture of specific nanoparticles. The basic structural unit consists of an iron-containing core and the (residual) synthesis polymer. The quantity of residual synthesis polymer is between 0.01 and 1, depending on the ratio adjusted by the desorption process. The range between 0.25 and 0.75 is preferred because the best compromise between stability and adsorbability of the basic structural unit is achieved in this range. The overall size (hydrodynamic diameter) of the basic structural unit varies depending on the size of the iron-containing core and the synthesis polymer used and is thus smaller than 100 nm, preferably smaller than 50 nm. It is preferred to produce basic structural units having an overall diameter no greater than five times the core diameter.

The basic structural unit and targeting polymer are combined to yield the final nanoparticle. The adsorbed targeting polymer forms a secondary coat around the synthesis polymer/iron-containing core unit, thus being the surface of the system which mainly determines, besides the particular nature of the particle, the in-vivo behavior. The special advantage of this production method is that virtually every substance that can be adsorbed by the basic structural unit can be used to control the biological behavior of the nanoparticle. The targeting polymers are not exposed to the strains of synthesis, so that sensitive substances and substances that could not be used up to now can function as supporting molecules for controlling biological behavior.

The following are examples of suitable targeting polymers:

Natural oligo- and polysaccharides such as dextran with molecular weights of less than 100,000 Da, mixtures of various dextrans, dextrans of different origin, specially purified dextran (FP=free pyrogene quality), fucoidan, arabinogalactan, chondroitin and its sulfates, dermatan, heparin, heparitin, hyaluronic acid, keratan, polygalacturonic acid, polyglucuronic acid, polymannuronic acid, inulin, polylactose, polylactosamine, polyinosinic acid, polysucrose, amylose, amylopectin, glycogen, glucan, nigeran, pullulan, irisin, asparagosin, sinistrin, tricitin, critesin, graminin, sitosin, lichenin, isolichenan, galactan, galactocaolose, luteose, mannans, mannocarolose, pustulan, laminarin, xanthene, xylan and copolymers, araboxylan, arabinogalactan, araban, laevans (fructosans), teichinic acid, blood group polysaccharides, guaran, carubin, alfalfa, glucomannans, galactoglucomannans, phosphomannans, fucans, pectins, cyclo-dextrins, alginlc acid, tragacanth and other gums, chitin, chitosan, agar, furcellaran, carrageen, cellulose, celluronic acid or arabinic acid. Additionally, chemically and/or enzymatically produced derivatives of the listed substances and the low-molecular weight decomposition products of polymolecuiar compounds are claimed. Optionally, these substances or derivatives can be substituted by any other substance. Polyamino- and pseudopolyamino acids are suited as well.

Synthetic oligo- and polymers such as polyethylene glycol, polypropylene glycol, polyoxyethylene ether, polyanethol sulfonic acid, polyethylene imine, polymaleimide, polyvinyl alcohol, polyvinyl chloride, polyvinyl acetate, polyvinyl pyrrolidone, polyvinyl sulfate, polyacrylic acid, polymethacrylic acid, polylactide, polylactide glycide.

Monosugars to oligosugars and related substances such as aldo- and ketotrioses to aldo- and ketoheptoses, ketooctoses and ketononoses, anhydrosugars, monocarboxylic acids and derivatives containing 5 or 6 carbon atoms in their main chain, cyclites, amino and diamino sugars, desoxy sugars, aminodesoxy sugars and amino sugar carboxylic acids, aminocyclites, phosphor-containing derivatives of mono- to oligomers.

Monomer or oligomercarbohydrates or derivatives having antitumoral properties (higher plants, fungi, lichens and bacteria) such as lipopolysaccharides, or containing one or more of the following structures: $\beta$-2,6-fructan, $\beta$-1,3-glucan, mannoglucan, mannan, glucomannan, $\beta$-1,3/1,6-glucans, $\beta$-1,6-glucan, $\beta$-1,3/1,4-glucan, arabinoxylan, hemicellulose, $\beta$-1,4-xylan, arabinoglucan, arabinogalactan, arabinofucoglucan, $\alpha$-1,6/1,3-glucan, $\alpha$-1,5-arabinan, $\alpha$-1,6-glucan, $\beta$-2,1/2,6-fructan, $\beta$-2,1-fructan.

An important prerequisite for the effect of antitumoral polysaccharides is solubility in water, which is guaranteed with the $\beta$-1,3/1,6-glucans by branches at position 6. Solubility of polysaccharides that are insoluble in water can be improved by introducing hydrophile and well-hydrated groups. Amino, acetyl, carboxymethyl or sulfate groups may be used, among others such as methyl and ethyl, as substituents.

Tensides and surface-active substances such as niotensides, alkyl glucosides, glucamides, alkyl maltosides, mono- and polydisperse polyoxyethylene, quaternary ammonium salts, bile acids, alkyl sulfates, betaines, CHAP derivatives.

As an example, and to illustrate the great number of control options and thus the advantages of the modular system, molecules for controlling in-vivo behavior (specificity) may also be cell fragments, cells, bacteria fragments, substances from the large group of lectins, hormones and mediator substances, proteins and neoproteins, peptides and polypeptides, antibodies, antibody fragments or the "molecular recognition units", of integrins (ELAM, LECAM, VCAM, etc.) or receptor-specific substances (e.g. Lewis-X, Sialyl-Lewis-X, etc.), or the great number of blood/plasma/serum components and opsonins, the group of oligonucleotides and synthetic oligonucleotides, DNA and RNA or their derivatives or fragments or analogues (PNA) and homologues, from the group of lipopolysaccharides, lipoproteins, glycerol esters, cholesterols and esters, or metabolites and antimetabolites, cytostatic agents, medical substances, conjugates of medical substances, chemotherapeutical substances and cytostatic agents.

Chemical and/or enzymatically produced derivatives or decomposition products may be used as targeting polymers in addilcn to, or instead of, the above substances.

The derivatives or "native" targeting polymers may include additional functional groups. These functional groups can be located at one or both ends or at any other position in the basic targeting molecule. The functional groups can be the same, or combinations of different groups. Preferred among the derivatives themselves as well as the functional groups are those which contain N, S, O or P atoms, acid or analogues, hydroxy, ether or ester groups.

The exact composition of the nanoparticles depends on the requirements of the indication. Targeting polymers can be individual substances or any combination of targeting polymers such as synthetic and non-synthetic, low molecular and polymolecular, derivatized and non-derivatized.

A special variant of manufacture is the use of the same polymer as the synthesis and targeting polymer. This means that the targeting polymer is the same as the polymer used for synthesis, as the synthesis polymer that is present after synthesis will, as has been described, no longer be identical with the polymer used for synthesis. The targeting polymer is the same as the stated synthesis polymer, but it was not exposed to the crucial drastic conditions that occur during synthesis and has therefore maintained its "physiological" state.

Targeting polymer quantities in the final nanoparticle solution can be varied throughout a wide range. In general, they may vary between 0.5 to 50 times the overall weight of the metallic ions contained; however, 1 to about 25 times that weight is the preferred quantity. Adsorption mediators/ enhancers are all substances that improve or facilitate adsorption of the targeting polymer or the mixture of target polymers by the surface of the iron-containing core or iron-containing core and primary coat. In general, adsorption mediators/enhancers must have bifunctional properties: while one molecular part has an affinity for the basic structural unit, another molecular part, which may, however, be identical with that first functional part, causes affinity for the targeting molecule. Suitable substances are substances having two functional groups, or a hydrophobic and a hydrophilic molecular part. Peptides that have an affinity for the iron core, or for the iron core plus primary coat, are preferred adsorption mediators/enhancers. Such peptides can be selected from peptide libraries using advanced biochemical methods.

Preferred are peptides containing the Arg-Arg-Thr-Val-Lys-His-His-Val-Asn (SEQ ID NO:1) or Arg-Arg-Ser-Arg-His-His (SEQ ID NO:2) or Arg-Ser-Lys-Arg-Gly-Arg (SEQ ID NO:3) sequence or parts thereof in their molecule (three-letter code of amino acids;

Another advantage of using peptides as adsorption mediators/enhancers is that the molecular part which is not required for affinity can be optionally coupled covalently with the targeting polymer or polymers, which makes affinity to the targeting polymer an optional property. The quantity of adsorption mediator required depends on the substances used (intensity of adsorption mediation) and on the properties of the targeting polymer or polymers; the total amount is less than, or equal to, the overall weight of metallic ions contained in the core.

Pharmaceutical additives or adjuvants that may be contained in nanoparticle solutions can be divided into five classes according to their function: preserving agents, pH stabilizers, antioxidants, isotonizing additives, peptisators and solutizers. Other adjuvants can be medically tolerable solvents such as sugar solutions, plasma expanders, electrolyte solutions, physiological saline or water for injection, as well as parenterally applicable oily "solvents".

Examples of pharmaceuticals or drugs that may be contained in nanoparticle solutions can be grouped as follows: antiallergic agents, antianaphylactic or prophylactic agents, vasodilators or vasoconstrictors, substances that influence the blood flow, substances that influence nanoparticle metabolism, substances that influence the pharmacokinetics of the nanoparticles, substances that change the iron balance, substances from the group of enzyme inductors and inhibitors, or general mediators and antimediators. Among the medical substances for therapeutic uses the main interest is in those coming from the groups of cytostatic agents, chemotherapeutic agents, hormones and antidiabetic agents.

Pharmaceuticals and drugs can be added to the nanoparticle solutions as optional components or can be coupled to the targeting polymers; the conjugate of polymer and medical substance is then used as the targeting polymer.

The "physiological" distribution of the nanoparticles cannot only be changed by pharmaceuticals that influence "physiological" factors such as the blood flow, lymph flow and lymph production or the like; in-vivo distribution can also be changed by simple physiotherapeutic measures. Movement that can be "applied" directly by taking a walk or practising on an ergometer and, as its counterpart, immobility, as found, for example, with indoor patients and/or application under anaesthesia and the like, which result in a completely different distribution behavior and pattern. Furthermore, heat input should be mentioned here, which can be accomplished by simple use of infrared light, or whole-body or partial baths. A hyperthermia facility as used in many clinics for purposeful heat input for adjuvant tumor treatment is particularly preferred. intentional local heating improves "selectivity" in accompanying physiotherapeutic measures.

The great flexibility of the modular production design allows a free combination of targeting polymer(s), adsorption mediator(s), pharmaceutical adjuvants and pharmaceuticals as well as application of various nanoparticle compositions along with physiotherapeutic measures.

The nanoparticles or solutions may be composed of many different ingredients, so that only a general statement can be made about an exact composition that depends on a specific application:

TABLE 2

Composition of nanoparticles according to the invention (percentage/quantities)

| | | relative portion (weight) | |
|---|---|---|---|
| basic structural unit | iron = | 1 | total = 1 |
| | doping with other metals | ≦0.25 | |
| | synthesis polymer(s) | | 0.01–1 |
| | adsorption mediator | | ≦1 |
| | targeting polymer(s) | | 0.5–50 |
| | pharmaceuticals | as required | |
| | pharmaceutical adjuvants | as required | |

The overall diameter of the nanoparticles including all additives (measured with dynamic laser light scattering, DLS) is no greater than ten times the diameter of the iron-containing core (measured using transmission electron microscopy; TEM) Preference is given to those combinations in which the diameter of the basic structural unit (core+primary coat) is increased only to a minor extent by the targeting polymer or combination of targeting polymers plus optional adjuvants. The DLS-measured diameter may exceed the diameter of the basic structural unit by a maximum of 20%.

Nanoparticles of unprecedented flexibility and quality that are suitable for applications requiring high biological specificity and high physical quality (particle size, magnetic properties) can be produced by combining optimum physical properties of the basic structural units with a multitude of potential targeting polymers. The modular design and the many combinations it permits result in a wide range of potential applications.

As the nanoparticles combine high physical quality with excellent targetability by flexible adjustment (modular design) of the targeting polymer (secondary coat) to the respective problem, they are applicable for many special indications such as MR lymphography after intravenous or local interstitial administration, tumor visualization, visualization of functions or malfunctions, of plaque (atherosclerosis imaging), thrombi and vascular occlusions, MR angiography, perfusion imaging, infarct visualization, visualization of endothelial damages, receptor imaging, visualization of blood-brain barrier integrity etc., as well as for differential diagnosis, in particular, for distinguishing tumors/metastases from hyperplastic tissue.

The particles are also suitable for the most varied in-vitro diagnostic applications due to their extraordinary production flexibility. For example, they may be used as specific carriers used in magnetic separation examinations for EIAs enzyme-immunoassays). Selective depletion of specific factors from the blood (ex-vivo detoxification of the blood) is a combination of in-vitro methods with a therapeutic approach.

The nanoparticles according to the invention show distinct self-coloring. When combined with a targeting polymer that results in a particularly high concentration in lymphatic nodes, these particles are excellently suited as intraoperative labeling substances for lymph node staining. As lymphatic nodes are often surgically removed together with tumors, pre-administration of nanoparticles makes it much easier for the operating surgeon to identify these nodes, which may be rather small, in the surrounding tissue. The nanoparticles have a particularly wide time window for this purpose and can be applied from about 60 min. to more than 24 hours prior to the operation.

Apart from lymph node visualization, intratumoral application or application in the tumor periphery facilitates staining of the tumor periphery, which improves distinction of the tumor from the surrounding tissue; in addition, particles in the tumor area are carried off via the same lymph vessels through which the tumor cells will spread metastatically. Thus the particles stain the lymph vessels or nodes that are preferred for metastatic spread.

In addition to their use as intravenously applied contrast material, the particles can be applied locally. Local application may be advantageous in the case of e.g. a mammary carcinoma, as only a limited area has to be visualized, and local administration facilitates high concentrations of the contrast medium in the target area without involving the rest of the system. Indirect purposeful application to the interstitial tissue around certain lymphatic nodes may be required to corroborate a diagnosis where findings after intravenous administration aroused suspicion or doubt.

Another field of application for the nanoparticles is their use as a reinforcing substance in in-vivo diagnostics based on highly sensitive methods of measurement (SQUID) to determine magnetization or magnetic fields/flux densities. Development of highly sensitive methods of measurement in this field have facilitated in-vivo tracing of magnetic particles, so that magnetic particles, similar to radioactive substances used in scintigraphy, can be used for the diagnosis of malfunctions and lesions.

The particles may be used as vehicles for medical substances in the field of therapeutics. The specificity of the nanoparticles is used for the transport of medical substances to their place of action. The medical substances may be incorporated in the iron-containing core or chemically bonded to the synthesis polymer and/or the targeting polymer. Adsorption of conjugates of polymers and medical substances, or bonding of medical substances to adsorption mediators/enhancers, can be viewed as an alternative. Thus, for example, specific peptide sequences can be produced that show high affinity for iron oxide surfaces.

A possible indication could be accumulation of high concentrations of low-molecular chemotherapeutic agents in phagocytizing cells as therapeutically required, for example, for many diseases involving microorganisms that persist in RES cells. In all therapeutic approaches, systems of nanoparticles and medical substances can be selectively accumulated in their target area using external magnetic fields. For treating very special problems, there is the option of implanting small magnets for local control in the target area, e.g. a tumor area.

Apart from using nanoparticles as vehicles for the purposeful transport of medical substances to specified tissues, types of pharmaceuticals may be produced that are characterized by a modified release of active agents. Release of the active agent can be controlled using biologically decomposable conjugates or by inserting the medical substance in various components of the nanoparticle that have a different biodegradability. A potential indication is the use of nanoparticles as a repository for administering hormones.

It is also conceivable to use the nanoparticles in novel therapeutic systems in which the magnetic properties of the nanoparticles induce and control the release of the medical substance via a "magnetic switch" that may also be operated from outside. An important field of application is the development of therapeutic systems for the controlled release of an antidiabetic agent in the treatment of pancreatic diabetes.

Medical substances suitable for direct transport to their place of action by nanoparticles are, first of all, chemotherapeutic agents and cytostatic agents. Also, antimicrobial therapy frequently requires purposeful transport of the medical substance to its place of action (e.g. tuberculosis, microorganisms that persist in macrophages). Medical substances suitable for release by the magnetic properties of the nanoparticles are, in particular, antimicrobiotic agents, hormones, antidiabetic agents, cytostatic agents, and chemotherapeutic agents.

The nanoparticles may be employed over and beyond their indirect therapeutic use as medical substances themselves, e.g. as absorbers in hyperthermia or Mossbauer nuclear absorption therapy, or, if doped appropriately with boron or gadolinium, in neutron capture therapy. Another application is medical radiation therapy for which the nanoparticles are doped with radioactive elements either in their core or by the basic structural unit adsorbing suitable molecules with isotopes or molecules.

A preferred application of the nanoparticles in radiation therapy is, for example, one in which the nanoparticles either contain an "autoradiator" through the radioactive $^{55}$Fe isotope or one in which the nanoparticles contain an isotope that can be induced to become a radiating isotope by external "activation". For example, the core may contain $^{157}$Gd that is externally activated by neutrons.

Another application of the nanoparticles in radiation therapy results from the fact that their core, synthetic or targeting polymer, or adsorption mediator can be modified to contain an autoradiator such as $^{123}$I or $^{125}$I. Alternatively, the nanoparticles may contain an isotope that is converted into a radiating isotope by external triggering. An example is the labeling of the targeting polymer with iodine and external activation of the iodine-K edge using monoenergetic X-ray radiation.

The nanoparticles of the invention can also be used for removing bacteria, viruses, endo- and exotoxins from the vasal space, with inactivation being brought about either by interaction with the nanoparticles themselves, or by their interaction with the RES to identify conjugates/adsorbates and subsequent intracellular inactivation.

BRIEF DESCRIPTION OF THE DRAWINGS

The invention shall now be explained in more detail based on the following examples and the accompanying FIGS. 1 to 35, where:

FIG. 8: Frontal pre- and post-contrast MR tomograms of the pelvic region of the rabbit in the proton-density weighted spin echo sequence (SE 2000/15)

FIG. 9: Frontal pre- and post-contrast MR tomograms of the pelvic region of the rabbit in the proton-density weighted spin echo sequence (SE 2000/15).

FIG. 11: Frontal pre- and post-contrast MR tomograms of the pelvic region of the rabbit in the T2*-weighted gradient echo sequence (GE 135/15/15°)

FIG. 32: Histochemical detection (Prussian blue staining) of accumulated nanoparticles according to Example E6 in the aorta of a Watanabe rabbit.

DETAILED DESCRIPTION OF THE INVENTION

Figure 1:
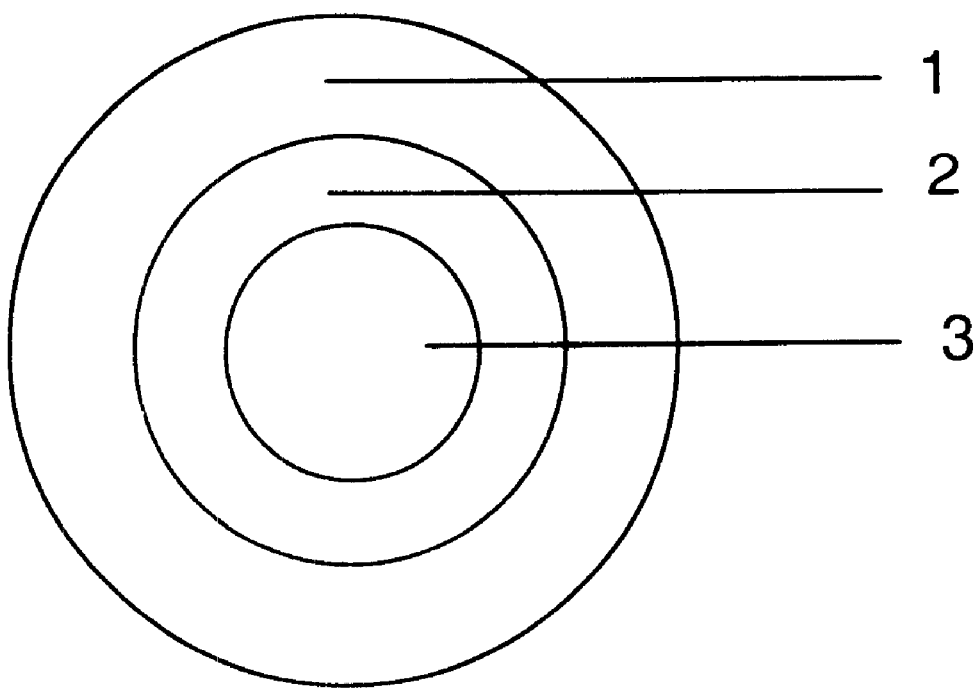
FIG. 1: Sectional structure of the nanoparticles with iron-containing core, primary coat (synthesis polymer) and secondary coat (targeting polymer)

FIG. 1 is a sectional view of the nanoparticles according to the invention, including an iron-containing core 3, a synthesis polymer (=primary coat) 2, and a targeting polymer (=second coat) 1. The iron-containing core+primary coat (basic structural unit) can be combined with the targeting polymer (second coat) at any time. The basic structural unit determines physical quality while the targeting polymer (secondary coat) forms the surface of the nanoparticle and determines its in-vivo behaviour.

As an option, the adsorptive bonding of primary and secondary coats can be improved, or facilitated, by adsorption mediators. The option of additional adsorption of pharmaceutic adjuvants or drugs is not shown here.

Figure 2:
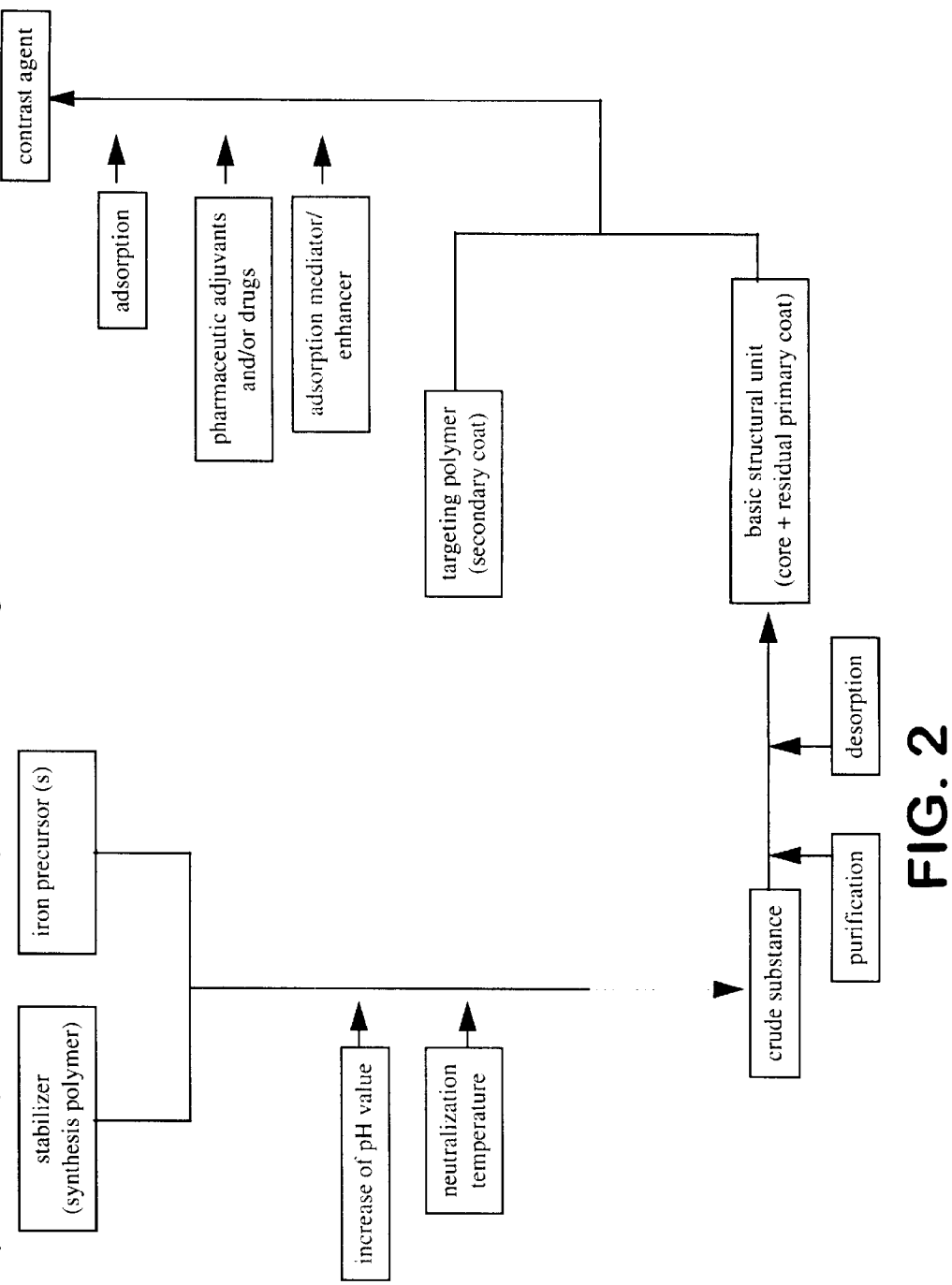
FIG. 2: General diagram showing synthesis of the nanoparticles according to the invention

FIG. 2 illustrates a general overview (flow diagram) of a process to produce the nanoparticles according to the invention. The great number of possible variants, e.g., to produce the "crude substances", cannot be shown in the diagram, but it can be seen that the nanoparticles have a modular design and are "completed" by combining various structural units or blocks. The essential characteristic is that the basic structural unit with the primary coat and the targeting polymer are produced separately.

EXAMPLES OF PRODUCTION AND APPLICATION

A: Production of Synthesis Polymers

A1 Synthesis of (Mono)carboxydextran (CDx)

100 g of dextran 4 (Serva, Germany) are dissolved in 500 ml water and heated to 60°C. About 55 ml of approximately 10 N soda lye is added while being stirred. The solution is (partly) neutralized to pH 8 after a reaction time of 5 hours. The brown solution is then purified on a mixed-bed ion exchanger (Amberlite IRA-400 and IR-120). The fractions having acidic properties are pooled and concentrated in a vacuum in the rotary evaporator at 40° C. Then they are freeze-dried.

TABLE 3

Analytic data:

| | Dimension | Result | Method |
|---|---|---|---|
| molecular weight | g/mol | ca. 2,000 | size exclusion chromatography (SEC) |
| acid content (%) | % | 7.3 ± 0.4 | potentiometric titration |
| carboxylic acid - pKs | | 3.6–3.8 | potentiometric titration |
| optical rotation (water) | (degree) | +156.9°± 9.9 | polarimeter with circular scale (Zeiss) |
| yield | % | 59 | anthrone method |
| ultimate analysis | | | |
| water | % | 0.70 | |
| carbon | % | 41.25 | |
| hydrogen | % | 6.30 | |

Figure 3:
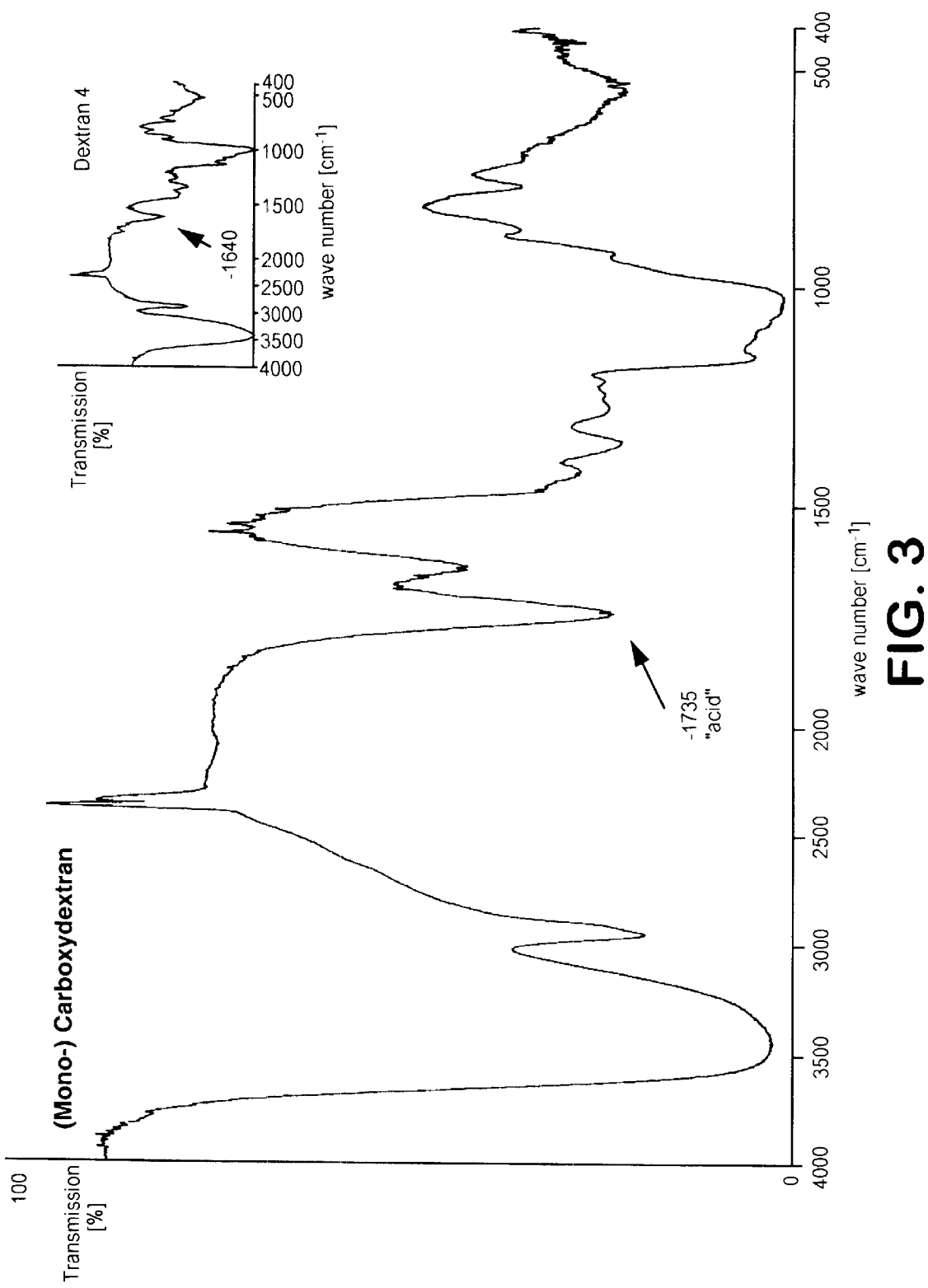
FIG. 3: FTIR spectrum of monocarboxydextran and its parent compound dextran 4

The FTIR spectrum (potassium bromide) of the modified dextran (=carboxydextran) is shown in FIG. 3. The spectrum of dextran 4 (Serva), the parent compound, has been inserted for comparison.

A2 Synthesis of Polycarboxydextran (P-CDX)

10 g of dextran T10 (Pharmacia, Germany) are weighed into a 250 ml two-neck flask and mixed with 100 ml of 4 N NaOH. One neck of the flask is equipped with a reflux condenser, and the solution is heated to ca. 80° C. 30 g of 6-bromohexanoic acid (Aldrich, Germany) are added in portions via the second neck with constant stirring (magnetic stirrer). The neck is plugged after the substance has been added and the reaction mixture kept agitated for another 3 hours. After the reaction, the batch is neutralized under a fume hood using 6 N HCl and then reduced by preliminary concentration using a rotary film evaporator (60° C., vacuum). Separation of the unconverted reactant, or cleaning of the modified carboxydextran, is carried out by precipitation with ethanol. The white precipitate is washed, redissolved in double distilled water, and finally filtered through an 0.22 μm filter (Schleicher and Schüll, Germany) and lyophilized.

TABLE 4

Analytic data

| | Dimension | Result | Method |
|---|---|---|---|
| molecular weight | g/mol | ca. 12.000 | size exclusion chromatography (SEC) |
| acid content (%) | % | 19.86 ± 1.2 | potentiometric titration |
| carboxylic acid - pKs | | 4.4–4.8 | potentiometric titration |
| optical rotation (water) | (degrees) | +109.3°± 6.9° | polarimeter with circular scale (Zeiss) |
| yield | % | 95 | anthrone method |
| ultimate analysis | | | |
| water | % | 2.3 | |
| carbon | % | 49.7 | |
| hydrogen | % | 5.4 | |

Figure 4:
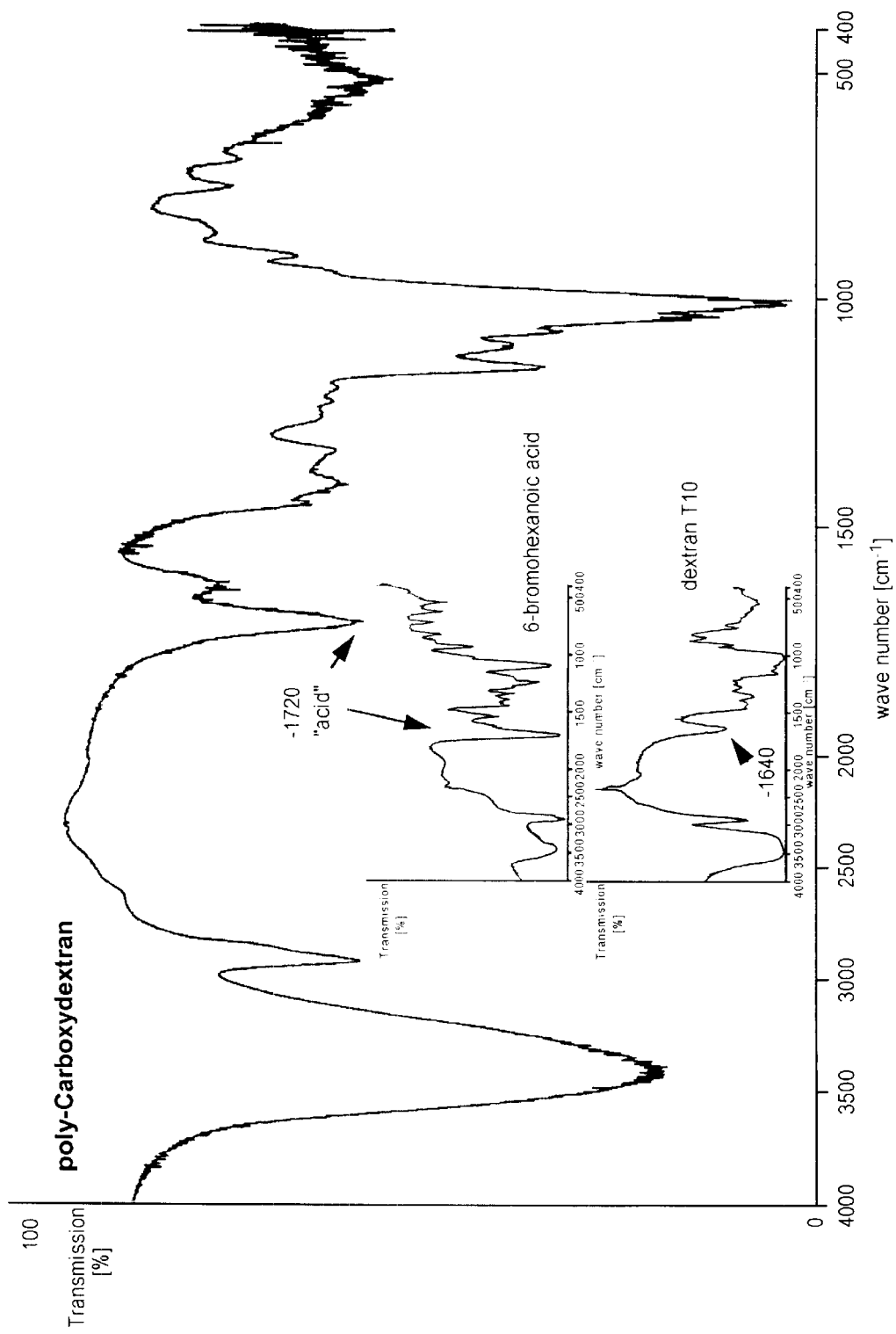
FIG. 4: FTIR spectrum of polycarboxydextran and its parent compounds dextran T10 and 6-bromohexanoic acid

The FTIR spectrum of the polycarboxydextran is shown in FIG. 4 (see Annex). The spectra of dextran T10 (Pharmacia) and 6-bromo-hexanoic acid (Sigma), the parent compounds, were inserted for comparison.

B: Production of the Crude Substances

B1 Production from CDx Using Ammonia Gas 5.0 g of monocarboxydextran (CDx, Example A1) having a molecular weight of ca. 2000 Da are dissolved in 17.5 ml of double distilled water. The solution is degasified by blowing in nitrogen. 6.7 ml of 1-molar iron(III) chloride hexahydrate solution are prepared in a test tube and degasified using nitrogen. 648 mg of iron(II) chloride tetrahydrate are added to the iron(III) solution and dissolved in the nitrogen stream. The polymer solution is heated to ca. 75° C., and the iron solution added (with exposure to nitrogen gas). The heated reaction mixture is adjusted to alkaline by the quick introduction of ammonia from a gas cylinder while mixing thoroughly. Then the reaction solution is refluxed for about 1 hour. It is subsequently heated for another 10 minutes in the open flask to sweep out the unconverted ammonia. It is centrifuged at 2500 g for 30 min. after cooling, and the filtrate is evaporated down to about 7 ml using a rotary evaporator; the pH value is checked and neutralized, if required. After the concentration is determined, the solution is adjusted to a ca. 1-molar iron concentration with double distilled water and filtered using a 0.22 μm filter. The solution can be sterilized in an autoclave (method A121).

TABLE 5

Analytic data:

| | Dimension | Result | Comment |
|---|---|---|---|
| Content | | | |
| yield (iron) | % | 87 | |
| content (iron) | mol/l | 1 | ICP atomic emission spectroscopy |
| iron(II)/total iron | % | 9.8 | phenanthroline method |
| polymer (C-dextran) | mg/ml | 500 | anthrone method |
| polymer/iron: Dimensions | (g/g) | 9:1 | |
| core diameter | nm ± SD | 3.8 ± 0.8 | electron microscope (TEM) |
| overall | nm ± SD | 9.9 ± 6.1 | laser light scattering |

TABLE 5-continued

Analytic data:

| | Dimension | Result | Comment |
|---|---|---|---|
| diameter | nm | 11.1 | (DLS) exclusion chromatography |
| relaxivity and susceptibility | | | |
| susceptibility | EMU/g | 64 | magnetic balance |
| T1 relaxivity | 1 mmol$^{-1}$ s$^{-1}$ | 54 | minispec pc 120 |
| T2 relaxivity | 1 mmol$^{-1}$ s$^{-1}$ | 24 | minispec pc 120 |
| Half-life in the blood (200 μmol/kg body wt, rat, n = 5) | min | 88<br>94<br>101 | (T1)[1]<br>(T2)[2]<br>(Fe)[3] |

Notes 1 to 3: Determination of Half-life in the Blood

Half-life of Clearance from the Blood

A catheter of 50.5 cm length filled with heparinized sodium chloride solution (0.2 ml) is implanted in the common carotid artery of the etherized experimental animals (rat, ca. 200 g) and pushed forward about 1.5 cm to the heart. The free end of the catheter was led out and fixed with histoacrylate.

The test substance is applied i.v. via the caudal vein (ca. 1 ml/min.) about an hour after the end of the operation. Blood samples were taken at various times according to the expected elimination rates of the test substances when the animals were awake. At the end of the test the animals were killed under ether anaesthesia by draining the blood from the caval vein.

Half-life of the T$_1$ and T$_2$ Effects

The blood samples are centrifuged at 2900 rpm (1000 g) for 15 min. 0.250 ml of the supernatant liquid are drawn off. The samples are filled to 2.0 ml with double distilled water and the mixture then thermostated at 40° C.

Decreasing blood concentration is determined by measuring the T$_{1,2}$ relaxation times with a pc120 relaxometer (Bruker, Germany). The measurement was carried out either with a 180°–90°-IR-(inversion recovery) sequence (T$_1$) or a CPMG sequence (T$_2$).

The results were analyzed based on a pharmacokinetic two-compartment model; the data were calculated using the TOPFIT pharmacokinetic computer program by protracting the concentrations over time in terms of reciprocal T$_{1,2}$ times (relaxation rates) minus the blank reading. TOPFIT first calculates the slope of the straight line by linear regression from the floating point notation of "concentration" and time, and then the effective half-live from the values obtained.

Half-life Over Iron Content

800 μl of the solutions used for determining relaxation time were withdrawn by pipette, dissolved with concentrated nitric acid, and filled to 10.0 ml with double distilled water. The iron content is then quantified using atomic emission spectroscopy (AES). The results are converted into blood concentrations and analyzed by means of a concentration-time diagram using TOPFIT, while taking into account the relevant dilution factors.

B2: Production of P-CDx with NaOH and Fe(III) Citrate and Fe(II) gluconate 5.0 g of polycarboxydextran (Example A2) with a molecular weight of ca. 12000 Da are dissolved in 17.5 ml of double distilled water. The solution is degasified by blowing in nitrogen. 6.7 ml of 1-molar iron(III) citrate monohydrate solution are prepared in a test tube and degasified using nitrogen. 1.635 g of iron(II) gluconate trihydrate are added to the iron(III) solution and dissolved in the nitrogen stream. The polymer solution is heated to ca. 75° C., and the iron solution added (with exposure to nitrogen gas). Ca. 12 ml of 3 N soda lye are added to the heated reaction mixture within 30 seconds while mixing thoroughly. Then the reaction solution is neutralized with ca. 6 N hydrochloric acid and refluxed for about 1 hour. It is subsequently heated for another 10 minutes in the open flask to sweep out the unconverted ammonia. It is centrifuged at 2500 g for 30 min. after cooling, and the filtrate evaporated down to about 7 ml using a rotary evaporator; the pH value is checked and neutralized, if required. After the concentration is determined, the solution is adjusted to a ca. 1-molar iron concentration with double distilled water and filtered using the 0.22 μm filter. The solution can be sterilized in an autoclave (method A121).

TABLE 6

Analytic data:

| | Dimension | Result | Comment |
|---|---|---|---|
| Content | | | |
| yield (iron) | % | 84 | |
| content (iron) | mol/l | 1 | ICP atomic emission spectroscopy |
| Fe(II)/total Fe | % | 11.4 | phenanthroline method |
| polymer (P-dextran) | mg/ml | 505* | anthrone method |
| polymer/iron: Dimensions | (g/g) | 9:1 | |
| core diameter | nm ± SD | 4.1 ± 1.3 | electron microscope (TEM) |
| overall diameter | nm ± SD | 20.4 ± 8.4 | laser light scattering (DLS) |
| | nm | ca. 27 | size exclusion chromatography (SEC) |
| Relaxivity and Susceptibility | | | |
| susceptibility | EMU/g | 77 | magnetic balance |
| T1 relaxivity | 1 mmol$^{-1}$ s$^{-1}$ | 24 | minispec pc 120 |
| T2 relaxivity | 1 mmol$^{-1}$ s$^{-1}$ | 64 | minispec pc 120 |
| Half-life in the blood (200 μmol/kg body wt, rat, n = 5) | min | 68<br>64<br>59 | (T1)<br>(T2)<br>(Fe)<br>see notes for example B1 |

*P-CDx content is calculated from glucose equivalents multiplied by 1.64 (100 mg P-CDx = 61 mg of glucose equivalents)

B3: Production from CDx with Fe(III) NTA and Ammonium Hydroxide 5.0 g of (mono)carboxydextran (CDx, Example A1) with a molecular weight of ca. 2000 Da are dissolved in 35 ml of double distilled water. The solution is degasified by blowing in nitrogen. Concentrated ammonium hydroxide solution (32%) is added to the reaction mixture while heating and mixing thoroughly until the pH value is adjusted to 11. 6.85 ml of 1-molar iron(III) solution are prepared in a test tube, mixed with an equimolar quantity of NTA, and degasified using nitrogen. 667 mg of iron(II) chloride tetrahydrate are added to the iron(III) solution and dissolved in the nitrogen stream. The iron solution is added to the alkaline polymer solution within 20 seconds. Then the reaction solution is neutralized with ca. 6 N hydrochloric acid and refluxed for about 1 hour. It is centrifuged at 2500 g for 30 min. after cooling, the filtrate is evaporated down to about 6 ml using the rotary evaporator, and the pH value is measured. After determining the concentration, the solution is adjusted to a ca. 1-molar iron concentration with double distilled water and filtered using a 0.22 μm filter. The solution can be sterilized in an autoclave (method A121).

TABLE 7

Analytic data:

| | Dimension | Result | Comment |
|---|---|---|---|
| Content | | | |
| yield (iron) | % | 69 | |
| content (iron) | mol/l | 1 | ICP atomic emission spectroscopy |
| iron-II/total iron | % | 7.1 | phenanthroline method |
| polymer (P-dextran) | mg/ml | 421 | anthrone method |
| polymer/iron: dimensions | (g/g) | 8:1 | |
| core diameter | nm ± SD | 5.5 ± 2.3 | electron microscope (TEM) |
| overall diameter | nm ± SD | 24.4 ± 8.4 | laser light scattering (DLS) |
| | nm | ca. 31 | size exclusion chromatography (SEC) |
| Relaxivity and Susceptibility | | | |
| susceptibility | EMU/g | 96 | magnetic balance |
| T1 relaxivity | 1 mmol$^{-1}$ s$^{-1}$ | 33 | minispec pc 120 |
| T2 relaxivity | 1 mmol$^{-1}$ s$^{-1}$ | 148 | minispec pc 120 |
| Half-life in the blood (200 μmol/kg body wt, rat, n = 5) | min | 59<br>54<br>58 | (T1)<br>(T2)<br>(Fe)<br>see notes for example B1 |

B4: Production from P-CDx with Iron(III) and Reducing Agent, Soda Lye 5.0 g of polycarboxydextran (Example A2) with a molecular weight of ca. 12000 Da are dissolved in 17.5 ml of double distilled water. The solution is degasified by blowing in nitrogen. 10 ml of 1-molar iron(III) chloride hexahydrate solution are added to the polymer solution, then degasification using nitrogen is continued. The polymer solution is heated to ca. 75° C., and 113.6 mg of hydroxylamine HCl are added under nitrogen gas. Ca. 12 ml of 3 N soda lye are added to the heated reaction mixture within 30 seconds while mixing thoroughly. Then the reaction solution is neutralized with ca. 6 N hydrochloric acid and refluxed for about 1 hour. It is centrifuged at 2500 g for 30 min. after cooling, and the filtrate is evaporated down to about 7 ml using the rotary evaporator; the pH value is checked. After determining the concentration, the solution is adjusted to a ca. 1-molar iron concentration with double distilled water and filtered using a 0.22 μm filter. The solution can be sterilized in an autoclave (method A121).

TABLE 8

Analytic data:

| | Dimension | Result | Comment |
|---|---|---|---|
| Content | | | |
| yield (iron) | % | 84 | |
| content (iron) | mol/l | 1 | ICP atomic emission spectroscopy |

TABLE 8-continued

Analytic data:

| | Dimension | Result | Comment |
|---|---|---|---|
| iron-II/total iron | % | 5.4 | phenanthroline method |
| polymer (P-dextran) | mg/ml | 515 | anthrone method |
| polymer/iron: Dimensions | (g/g) | 9:1 | |
| core diameter | nm ± SD | 4.5 ± 1.4 | electron microscope (TEM) |
| overall diameter | nm ± SD | 21.4 ± 5.4 | laser light scattering (DLS) |
| | nm | ca. 24 | size exclusion chromatography (SEC) |
| Relaxivity and Susceptibility | | | |
| susceptibility | EMU/g | 88 | magnetic balance |
| T1 relaxivity | 1 mmol$^{-1}$ s$^{-1}$ | 28 | minispec pc 120 |
| T2 relaxivity | 1 mmol$^{-1}$ s$^{-1}$ | 138 | minispec pc 120 |
| Half-life in the blood (200 μmol/kg body wt, rat, n = 5) | min | 57<br>55<br>51 | (T1)<br>(T2)<br>(Fe)<br>see notes example B1 |

B5: Production with a Mixture of Dextran 4 and Dextran 15

5.0 g of a 1:1 mixture of dextran 4 and dextran 15 (both Serva, Germany) having a molecular weight of ca. 4,000–6,000 Da and 15,000–20,000 Da, respectively, are dissolved in 20 ml of double distilled water. The colorless polymer solution is adjusted to a pH value of ca. 12 using 3 N soda lye, refluxed for 1 hour, and neutralized with ca. 6 N HCl. The dark reddish brown solution is degasified by blowing in nitrogen. 6.7 ml of 1-molar iron(III) chloride hexahydrate solution are prepared in a test tube and degasified using nitrogen. 648 mg of iron(II) chloride tetrahydrate are added to the iron(III) solution and dissolved in the nitrogen stream. The polymer solution is heated to ca. 75° C., and the iron solution added (while exposed to nitrogen gas). 11.5 ml of 3 N soda lye are added to the heated reaction mixture within 30 seconds while mixing thoroughly. Then the reaction solution is refluxed for about 1 hour. It is centrifuged at 2500 g for 30 min. after cooling, and the filtrate is evaporated down to about 8 ml using a rotary evaporator; the pH value is checked. After determining the concentration, the solution is adjusted to a ca. 1-molar iron concentration with double distilled water and filtered using a 0.22 μm filter. The solution can be sterilized in an autoclave according to method A121.

TABLE 9

Analytic data:

| | Dimension | Result | Comment |
|---|---|---|---|
| Content | | | |
| yield (iron) | % | 91 | |
| content (iron) | mol/l | 1 | ICP atomic emission spectroscopy |
| iron-II/total iron | % | 12.8 | phenanthroline method |
| polymer (P-dextran) | mg/ml | 570 | anthrone method |

TABLE 9-continued

Analytic data:

| | Dimension | Result | Comment |
|---|---|---|---|
| polymer/iron: Dimensions | (g/g) | 10:1 | |
| core diameter | nm ± SD | 4.0 ± 1.1 | electron microscope (TEM) |
| overall diameter | nm ± SD | 18.1 ± 3.4 | laser light scattering (DLS) |
| | nm | ca. 21 | size exclusion chromatography (SEC) |
| Relaxivity and Susceptibility | | | |
| susceptibility | EMU/g | 68 | magnetic balance |
| T1 relaxivity | 1 mmol$^{-1}$ s$^{-1}$ | 21 | minispec pc 120 |
| T2 relaxivity | 1 mmol$^{-1}$ s$^{-1}$ | 78 | minispec pc 120 |
| Half-life in the blood (200 μmol/kg body wt, rat, n = 5) | min | 61<br>59<br>67 | (T1)<br>(T2)<br>(Fe)<br>see notes example B1 |

C: Production of the Basic Substances

C1: Dialysis Against Water 5 ml of the solution according to Example B1 are filled in a Visking dialysis tube (Serva, Germany) and dialyzed five times, each time for 6 hours, against 1 l of fresh double distilled water. The retentate is adjusted to an iron concentration of 200 mmol/l by dilution with double distilled water and filled in portions of 5 ml through 0.22 μm filters (cellulose acetate. "Rotrand", Fa. Schleicher & Schüll, Germany) into sterile 10 ml vials. The desorbed solution can be sterilized in an autoclave.

C2: Dialysis Against 20 mMol Sodium Citrate 5 ml of the solution according to Example B1 are filled in a Visking dialysis tube and dialyzed five times, each time for 6 hours, against 1 l of fresh sodium lactate solution (20 mmol/l, pH 7). Dialysis is repeated twice, each time for 5 hours, against 1 l of fresh double distilled water. The retentate is adjusted to an iron concentration of 200 mmol/l by dilution with double distilled water and filled in portions of 5 ml through 0.22 μm filters into sterile 10 ml vials.

C3: Ultrafiltration with Amicon 5 ml of the solution according to Example B1 are pipetted into a preparative ultrafiltration device and filled to the 15 ml mark with double distilled water (Centriprep 100, Cut off 100 kDa, Fa. Amicon, Germany) and ultrafiltered for 1 h at 1000 g. The filtrate is then discarded and the container of the retentate filled to the 15 ml mark with fresh double distilled water, and ultrafiltered again. This procedure is repeated twice. The retentate is adjusted to an iron concentration of 200 mmol/l by dilution with double distilled water and filled in portions of 5 ml through 0.22 μm filters (cellulose acetate) into sterile 10 ml vials.

C4: Chromatoaraphic Separation 5 ml of the solution according to Example B1 are filled in a 10 ml superloop (Fa. Pharmacia) on a S400HR sephacryl column (100×5 cm) and eluted in 50 mM citric acid/250 mM mannite at a flow rate of 300 ml/hour. The fraction from 450 ml to 840 ml is collected and concentrated to ca50 ml using a rotary evaporator at 60° C. in a vacuum. The concentrate is dialyzed three times for 6 hours against double distilled water, concentrated again in the rotary evaporator and adjusted to a concentration of 200 mmol iron/l after determination of the iron content. The solution is filled in portions of 5 ml through 0.22 μm cellulose acetate filters into sterile 10 ml vials. The desorbed solution can be sterilized in an autoclave.

TABLE 10 analytical data of the base compounds according to Example C1–C4

| Example | Yield (Fe) | Polymer : Iron [= 200 mmol/l] (g/g) |
|---|---|---|
| C1 | 96% | 0.501 ± 0.025 |
| C2 | 94% | 0.300 ± 0.020 |
| C3 | 89% | 0.610 ± 0.041 |
| C4 | 67% | 0.143 ± 0.030 |

The physico-chemical data regarding the magnetic properties and size parameters correspond to the values of the parent compound (Example B1).

D: Solutions for Application

D1 Dextran T10

5.0 ml of solution according to Example C1 at a concentration of 200 mmol Fe/l (corresponding to 56 mg of total iron content) are prepared in a 10 ml vial. 33.6 mg of dextran T10 as the targeting polymer are dissolved in 6.0 ml of distilled water and 5.0 ml of this solution are added to the iron oxide solution in aseptic conditions using a syringe with a filter attachment (0.22 μm). The polymer-to-iron weight quotient is 1 (residual synthesis polymer=28 mg+targeting polymer=28 mg).

The preparation now contains 10 ml of a 100 mmolar (iron) solution that is immediately suitable for application in intravenous MR lymphography.

D2: Dextran FP1: Production from 2 Solutions 5.0 ml of solution according to Example C1 at a concentration of 200 mmol Fe/l (corresponding to 56 mg of total iron content) are prepared in a 10 ml vial. 302.4 mg of dextran FP1 as the targeting polymer are dissolved in 6.0 ml of distilled water, 5.0 ml of which are added to the iron oxide solution in aseptic conditions using a syringe with a filter attachment (0.22 μm). The polymer-to-iron weight quotient is 5 (residual synthesis polymer=28 mg+targeting polymer= 252 mg).

The preparation now contains 10 ml of a 100 mmolar (iron) solution that is immediately suitable for application in intravenous MR lymphography.

D3: Dextran FP1 as Lyophilisate 5.0 ml of solution according to Example C1 at a concentration of 200 mmol Fe/l (corresponding to 56 mg of total iron content) are prepared in a 10 ml vial. 302.4 mg of dextran FP1 as the targeting polymer are dissolved in 6.0 ml of distilled water, 5.0 ml of which are added to the iron oxide solution in aseptic conditions using a syringe with a filter attachment (0.22 μm). The polymer-to-iron weight quotient is 5 (residual synthesis polymer=28 mg+targeting polymer= 252 mg).

The solution is lyophilized in the injection bottle, and the bottle is plugged.

The solution for application is prepared by adding 10 ml of physiological saline; the bottle now contains 10 ml of a 100 mmolar (iron) solution that is immediately suitable for application in intravenous MR lymphography.

D4: Dextran FP1

252 mg of dextran FP1 as the targeting polymer are weighed-in in a 5 ml injection bottle and filled with 5.0 ml of the solution according to Example C1 at a concentration of 200 mmol Fe/l (corresponding to 56 mg of total iron content), and the flask is plugged. The dextran FP1 is dissolved by turning the injection bottle. The polymer-to-iron weight quotient is 5 (residual synthesis polymer=28 mg+targeting polymer=252 mg).

The preparation now contains 5 ml of 200 mmolar (iron) solution that is immediately suitable for application in intravenous MR lymphography.

D5: Laminarin 5.0 ml of solution according to Example C1 at a concentration of 200 mmol Fe/l (corresponding to 56 mg of total iron content) are prepared in a 10 ml vial. 33.6 mg of laminarin as the targeting polymer are dissolved in 6.0 ml of distilled water, 5.0 ml of which are added to the iron oxide solution in aseptic conditions using a syringe with a filter attachment (0.22 μm). The polymer-to-iron weight quotient is 1 (residual synthesis polymer=28 mg+targeting polymer= 28 mg).

The preparation now contains 10 ml of a 100 mmolar (iron) solution that is immediately suitable for application in intravenous MR lymphography.

D6: with Transferrin 5.0 ml of solution according to Example C1 at a concentration of 200 mmol Fe/l (corresponding to 56 mg of total iron content) are prepared in a 10 ml vial. 33.6 mg of human $Fe_2$ transferrin as the targeting polymer are dissolved in 6.0 ml of distilled water, 5.0 ml of which are added to the iron oxide solution in aseptic conditions using a syringe with a filter attachment (0.22 μm). The polymer-to-iron weight quotient is 1 (residual synthesis polymer=28 mg+targeting polymer=28 mg).

The preparation now contains 10 ml of a 100 mmolar (iron) solution that is suitable for application as a specific contrast medium for visualizing proliferating cells (tumors).

D7 with Endothelin Agonist 5.0 ml of solution according to Example C1 at a concentration of 200 mmol Fe/l (corresponding to 56 mg of total iron content) are prepared in a 10 ml vial. 33.6 mg of an endothelin-receptor-specific heptapeptide Cys-His-Leu-Asp-Ile-Ile-Trp (SEQ ID NO:4) as the targeting polymer are dissolved in 6.0 ml of double distilled water, 5.0 ml of which are added to the iron oxide solution in aseptic conditions using a syringe with a filter attachment (0.22 μm). The polymer-to-iron weight quotient is 1 (residual synthesis polymer=28 mg+targeting polymer=28 mg).

The preparation now contains 10 ml of a 100 mmolar (iron) solution that is suitable for application in intravenous MR plaque imaging (atherosclerosis imaging).

E: Applications

Application Example E1

MR Lymphography in the Rat

Objective: Comparison of relative signal intensity in various lymphatic nodes/groups of lymphatic nodes between the parent compound (synthesis polymer=targeting polymer) and a modification produced according to the desorption-adsorption-method (synthesis polymer≠targeting polymer) in the rat.

Substance: Specific nanoparticles (Example D5); comparison=basic structural unit according to Example C1 (=D5 without targeting polymer)

Dosage: 100 μmol Fe/kg body weight (body wt)

Times: 24 h p. i. host injectionem)

MR method:

Device: Siemens Magnetom 1.5 T MR whole-body MR scanner with extremity coil

MR parameters: Field of view (FOV)=150 mm, matrix=256×256; slice thickness=3 mm section orientation=frontal Sequence 1: Proton-density-weighted spin echo sequence (SE) with TR=2000 ms and TE=15 ms Sequence 2: T2-weighted gradient echo sequence (GE) with TR=135 ms and TE=15 ms; FA=15°

Ex-vivo model:

Accumulation in the Lymphatic Nodes of Rats and Rabbits

An ex-vivo agar phantom was used to examine the accumulation and distribution of substances in various lymphatic nodes/groups of lymphatic nodes. This ex-vivo model has the advantage that accumulation in various central and peripheral lymphatic nodes or lymph node groups can be assessed even for small experimental animals (mouse, rat, rabbit); it also makes it possible to draw conclusion about distribution homogeneity; signal interference can be quantified.

The nanoparticle solution is injected (bolus) in the experimental animals via the caudal (mouse, rat) or the ear vein (rabbit). The animals are sacrificed after 24 hours, and various lymph nodes or lymph node groups are prepared (popliteal, iliac, axillary, mandibular, inguinal lymph nodes). The lymph nodes are then placed in an agar phantom and kept refrigerated until the MR measurement is carried out (max. 24 hours).

Manufacture of the Ex-vivo Agar Phantom 10 g of microbiological agar-agar are suspended in 500 ml of double distilled water to which 0.5 ml of magnevist (0.5 mol/l gadolinium DTPA dimeglumin) has been added for a homogeneous signal background of the MR tomogram. The suspension is boiled up, then cooled to 80° C. and kept at this temperature. About half of the agar solution is poured into a plastic dish to form a layer having a thickness of 0.5 to 1 cm. After allowing the solution to cool down, the specimens are arranged on the agar layer (according to left/right body half, or "in physiological order" from top to bottom) and fixed with a little agar solution (Pasteur pipette). Finally, a second layer of agar solution is poured over the tissue samples. The phantom is measured within 24 hours and kept refrigerated until the measurement has been performed.

The animals that were not injected with nanoparticles are taken along for reference and the tissues prepared identically, or a respective phantom is produced.

Apart from visual inspection, relative signal reduction in the individual tissues is now quantified according to:

$$\text{relative signal intensity} = \frac{\text{signal intensity}_{\text{with nanoparticle}}}{\text{signal intensity}_{\text{without nanoparticle}}}$$

The tissue samples are carefully removed from the agar solution after the measurement, decomposed in concentrated hydrochloric acid and their iron content quantified using ICP AES (inductively coupled plasma atomic emission spectroscopy). The blank values (without contrast medium) were determined from adequately treated control animals without any application of nanoparticles and taken into account when the iron content of the samples was determined.

Figure 5:
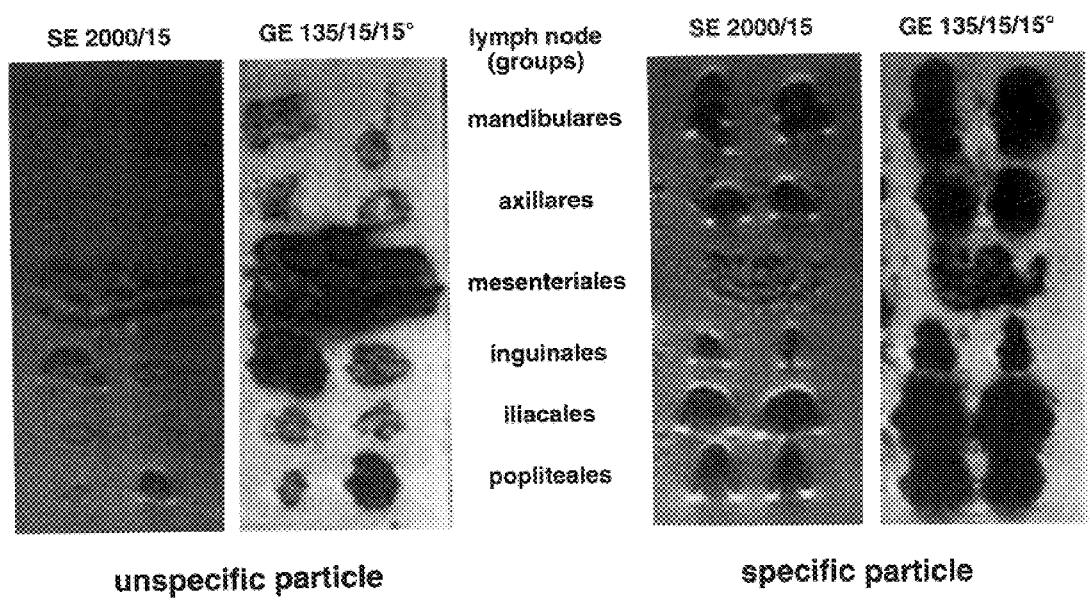
FIG. 5: MR tomograms of agarose-embedded lymphatic nodes of rats

Result:

FIG. 5: MR tomograms of agarose-embedded lymphatic nodes of rats; resection carried out 24 h after application of the reference (Example C2, left) or modified substance according to Example D2 (right); dose 100 μmol Fe/kg in each case FIG. 6: Modified charge vs. original substance: Quantitative evaluation (from FIG. 5) of relative signal intensities for SE 2000/15 in various lymphatic nodes of the rat 24 h after the application of magnetite (100 μmol Fe/kg)

Figure 7:
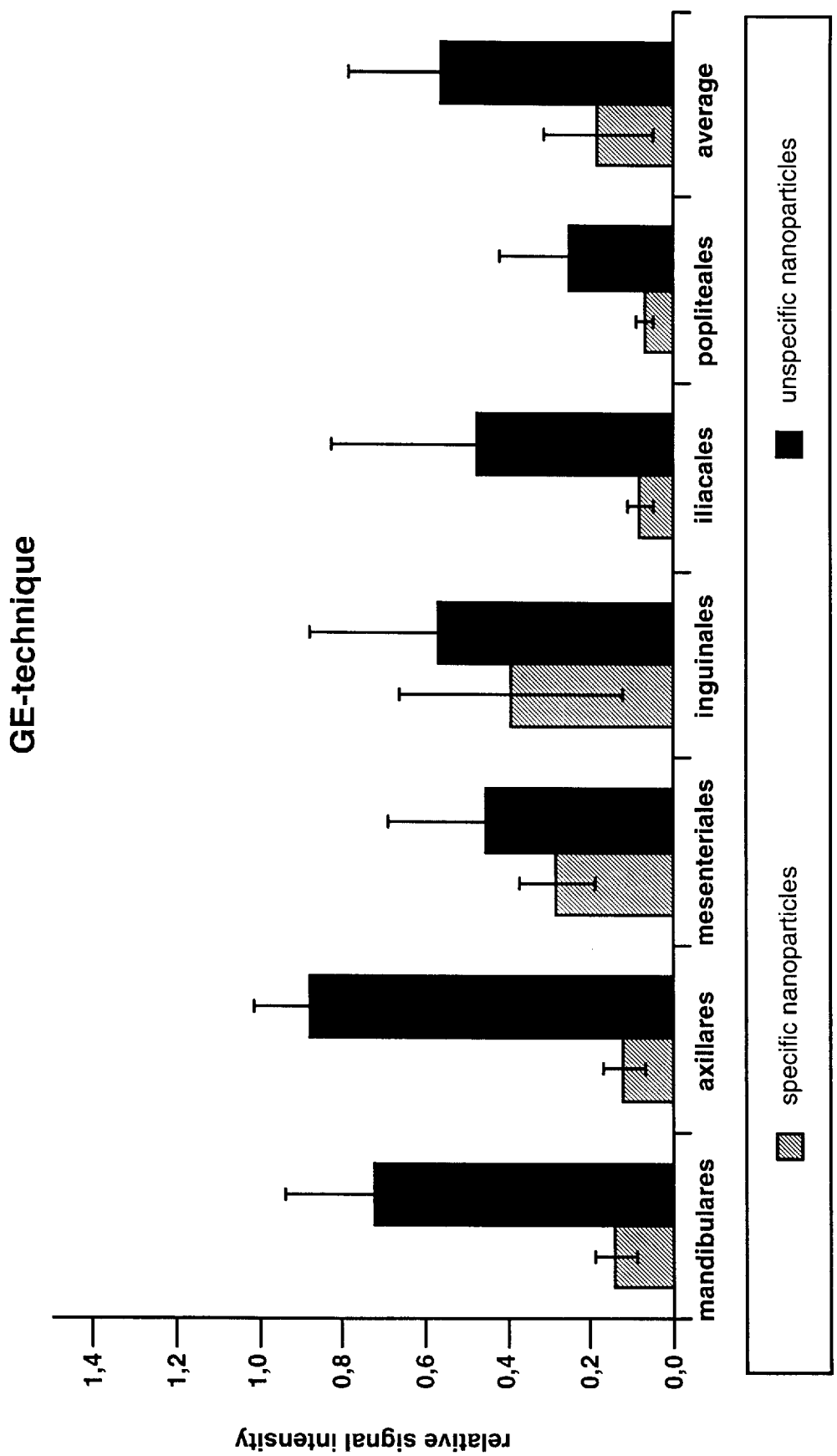
FIG. 7: Quantitative evaluation (from FIG. 5) of relative signal intensities for GE 135/15/15° in various lymphatic nodes of the rat

FIG. 7: Modified charge vs. original substance: Quantitative evaluation (from FIG. 5) of relative signal intensities for GE 135/15/15° in various lymphatic nodes of the rat 24 h after the application of magnetite (100 μmol Fe/kg)

Figure 6:
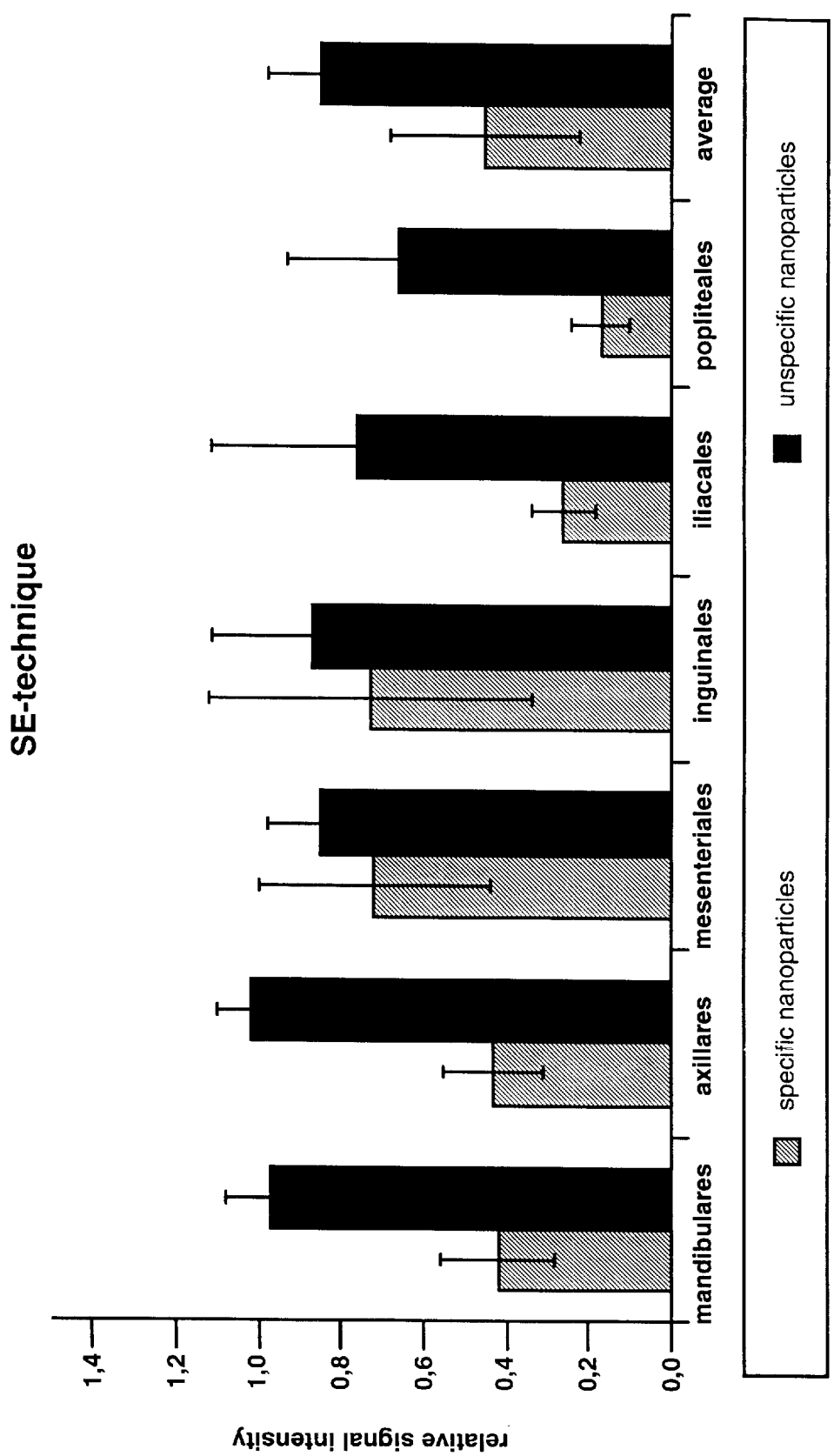
FIG. 6: Quantitative evaluation (from FIG. 5) of relative signal intensities for SE 2000/15 in various lymphatic nodes of the rat

An analysis of interference with the relative lymphonodal signal intensity of the specific nanoparticles (FIG. 6=SE; FIG. 7=GE) demonstrates clearly that the modified substance is accumulated more homogeneously in the lymph nodes than the original substance. Lymphonodal signal reduction of mandibular, axillary, iliac, popliteal lymph nodes as well as the mean accumulation throughout all the lymph node groups caused by the modified batch with a secondary coat of dextran FP1 differs significantly (t-test, p <0.05) from the unmodified parent compound (FIGS. 6 and 7).

The superiority of the specific nanoparticles is impressively illustrated by a look at the "blackening" (FIG. 5) of the individual lymph nodes in FIG. 5. The homogeneous distribution throughout all the lymph nodes examined is particularly remarkable.

Application Example E2

MR Lymphography in the Rabbit

Objective: comparison of relative signal intensity in various lymphatic nodes/groups of lymphatic nodes between the parent compound (synthesis polymer=targeting polymer) and a modification produced according to the desorption-adsorption method (synthesis polymer≠targeting polymer) in the rabbit.

Substance: Specific nanoparticles (Example D2); comparison=basic structural unit according to Example C2(=D2 without targeting polymer)

Dosage: 150 μmol Fe/kg body weight (body wt)

Times: 24 h p. i. (post injectionem)

MR method: MR tomography (SE and GE methods) (see Application Example E1)

In-vivo model: rabbit with induced lymph node hyperplasia

Ex-vivo model: agarose phantom

Result:

FIG. 8: Frontal pre- and post-contrast MR tomograms of the pelvic region of the rabbit in the proton-density-weighted spin echo sequence (SE 2000/15). (Left: pre-contrast; right: specific substance D2 (150 μmol Fe/kg)).

FIG. 9: Frontal pre- and post-contrast MR tomograms of the pelvic region of the rabbit in the proton-density-weighted spin echo sequence (SE 2000/15). (Left: pre-contrast; right: parent compound C2 (150 μmol Fe/kg)).

Figure 10:
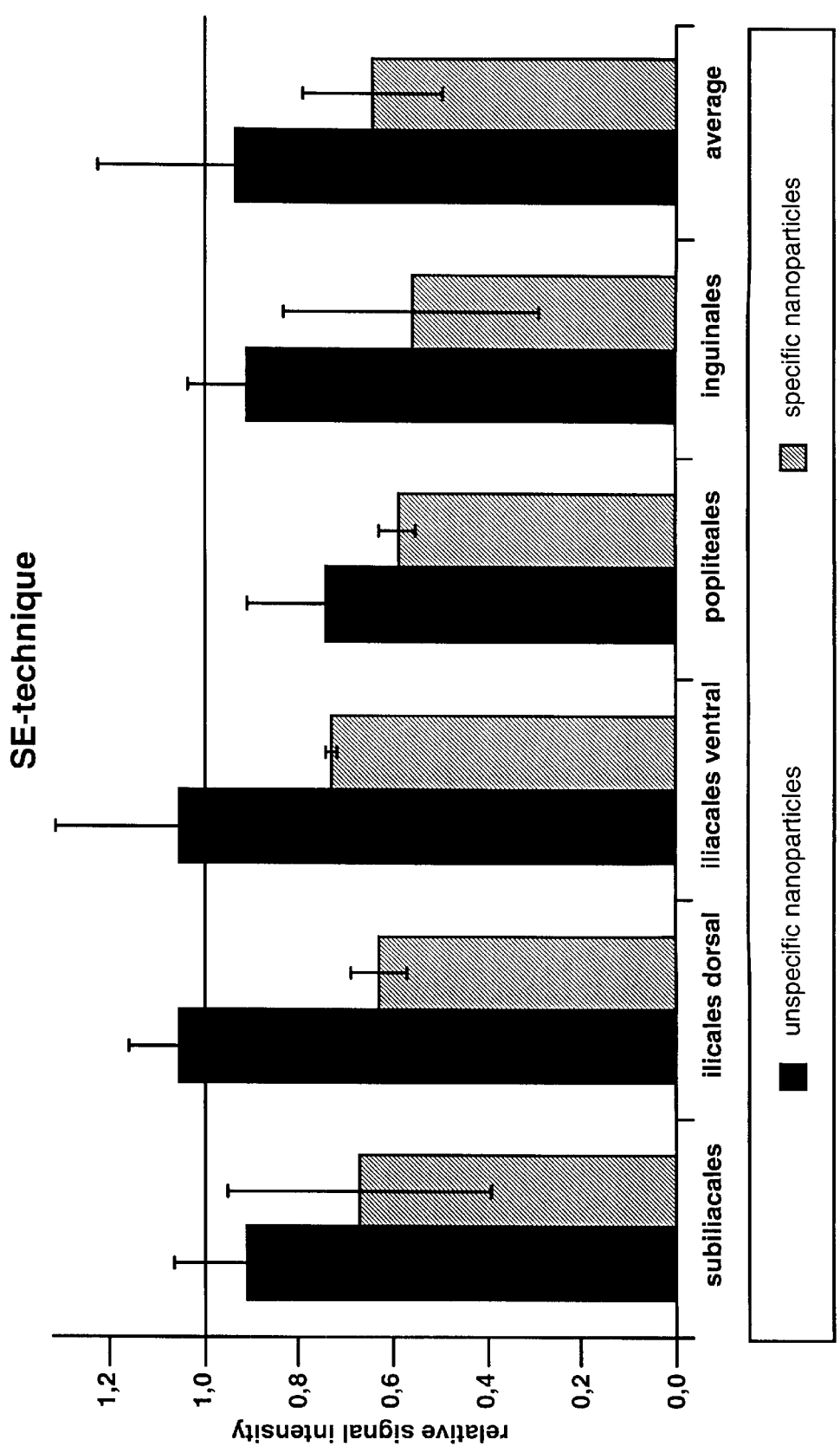
FIG. 10: Relative signal intensities for SE 2000/15 in various lymphatic nodes of the rabbit 24 h p.i.

FIG. 10: Specific nanoparticles vs. unspecific particles: Relative signal intensities for SE 2000/15 in various lymphatic nodes of the rabbit 24 h p.i. (150 μmol Fe/kg, n=3). (Quantitative evaluation according to FIGS. 8 and 9).

FIG. 11: Frontal pre- and post-contrast MR tomograms of the pelvic region of the rabbit in the T2*-weighted gradient echo sequence (GE 135/15/15°) (Left: pre-contrast; right: specific substance D2 (150 μmol Fe/kg)).

Figure 12:
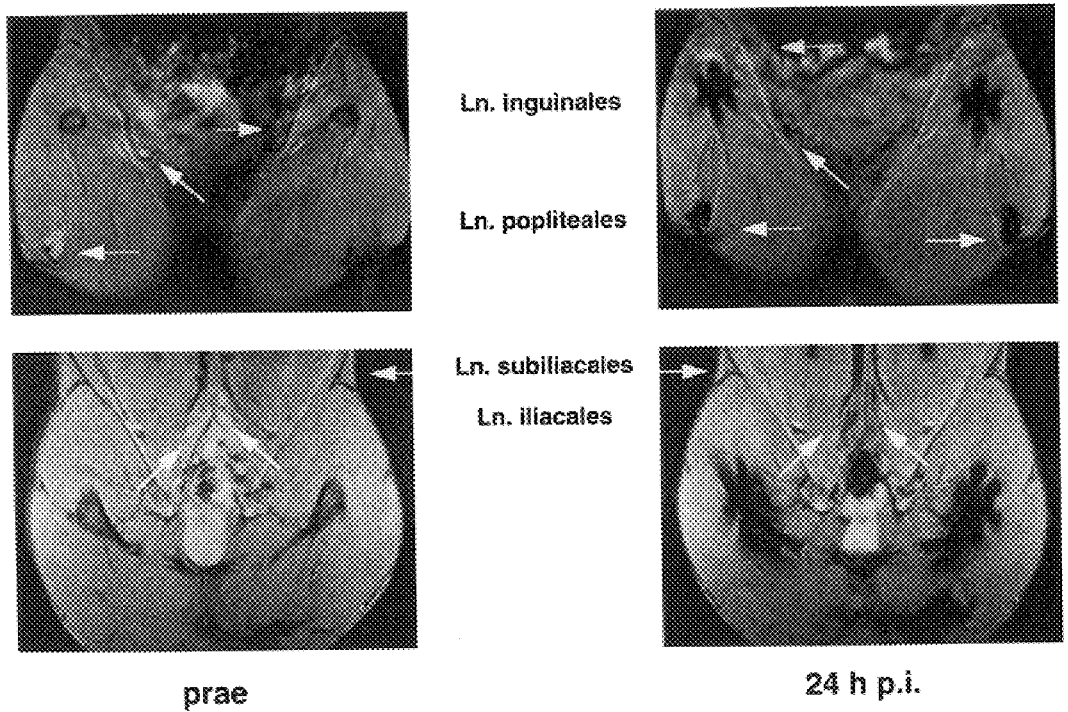
FIG. 12: Frontal pre- and post-contrast MR tomograms of the pelvic region of the rabbit in the T2*-weighted gradient echo sequence (GE 135/15/15°).

FIG. 12: Frontal pre- and post-contrast MR tomograms of the pelvic region of the rabbit in the T2*-weighted gradient echo sequence (GE 135/15/15°). (Left: pre-contrast; right: parent compound C2 (150 μmol Fe/kg)).

Figure 13:
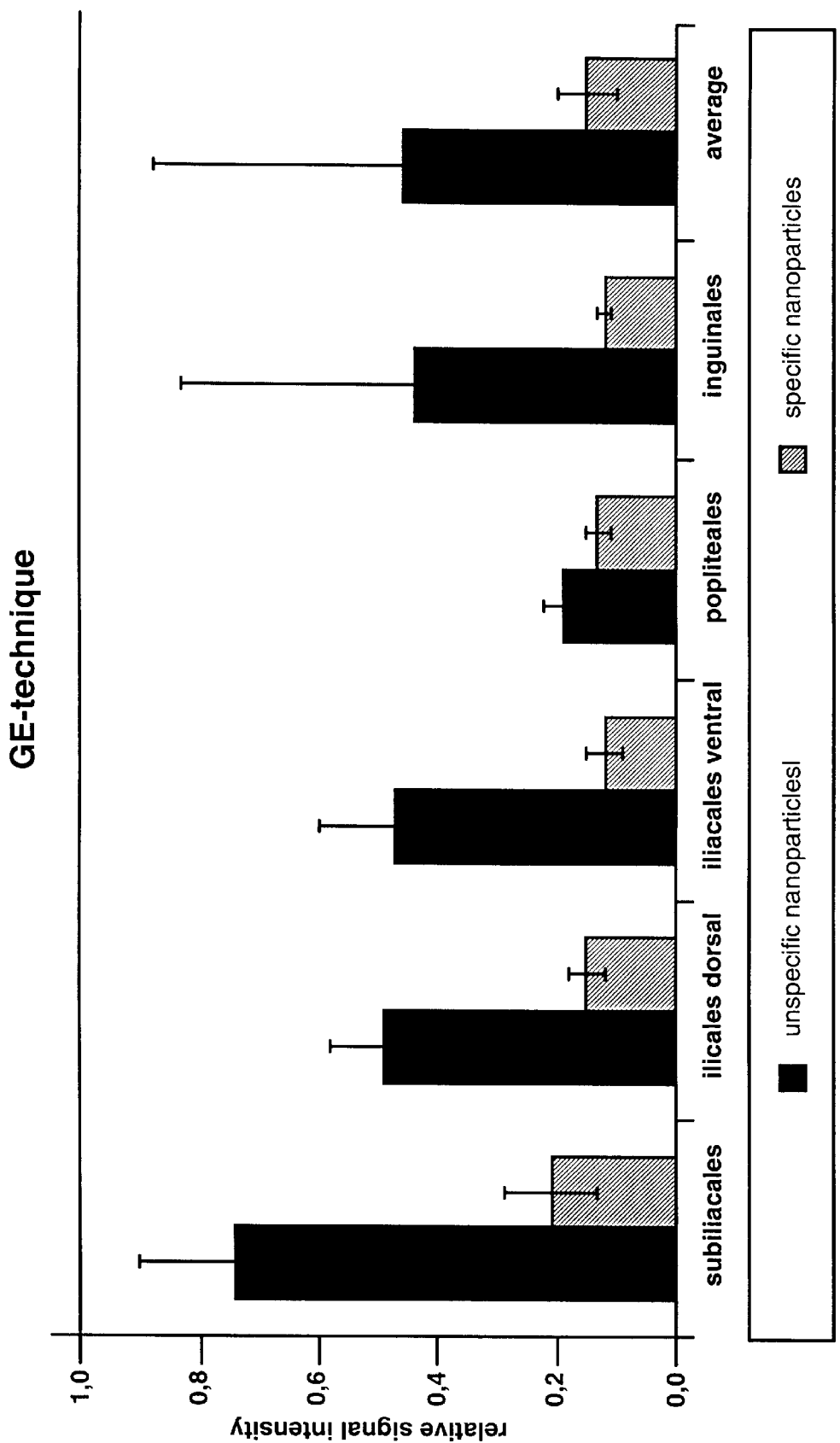
FIG. 13: Modified batch vs. original substance: relative signal intensities for GE 135/15/15° in various lymphatic nodes of the rabbit 24 h p. i.

FIG. 13: Specific nanoparticles vs. unspecific particles: relative signal intensities for GE 135/15/15° in various lymphatic nodes of the rabbit 24 h p.i. (150 μmol Fe/kg, n=3). (Quantitative evaluation according to FIGS. 11 and 12).

Figure 14:
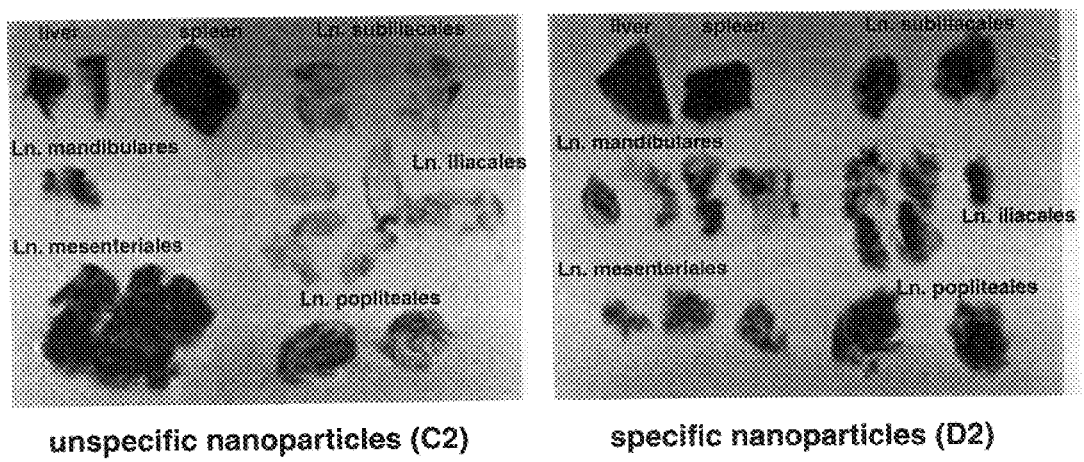
FIG. 14: Ex-vivo MR tomograms (GE sequence) of agarose-embedded lymphatic nodes of the rabbit

FIG. 14: Ex-vivo MR tomograms (GE sequence) of agarose-embedded lymphatic nodes of the rabbit; dose: 150 μmol Fe/kg; left: unspecific reference particles; right: specific nanoparticles.

Figure 15:
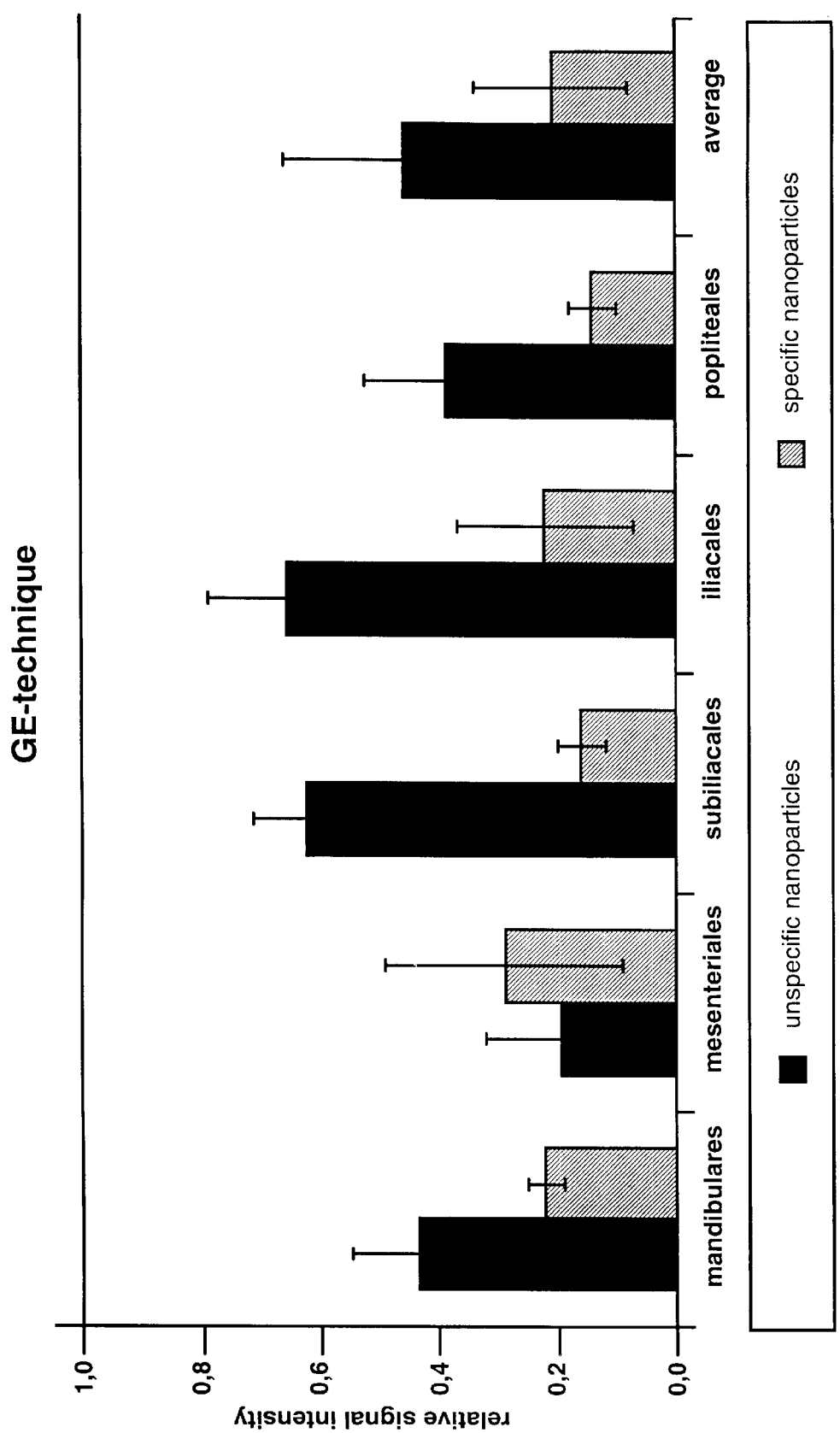
FIG. 15: Relative signal intensities for GE 135/15/15° in various lymphatic nodes of the rabbit 24 h p.i.

FIG. 15: Specific nanoparticles vs. unspecific particles: Relative signal intensities for GE 135/15/15° in various lymphatic nodes of the rabbit 24 h p.i. (150 μmol Fe/kg, n=3)

An analysis of interference with the relative lymphonodal signal intensity of the specific nanoparticles (FIGS. 8, 9=SE; FIGS. 11, 12=GE) demonstrates clearly that the modified substance is accumulated more homogeneously in the lymph nodes than the original substance. Lymphonodal signal reduction (GE sequence) of subiliac, iliac, popliteal lymph nodes as well as the mean accumulation throughout all the lymph node groups caused by the FP1-modified nanoparticles differs significantly (paired t-test, p<0.05) from the unmodified reference particles (FIG. 13). The more homogeneous interlymphonodal signal interference is clearly visible in the MR tomography images of agarose-embedded lymph nodes (FIG. 14); similar to what could be observed with rats, the reference substance shows strong signal reduction which is limited, however, to the mesenterial lymphatic nodes.

Application Example E3

Dependence of Lymphonodal Accumulation in the Rat on Dosage

Objective: Comparison of relative signal intensity in various lymphatic nodes/groups of lymphatic nodes between the parent compound (synthesis polymer=targeting polymer) and a modification produced according to the desorption-adsorption-method (synthesis polymer≠targeting polymer) as a function of the applied dose.

Substance: Specific nanoparticles (Example D2); comparison=basic structural unit according to Example C2 (=D2 without targeting polymer)

Dosage: 50–200 μmol Fe/kg body weight (body wt)(n=3 per dose)

Times: 24 h p. i. post injectionem)

MR method: MR tomography (SE and GE methods) (see Application Example E1)

Ex-vivo model: agarose phantom (see Application Example E1)

Figure 16:
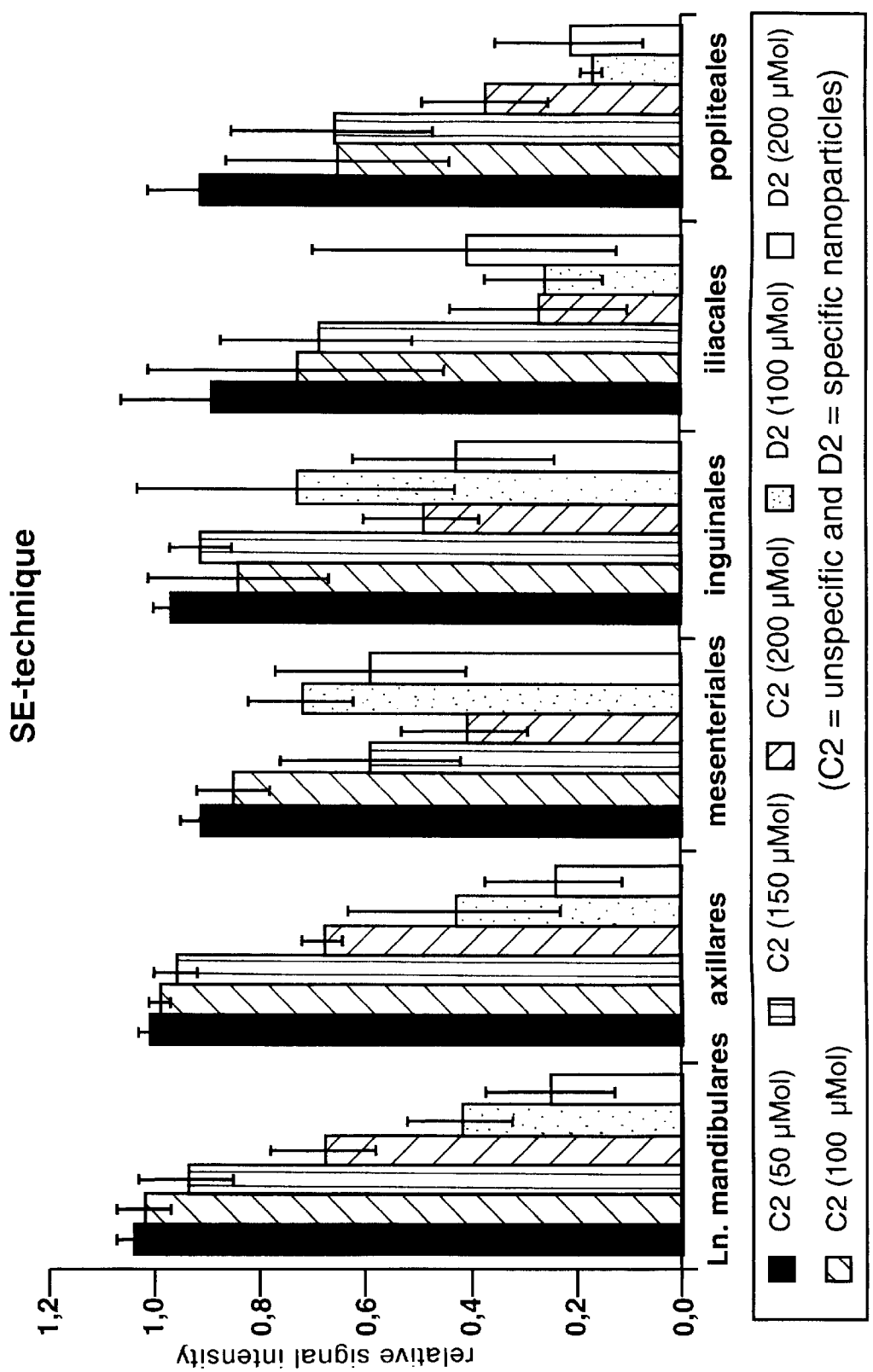
FIG. 16: Relative signal intensities for SE 2000/15 in various lymphatic nodes of the rat as a function of doses applied 24 h after injection of the nanoparticles.

Result:

FIG. 16: Specific nanoparticles according to Example D2 vs. unspecific particles: Relative signal intensities as a function of doses applied for SE 2000/15 in various lymphatic nodes of the rat 24 h after i. v. injection of the particles.

Figure 17:
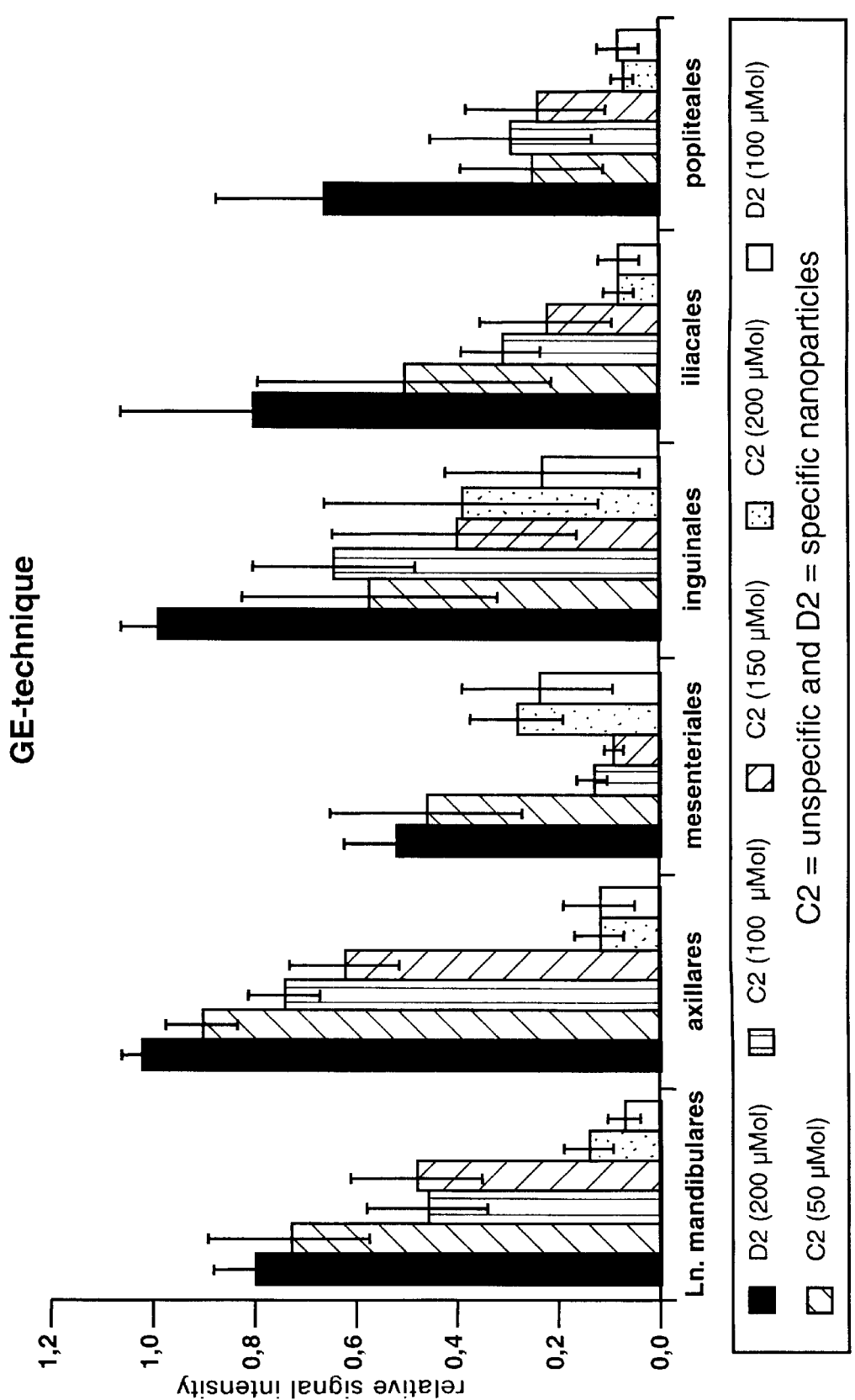
FIG. 17: Relative signal intensities as a function of the dose for GE 135/15/15° in various lymphatic nodes of the rat 24 h after application of the nanoparticles.

FIG. 17: Specific nanoparticles according to Example D2 vs. unspecific particles: Relative signal intensities as a function of doses applied for GE 135/15/15° in various lymphatic nodes of the rat 24 h after contrast media injection.

Significantly improved signal reduction (p<0.05) with the parent compound modified according to Example D2 is found for all lymph node groups except the mesenterial and inguinal lymph nodes at half the dose (200 μmol Fe/kg (C2) vs. 100 μmol Fe/kg (D2). These clear differences are also evident when a look is taken at the mean signal interference over all the lymph node stations (see Table 11).

TABLE 11

Mean relative signal intensities and standard deviation over all lymph node stations as a function of substance and dose applied.

| Sample | Dose | Mean relative signal intensity |
| --- | --- | --- |
| C2 | 100 μmol Fe/kg | 0.85 ± 0.13 |
| D2 | 100 μmol Fe/kg | 0.45 ± 0.23 |
| C2 | 200 μmol Fe/kg | 0.49 ± 0.17 |
| D2 | 200 μmol Fe/kg | 0.35 ± 0.15 |

Application Example E4

Time-dependence of Lymphonodal Accumulation in the Rat

Objective: Comparison of relative signal intensity in various lymphatic nodes/groups of lymphatic nodes between the parent compound (synthesis polymer=targeting polymer) and a modification produced according to the desorption-adsorption-method (synthesis polymer≠targeting polymer) as a function of time after application.

Substance: Specific nanoparticles (Example D2); comparison=basic structural unit according to Example C2 (=D2 without targeting polymer)

Figure 18:
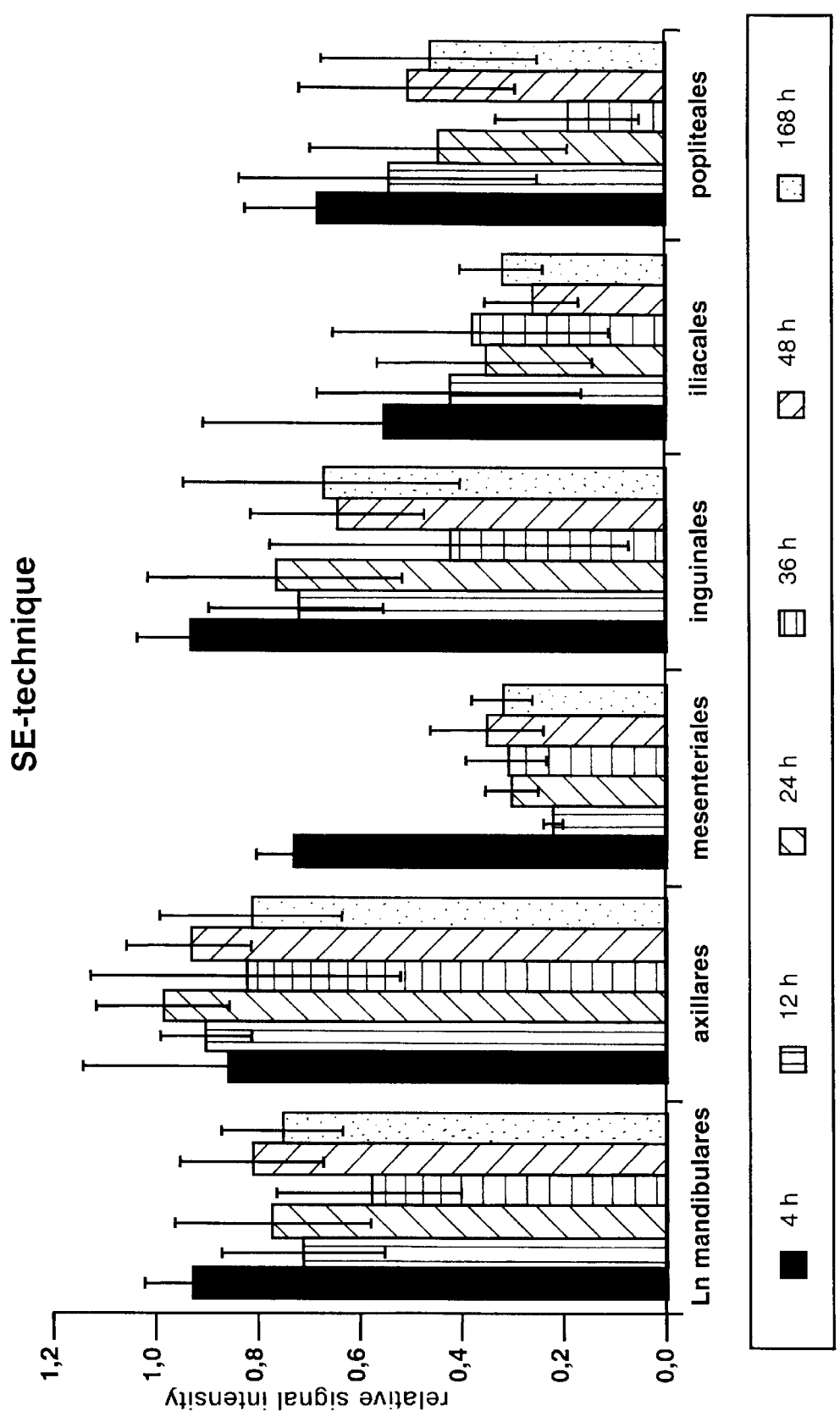
FIG. 18: Relative signal intensities for SE 2000/15 in various lymphatic nodes of the rat as a function of time after application (reference substance)

Dosage: 200 μmol Fe/kg body weight(n=3/timepoint)
Times: 4–168 h p. i. post injectionem)
MR method: MR tomography (SE and GE methods) (see Application Example E1)
Ex-vivo model: agarose phantom (see Application Example E1)
Result:

FIG. 18: Reference substance according to Example C2: Relative signal intensities for SE 2000/15 in various lymphatic nodes of the rat as a function of time after application.

Figure 19:
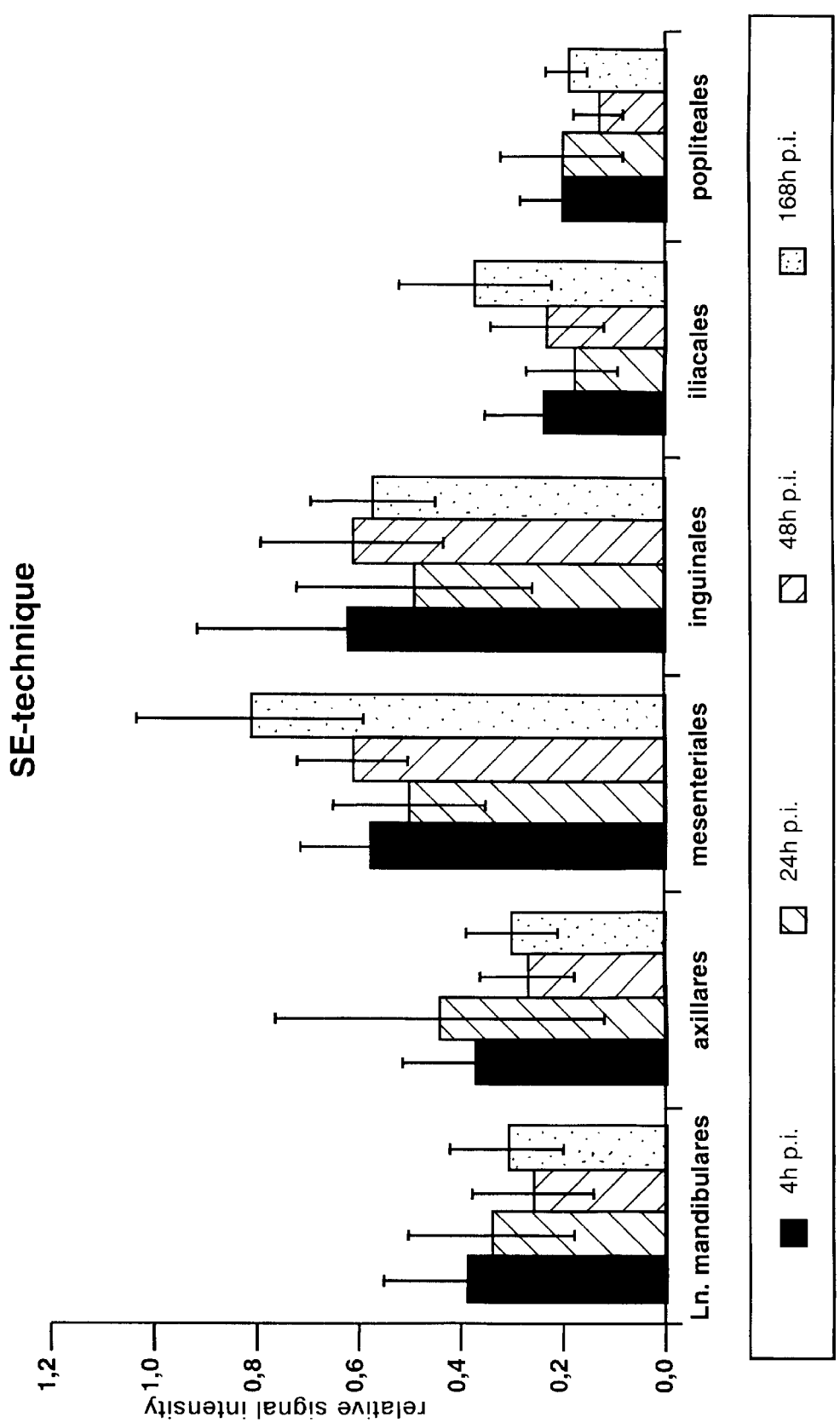
FIG. 19: Relative signal intensities for SE 2000/15 in various lymphatic nodes of the rat as a function of time after application of specific nanoparticles.

FIG. 19: Specific nanoparticles according to Example D2: Relative signal intensities for SE 2000/15 in various lymphatic nodes of the rat as a function of time after application.

Figure 20:
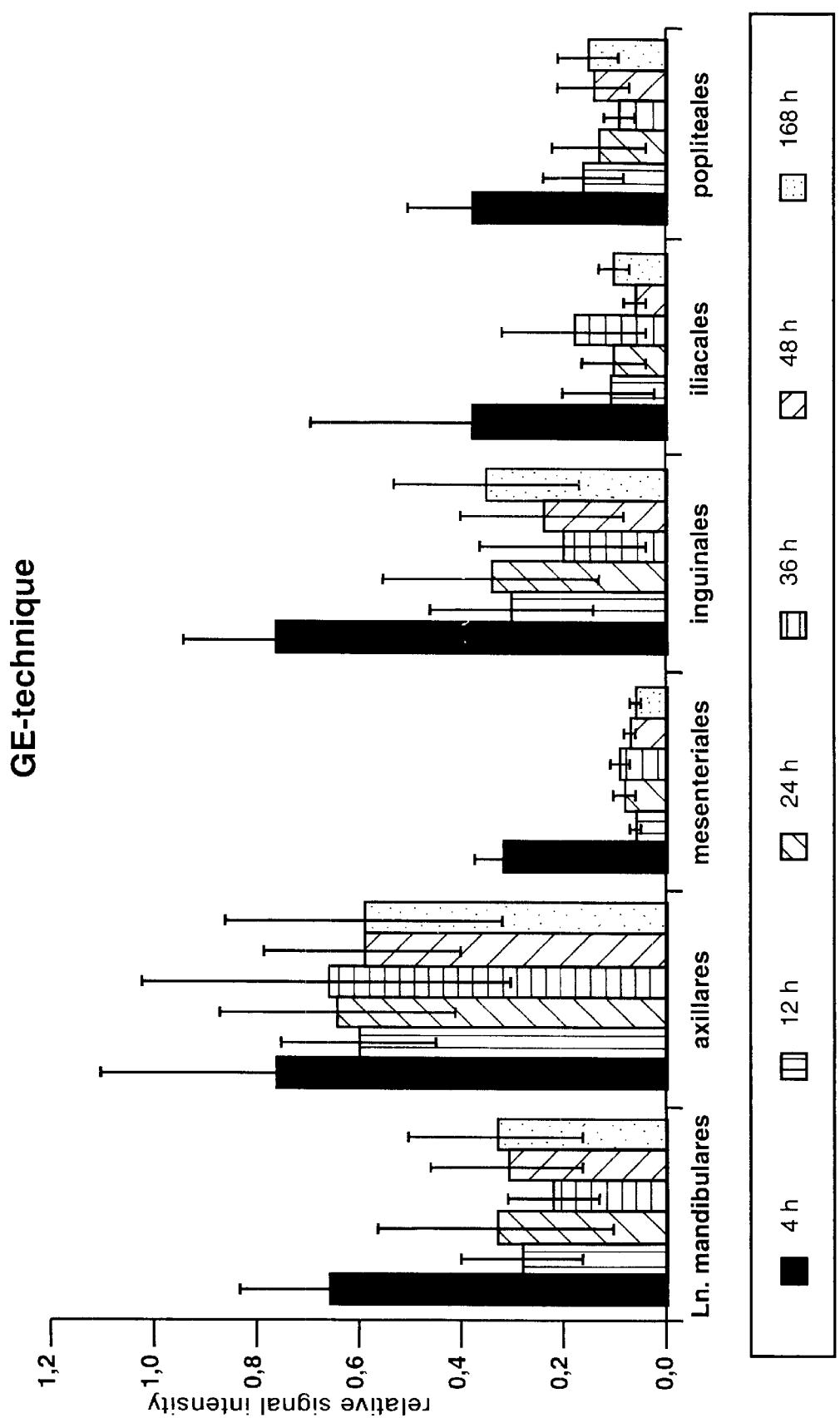
FIG. 20: Relative signal intensities for GE 135/15/15° in various lymphatic nodes of the rat as a function of time after application (reference substance)

FIG. 20: Reference substance according to Example C2: Relative signal intensities for GE 135/15/15° in various lymphatic nodes of the rat as a function of time after application.

Figure 21:
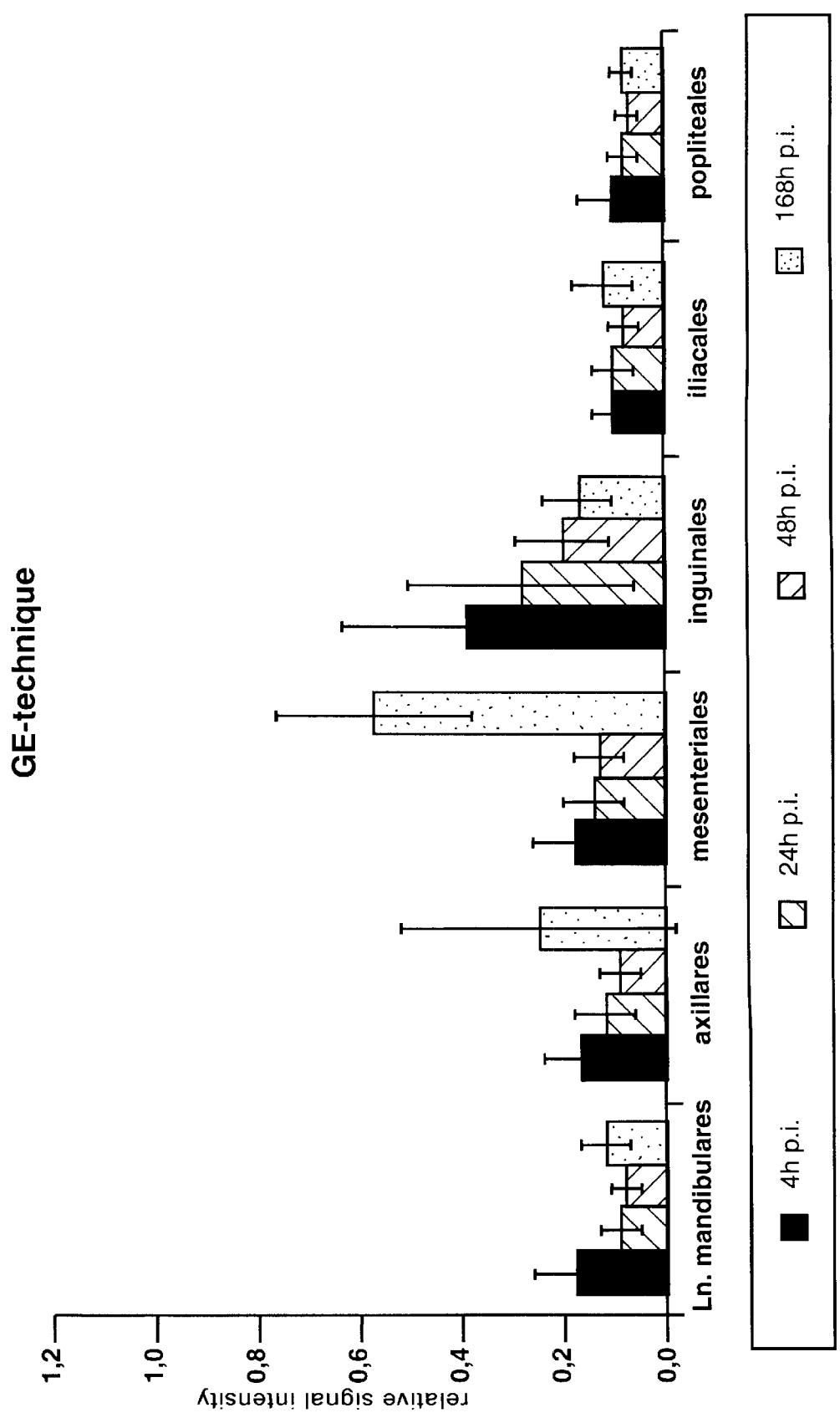
FIG. 21: Relative signal intensities for GE 135/15/15° in various lymphatic nodes of the rat as a function of time after application of specific nanoparticles.

FIG. 21: Specific nanoparticles according to Example D2: Relative signal intensities for GE 135/15/15° in various lymphatic nodes of the rat as a function of time after application.

The time-dependent MR tomographic studies on lymphonodal signal reduction after intravenous application of the substances clearly show that the non-specific parent substance causes poorer signal reduction in the lymph nodes than the specific modification according to Example D2.

Application Example E5

Combination with Physiotherapeutic Measures: Temperature

Objective: Comparison of relative signal intensity in various lymphatic nodes/groups of lymphatic nodes as a function of body temperature regulated by a thermobath.

Substance: Specific nanoparticles (Example D2);
Dosage: 100 μmol Fe/kg body weight (n=7/group)
Times: 24 h p. i. post injectionem)
Method: MR tomography (SE and GE methods)
Hyperthermic model:
Application of Heat To study the influence of heat on the accumulation of the contrast medium in various lymph node groups, the rats were anaesthetized for 3–4 h, and then placed partially in a water bath for 2 h. The left side of the rats' body lay on a heater plate and the right side of their body lay on a synthetic insulating plate of the same height that was not heated. This arrangement caused a difference in temperature of the water on the left and right side of the rats' bodies. Water temperature under the left shoulder of the rats initially was 41.0–41.5° C., reaching a constant value of 41.5–42.0° C. after 30 min. Water temperature under the left shoulder of the rats initially was 37.0–37.5° C., reaching a constant value of 37.5–38.0° C. after 30 min. After a period of 30 minutes in the water bath, the rats were i.v. injected (bolus) with a dose of 100 μmol Fe/kg body wt of nanoparticles. After remaining in the water bath at constant temperatures for another 1.5 h, the rats are put back into their cage, the lymph nodes are prepared 24 h after the injection and examined using MR tomography.

Figure 22:
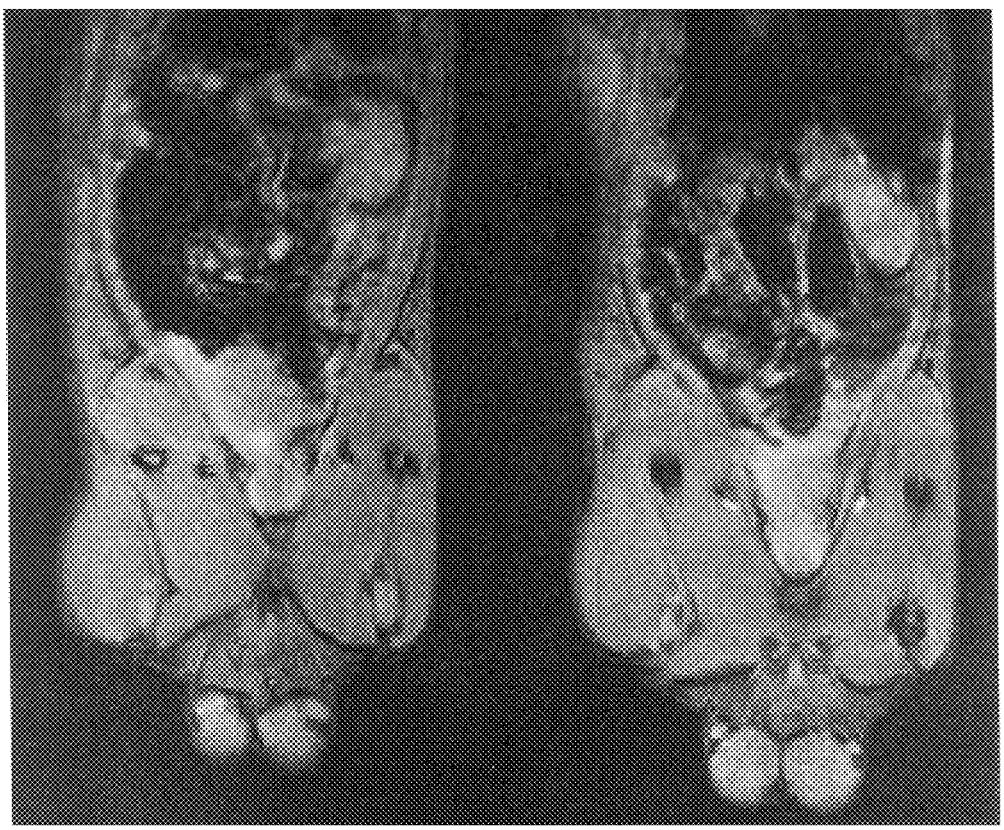
FIG. 22: Effect on accumulation in lymphatic nodes caused by the input of heat.

Result:

FIG. 22: Influence on accumulation in the lymphatic nodes exerted by purposeful application of heat. The popliteal lymph nodes can only be guessed as being the bright spots in the pre-contrast picture on the left. The figure on the right impressively demonstrates the influence of heat treatment. The left side of the anaesthetized rat lay on an insulating synthetic plate and had a normal body temperature while the right side was heated in a water bath to 41.5–42.0° C. The "cold" side shows little or no accumulation, while the heated side shows high and homogeneous intralymphonodal accumulation of nanoparticles. (Nanoparticles according to Example D2; 100 μmol/kg body wt; 24 h p. i.; GE 135/15/15)

The in-vivo tomogram (FIG. 22) clearly shows the effects of heat treatment. While the cold, unheated left side of the rat's body shows no visible accumulation in the popliteal lymph nodes, the heated right side shows a high and homogeneous signal reduction (accumulation) in the popliteal lymph nodes examined.

The rats were anaesthetized and put into the thermal bath to show the effects of heating particularly clearly. Anaesthesia causes a standstill of peripheral muscular activity, diminished lymphatic flux and reduced vascular permeability. As a result, virtually no accumulation of nanoparticles can be detected without heating.

Application Example E1

Figure 23:
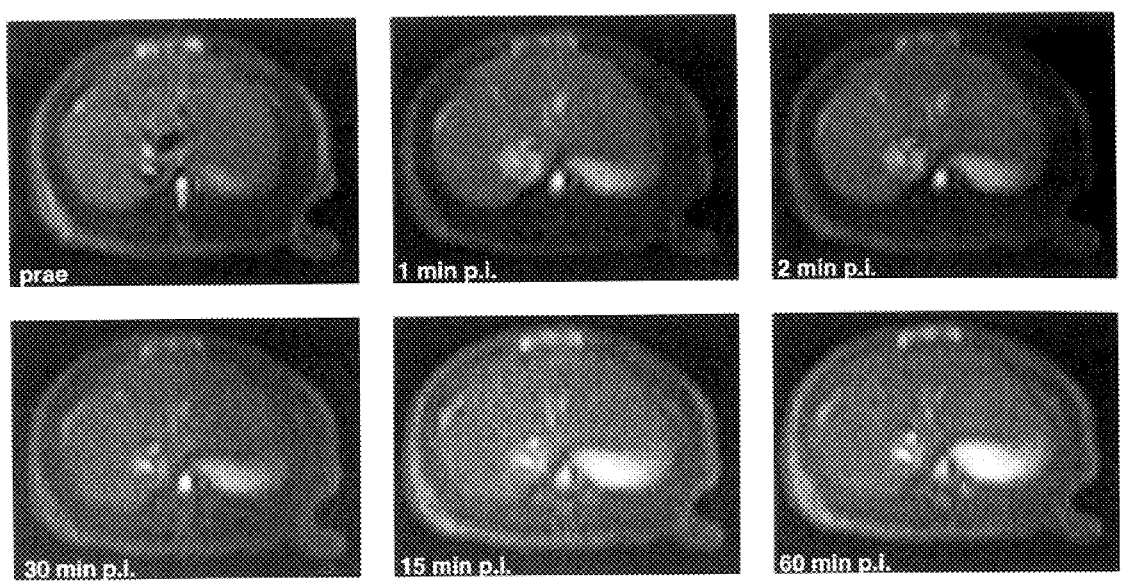
FIG. 23 Transversal dynamics study of the rat's abdomen using a T1-weighted SE sequence (TR: 200 ms, TE: 10 ms) after bolus injection of the specific nanoparticles according to Example D2 (dose: 20 µmol Fe/kg)

MR Angiography
Substance: Specific nanoparticles (Example D2)
Animals: rat (see Example of Application E1)
Dosage: 20 μmol Fe/kg i.v.
Time: 0–2 h p. i.
MR equipment:
Device: Siemens Magnetom 1.5 T MR whole-body tomograph with extremity coil
MR parameters: transversal dynamic study using a T1-weighted SE sequence (TR: 200 ms, TE: 10 ms), FOV 170 mm, matrix 256×256; SD: 3 mm;
coronary MIPS from 3D flash (TR: 40 (60) ms, TE: 6 ms, FA 60 (40)°) and 3D FISP sequence (TR: 40 ms, TE: 7 ms, FA 35°) FOV 240 mm, matrix 256×256; SD: 17 mm;
MR evaluation: signal intensities in user-defined regions of interest in vessels (caval vein), the liver, fat and muscles. The signal intensities are standardized with respect to the background Results:

FIG. 23 : Transversal dynamic study of the rat's abdomen using a T1-weighted SE sequence (TR: 200 Ms, TE: 10 ms) after bolus injection of the specific nanoparticles according to Example D2 (dose: 20 μmol Fe/kg); clear signal enhancement (1 min. p.i.) in the intrahepatic vessels and the caval vein).

Figure 24:
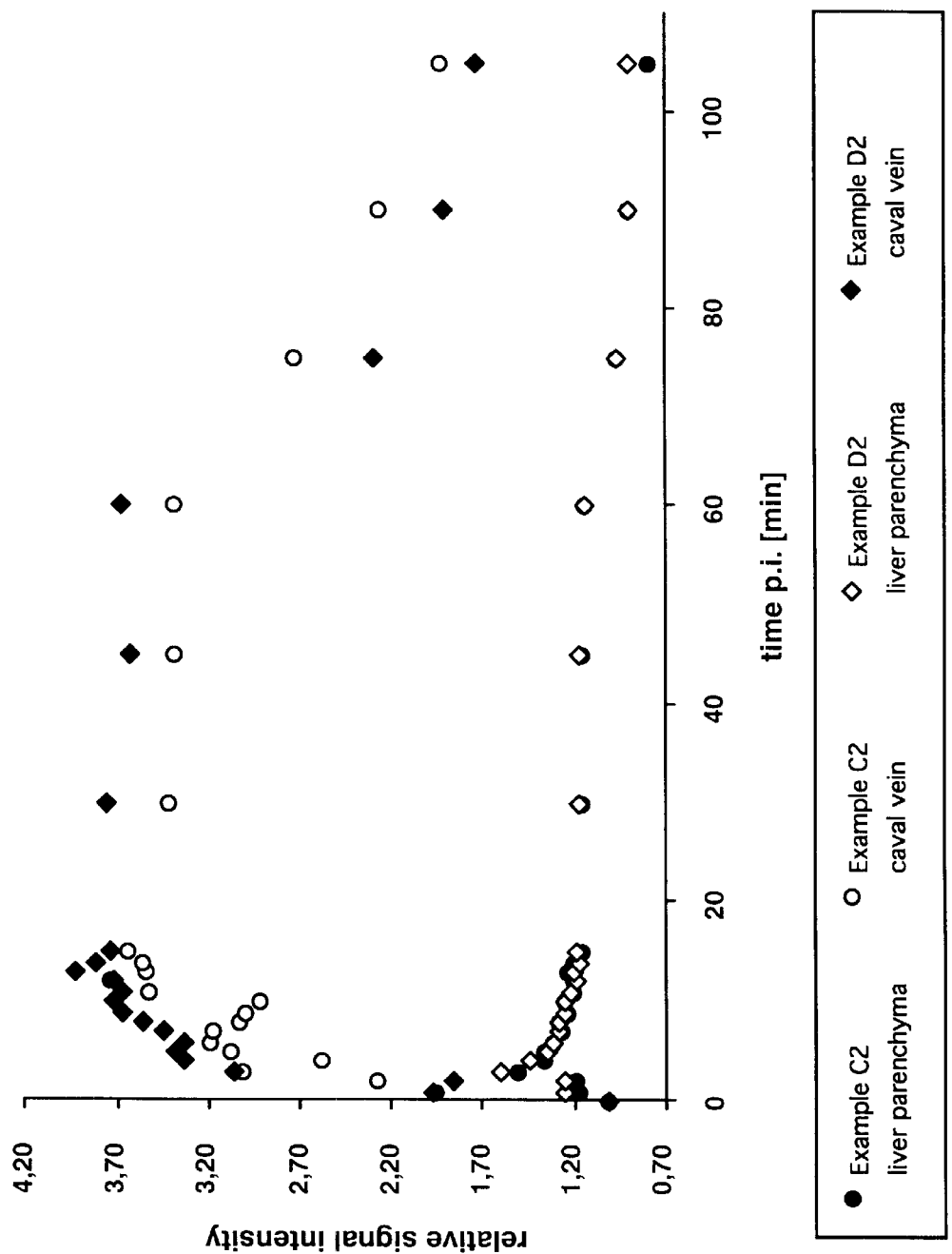
FIG. 24: Comparison of relative signal intensities for SE TR/TE 200 ms/10 ms in the venous vessel and the liver parenchyma for the specific nanoparticles according to Example D2 and the unspecific reference substance according to Example C2

FIG. 24: Comparison of relative signal intensities for SE TR/TE 200 ms/10 ms in the venous vessel and the liver parenchyma for the specific nanoparticles according to Example D2 and the unspecific reference substance according to Example C2; dose 20 μmol Fe/kg.

Figure 25:
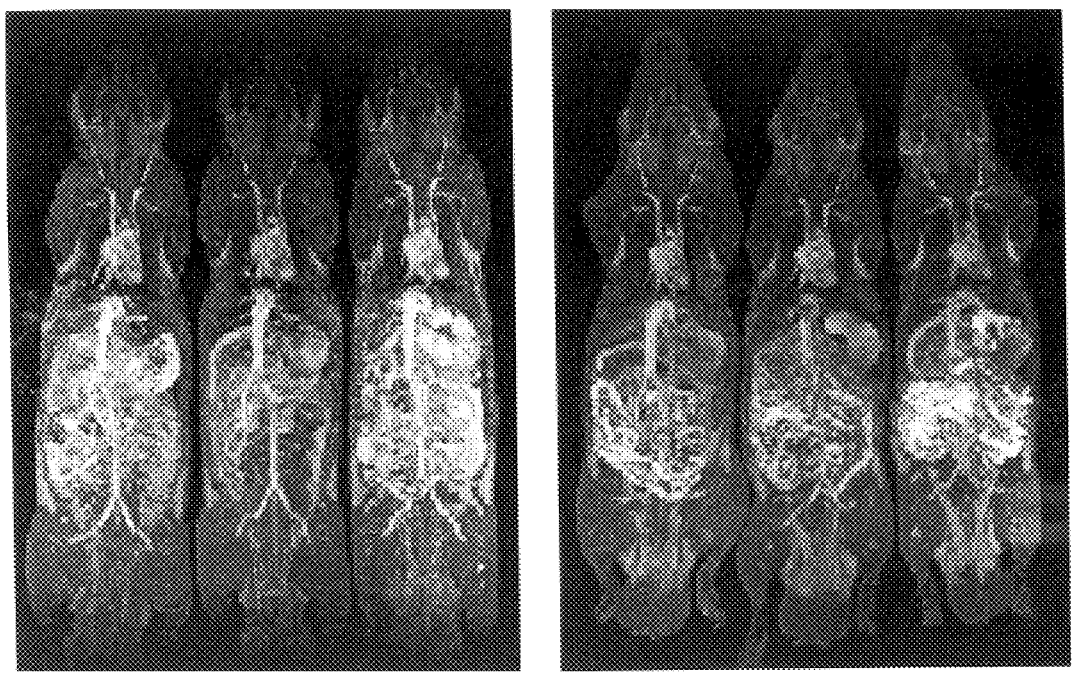
FIG. 25: Coronary MIPS (maximum-intensity projections) of 3D flash tomograms (TR: 40 ms, TE: 6 ms, FA 60°) for the specific nanoparticles according to Example D2 and the reference substance C2

FIG. 25: Coronary MIPS (maximum-intensity projections) of 3D FLASH tomograms (TR: 40 ms, TE: 6 ms, FA 60°); comparison of the specific nanoparticles according to Example D2 (left) and the reference substance C2 (right); dose 20 μmol Fe/kg.

FIGS. 23 and 25 clearly show the advantages of the specific nanoparticles (according to Example D2) as compared with the parent substance according to Example C2. The summary graph of the signal's time history (FIG. 24) in the caval vein or in the liver parenchyma demonstrates the excellent properties of the specific nanoparticles for use as contrast media in MR angiography. Enhancement is three times higher than with the reference substance, and the brightening effect lasts for a long time and is very constant (diagnostic time window>60 min.).

Application Example E7

Visualization of Lymph Nodes in the Healthy Rat and the Tumor-carrying Rabbit

Objective: Proof of suitability of the nanoparticles according to the invention for use as a visual labeling substance in surgical medicine.

Substance: specific nanoparticles (Example D2)

Animals: rat, SPF Han-Wistar; ca. 150 g Russian rabbit (Chbb: HM, Thomae GmbH) with an implanted VX2 tumor (tumor bank of Deutsches Krebsforschungszentrum, Heidelberg); ca. 2.6 kg. The tumor was implanted by injecting $3 \times 10^6$ living tumor cells in the caudolateral femoral muscles. Uptake takes place 20 days after implantation.

Dosage: rat: intravenous injection of 500 μmol Fe/kg body weight rabbit: interstitial application of 20 μmol per paw Times: rat: 1, 4 and 24 h p. i. rabbit: 12 h p. i.

Results

Figure 26:
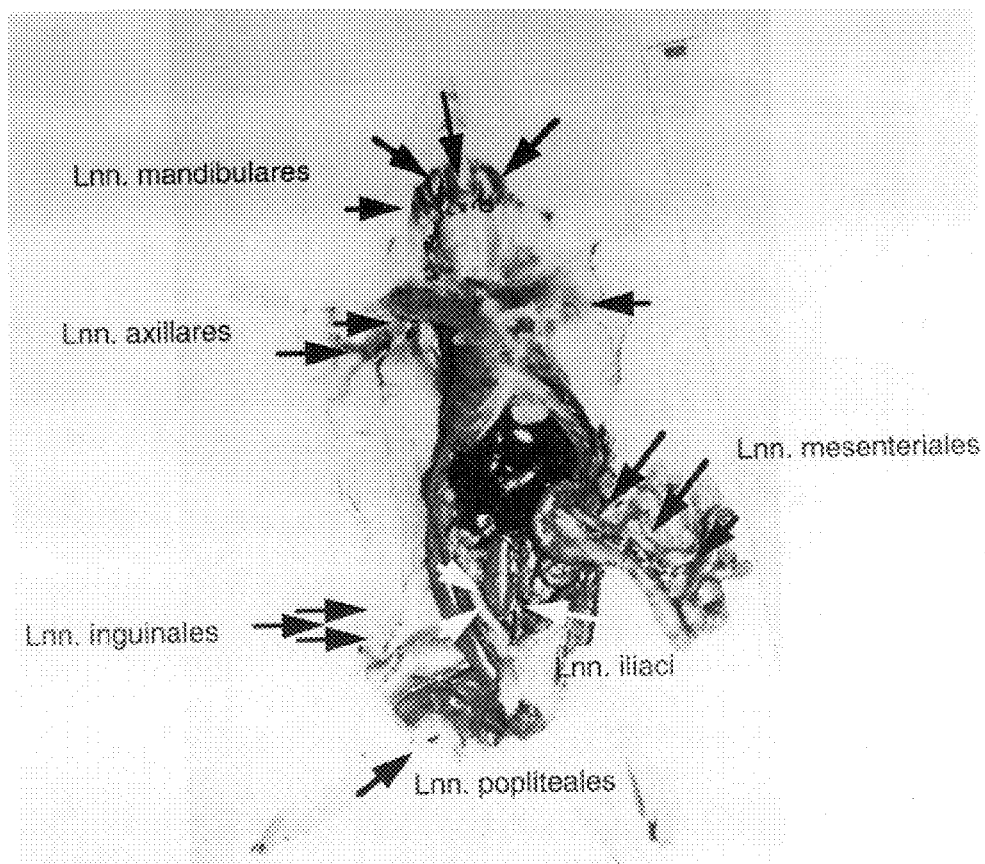
FIG. 26: Nanoparticles according to the invention as "intraoperative" labeling substances for visual detection of lymphatic nodes (general view)

FIG. 26: Nanoparticles according to the invention as "intraoperative" labeling substances for visual detection of lymphatic nodes (general view)

Figure 27:
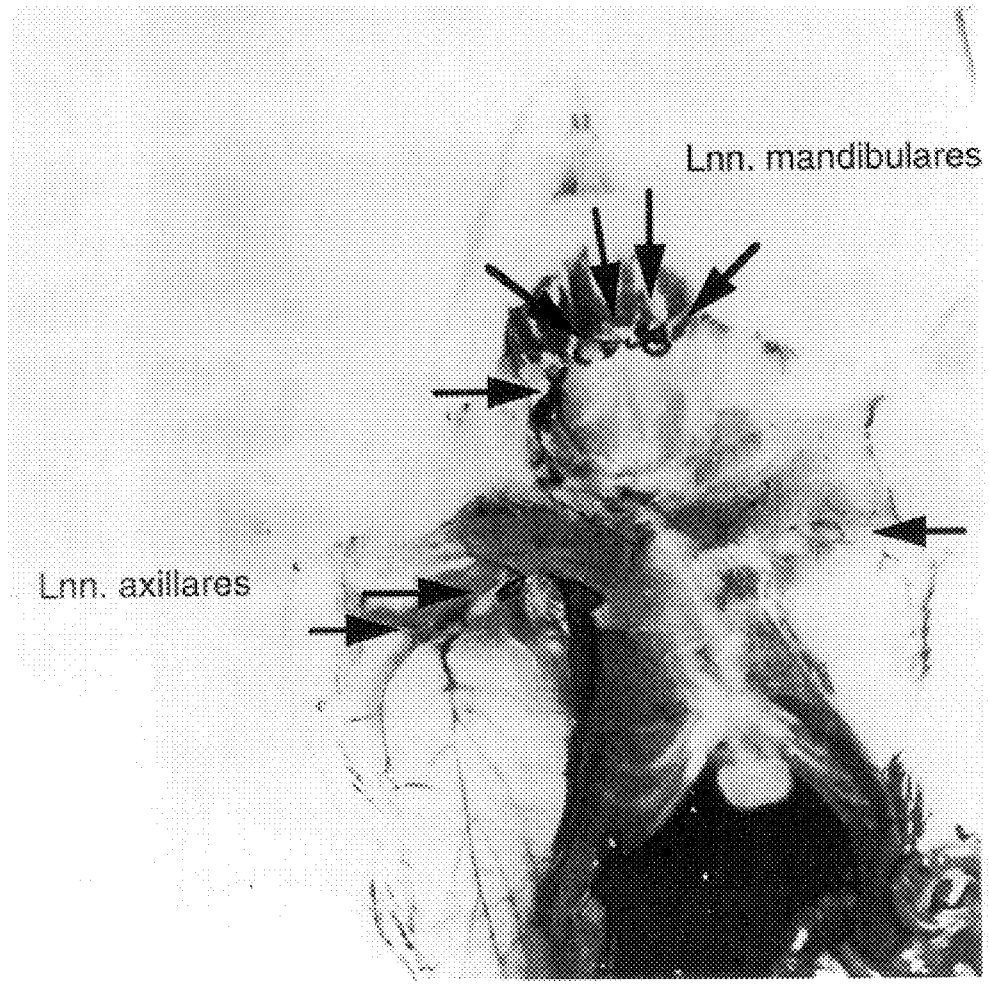
FIG. 27: Nanoparticles according to the invention as "intraoperative" labeling substances for visual detection of lymphatic nodes (detailed view).

FIG. 27: Nanoparticles according to the invention as "intraoperative" labeling substances for visual detection of lymphatic nodes (detailed view).

Figure 28:
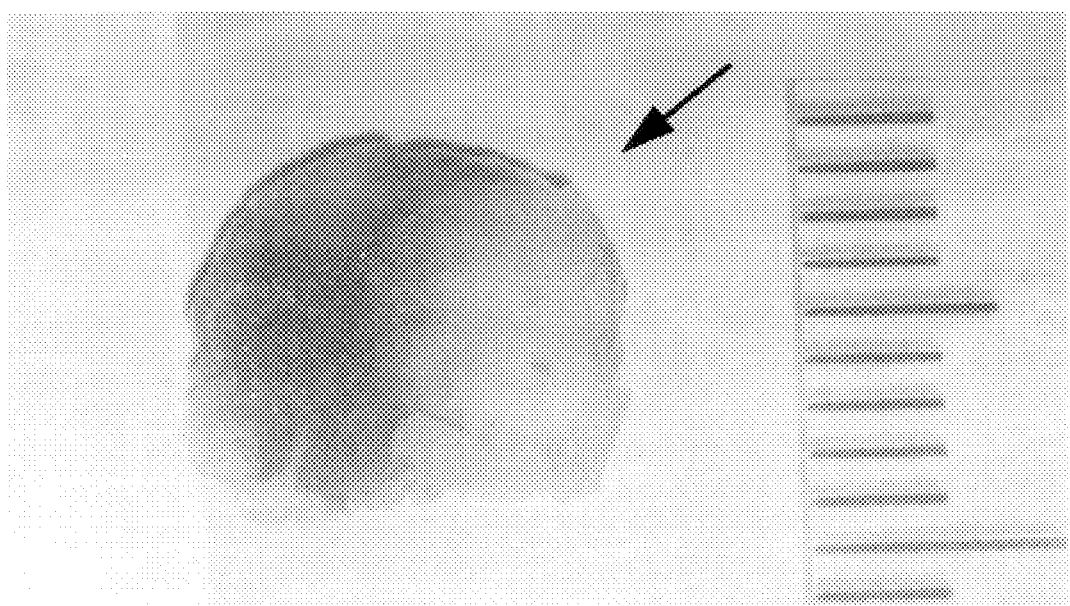
FIG. 28: Demonstration of metastases in lymphatic nodes by visual detection in metastatic lymphatic nodes in the rabbit.

FIG. 28: Demonstration of metastases in lymphatic nodes by visual detection in metastatic lymphatic nodes in the rabbit. The metastases can be identified as bright recesses in the lymphatic nodes that are otherwise shown in dark coloring.

The images of the rats (FIGS. 26 and 27) show that a great number of the most varied lymph nodes/lymph node groups can be stained by a single intravenous application of the nanoparticle solution. The lymphatic nodes are clearly distinguishable from the surrounding tissue and can thus be easily detected for removal, if required, by the operating surgeon.

The studies of VX2 tumor-carrying rabbits demonstrate that lymph nodes in the tributary area are homogeneously stained by the specific nanoparticles after interstitial application, and that small metastases can be distinguished visually as bright recesses in the darkly stained healthy lymphonodal tissue (FIG. 28).

Application Example E8

Cell Experiment to Prove the Specificity of the Nanoparticles

Objective: Proof of the specific cellular uptake (receptor-mediated endocytosis) of nanoparticles having a secondary coat of transferrin (targeting polymer)

Substance: specific nanoparticles (Example D6)

Comparison: basic substance according to Example C1 (D6 without transferrin)

Concentration: 0.5 mmol Fe/l medium

Times: 18 h incubation at 37° C.; 5% $CO_2$–95% air

Cell culture:

Uptake by Human Myeloma Cells

Human myeloma cells (ATCC CRL 9068; cell line NCI 929) are cultivated at a concentration of at least $1 \times 10^6$ cells/ml in RPMI 1640 10% FCS (fetal calf serum) and 0.05 mmol/L of 2-mercaptoethanol (37° C., 5% carbon dioxide; 225 $cm^2$ culture flasks).

When the cells have reached a concentration of ca. $1.5 \times 10^6$ cells/ml they are centrifuged and resuspended in fresh medium.

The cells are incubated with the nanoparticles at a concentration of 0.5 mmol/l (calculated in terms of iron) for 18 hours.

The cells are pelleted, and washed twice with PBS. Then the cell number is determined in an aliquot (Neubauer counting chamber). The cell pellet is dissolved by heating in 500 μl conc. nitric acid/100 μl hydrogen peroxide and filled to a volume of 5.0 ml. Then the iron concentration is determined using atomic emission spectroscopy (AES, detection limit 0.1 ppm).

Results

Figure 29:
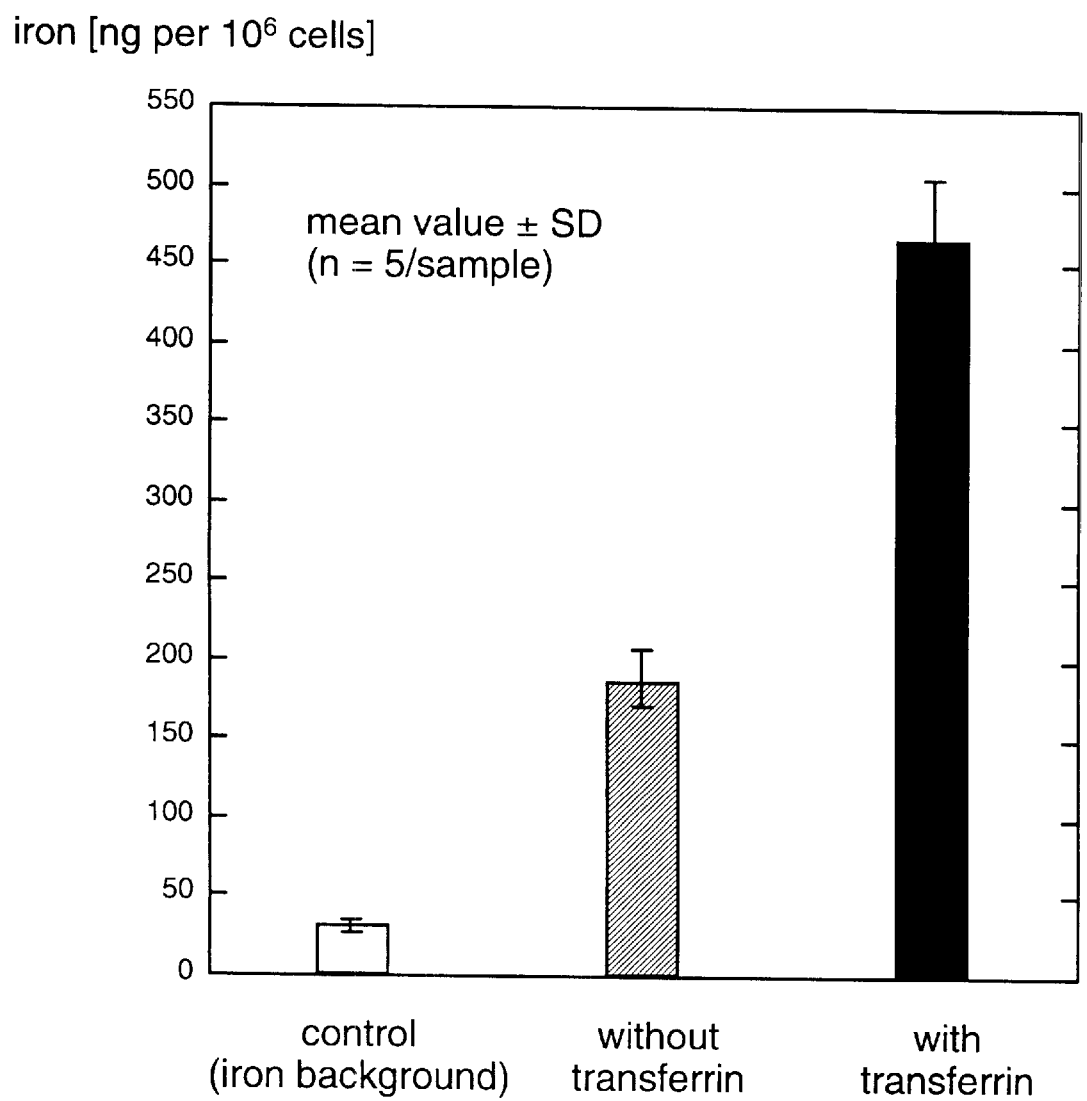
FIG. 29: Cell tomogram of specific nanoparticles (with transferrin) compared with the unspecific reference (nanoparticles without transferrin).

FIG. 29: Cell tomogram of specific nanoparticles (with transferrin) compared with the unspecific reference (nanoparticles without transferrin) The NCI cells (human myeloma cell line) accumulate nearly twice as many specific particles as reference particles.

The specific nanoparticles are clearly taken up to a greater extent by the NCI 929 myeloma cells. The advantages of the specific nanoparticle design according to the invention are demonstrated by the fact that 50% fewer nanoparticles without a targeting polymer are taken up.

Application Example E9

Atherosclerosis Imaging in the Watanabe Rabbit (Plaque Visualization)

Objective: Visualization of atherosclerotic plaques in the rabbit using nanoparticles to which a peptide with an affinity for plaque was applied according to the desorption-adsorption method (secondary coat, targeting polymer).

Substance: specific nanoparticles (Example D7)

Dosage: 200 μmol Fe/kg body weight (body wt)

Time: 5 h p. i. (post injectionem)

MR method:

Device: Siemens Magnetom 1.5 T MR whole-body tomograph with extremity coil

MR parameters: Field of view (FOV)=150 mm, matrix= 256×256; slice thickness=3 mm orientation of sections= frontal Sequence 1: Proton-density-weighted spin echo sequence (SE) with TR=2000 ms and TE=15 ms Sequence 2: T2-weighted gradient echo sequence (GE) with TR=135 ms and TE=15 ms; FA=15°

Ex-vivo model: agarose phantom (see Application Example E1) The aorta was excised, carefully cut open and rinsed with cold PBS solution to remove unbound nanoparticles or those nanoparticles which were not taken up. Then the aorta is bisected, poured in the agarose phantom and examined using MR tomography.

Histology: Prussian blue staining

Figure 30:
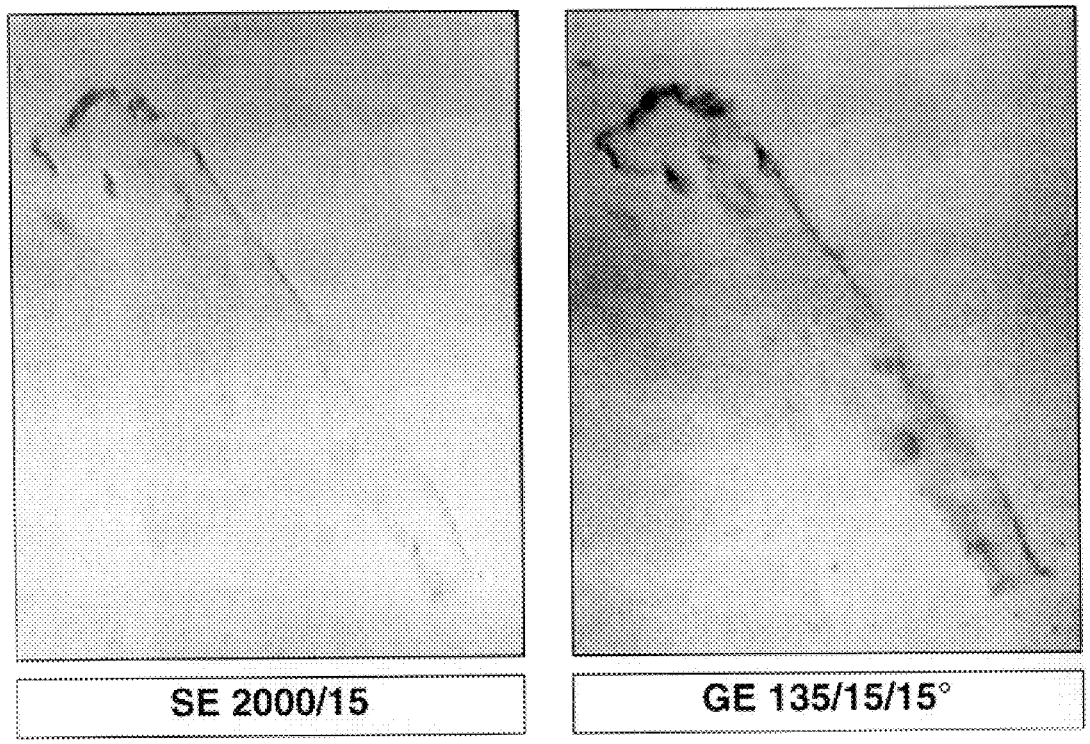
FIG. 30: Ex-vivo MR tomographic diagram of atherosclerotic plaques of the aorta of a rabbit with modification D7 (dose 200 µmol Fe/kg; aorta resection 5 h p.i.)

Results:

FIG. 30: Ex-vivo MR tomographic diagram of atherosclerotic plaques of the aorta of a rabbit with modification D7 (dose 200 μmol Fe/kg; aorta resection 5 h p.i.); left: proton-density-weighted spin echo sequence; right: $T2^*$-weighted gradient echo sequence.

Figure 31:
FIG. 31: Histological detection of iron in the atherosclerotic membrane of a rabbit's aorta with Prussian blue staining.

FIG. 31: Histological detection of iron in the atherosclerotic membrane of a rabbit's aorta with Prussian blue staining. A comparison with the MR tomogram (GE 135/ 15/15°) shows that the histologically detected iron is located at sites that show a clear signal reduction in the image due to accumulation of the specific nanoparticles. The aorta was resected 5 h after intravenous administration of 200 μmol Fe/kg of the specific particles according to D7.

FIG. 32: Histochemical detection (Prussian blue staining) of accumulated nanoparticles according to Example E6 in the aorta of a Watanabe rabbit. The upper part of the figure gives a general view of the prepared aorta on the agar, the lower part illustrates the good correlation of the iron staining (blue granules) and the visually detectable plaques in the aortic arch, which is changed to a particularly great extent.

The MR tomogram ("ex-vivo tomogram") of the prepared aorta depicts the plaques as dark spots (signal reduction).

The histological proof by means of Prussian blue staining (iron), when compared with the MR tomogram (GE 135/15/15°), shows that the iron detected is located at sites for which the image shows a clearly reduced signal due to nanoparticle accumulation. The findings of the MR tomogram correlate with the plaques that are clearly visible. The most extensive plaques are located in the aortic arch, which is confirmed by the MR tomogram and the histological view; smaller plaques are also well-detectable both in the MR tomogram and the histological picture.

Application Example E10

Accumulation in Tumors Studied in Tumor-carrying Mice

Objective: Proof was to be provided that nanoparticles can accumulate in tumors. The tests are to show, on the one hand, that the particles are suitable vehicles for chemotherapeutic agents, and on the other, that the nanoparticles can help to check whether the therapeutic agents have reached their desired place of action, i.e. the tumor, so that this is a combination of diagnostic and therapeutic applications.

Substance: specific nanoparticles (Example D2)

Animals: Swiss nude mice with an implanted tumor (n=5/dose) (LS 174T, s.c.: application 10 days prior to the experiment)

Anaesthesia: Rompun/Ketavet (1:1), ca. 0.5 ml per kg body weight i.m.

Dosage: 200 μmol Fe/kg body weight (body wt)

Times: 0–120 minutes and 12 or 24 hours after application

MR method:

Device: Siemens Magnetom 1.5 T MR whole-body tomograph with extremity coil

MR parameters: Field of view (FOV)=150 mm, matrix=256×256; slice thickness=3 mm orientation of sections=frontal Sequence 1: Proton-density-weighted spin echo sequence (SE) with TR=2000 ms and TE=15 ms Sequence 2: Dynamic study: SE sequence with TR/TE=300 ms/15 ms MR evaluation: signal intensities in user-defined regions of interest in tumor, muscle, fat and background. The relative signal intensities in the various tissues are standardized and refer to the signal intensity in fat.

Results

Figure 33:
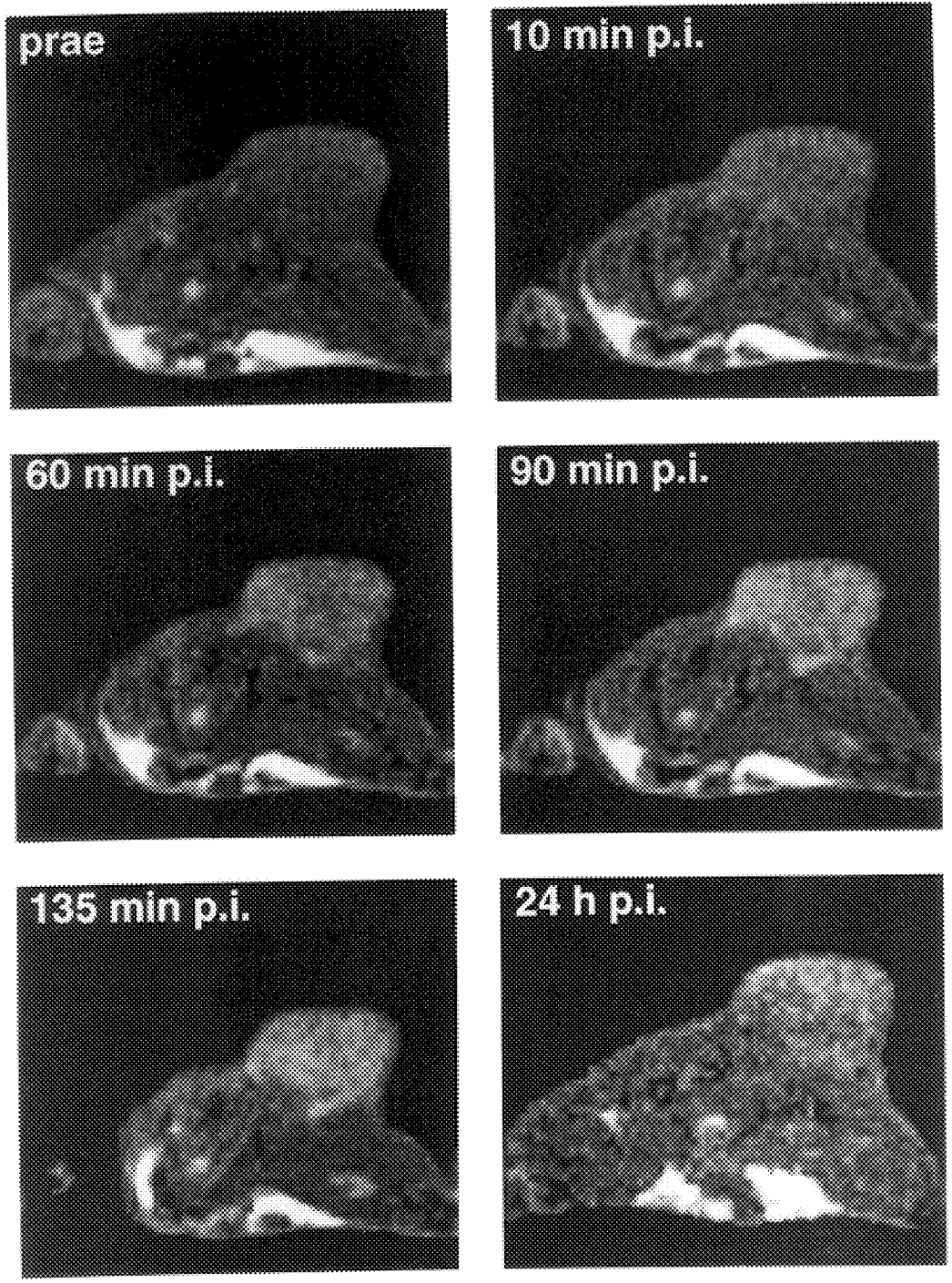
FIG. 33: Transversal T1-weighted spin echo dynamics study (TR: 300 ms, TE: 15 ms) of the tumoral signal behavior after bolus injection of nanoparticles according to Example D2 (200 µmol Fe/kg)

FIG. 33: Transversal T1-weighted spin echo dynamics study (TR: 300 ms, TE: 15 ms) of the tumoral signal behavior after bolus injection of nanoparticles according to Example D2 (200 μmol Fe/kg). The tomograms show a slow and time-dependent increase in signal enhancement (accumulation) in the tumor with increasingly clear demarcation of spatial requirement.

Figure 34:
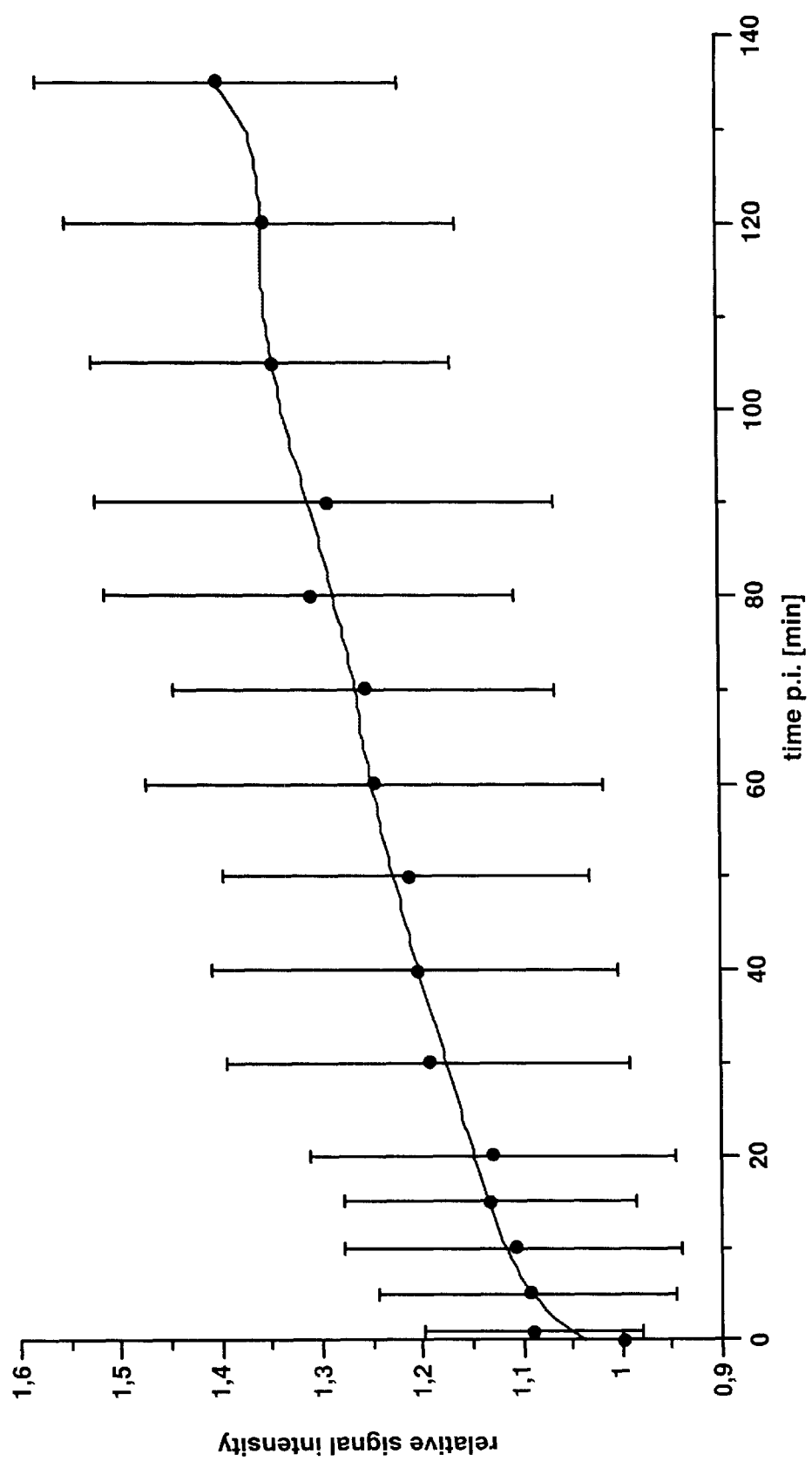
FIG. 34: Curve of relative signal intensity (accumulation) in the tumor.

FIG. 34: Curve of relative signal intensity (accumulation) in the tumor. The time history of the signal (enhancement) for a dose of 200 μmol/kg body wt illustrates the strong enhancement that increases over time (increasing accumulation) in the tumor (SE 2000/15).

Figure 35:
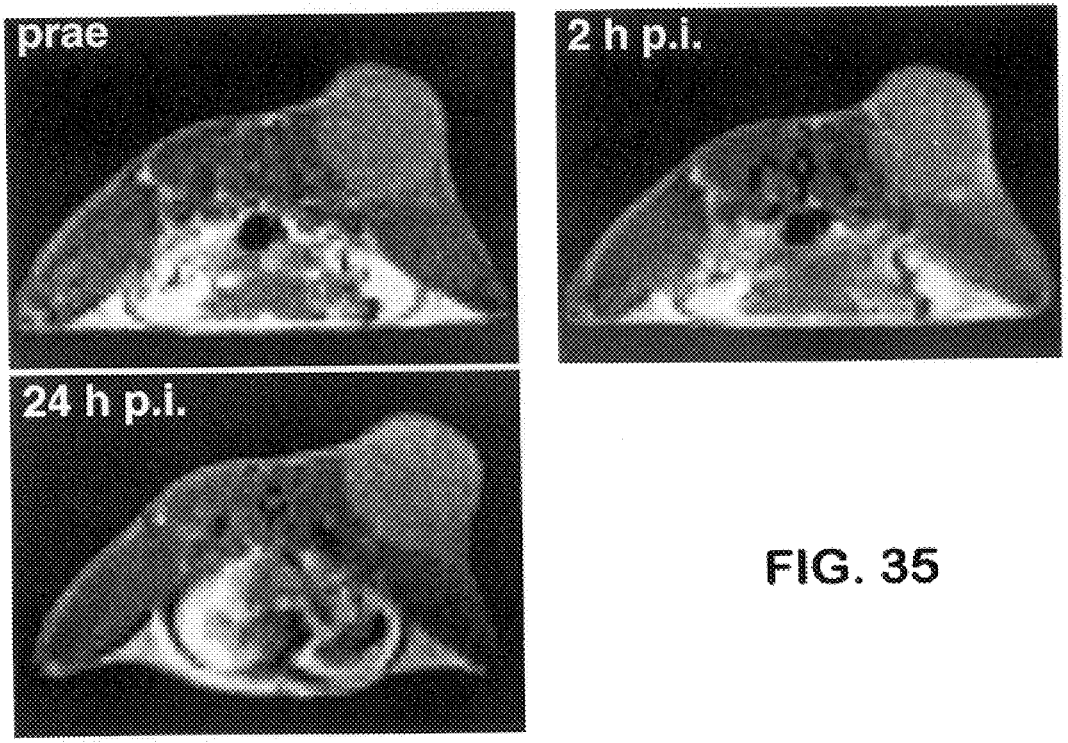
FIG. 35: Time-dependent transversal proton-density weighted (SE 2000/15) tomograms after application of the nanoparticles according to Example D2 (200 µmol Fe/kg).

FIG. 35: Time-dependent transversal proton-density-weighted (SE 2000/15) tomograms after application of the nanoparticles according to Example D2 (200 μmol Fe/kg).

Increasing accumulation of the nanoparticles in the tumor in conjunction with a linear increase in signal enhancement over time were found in the T1-weighted and proton-density-weighted spin echo sequence (FIGS. 33; 35). 35 to 40% enhancement were observed until 135 min. after injection, which permits a clear distinction of the tumor from the healthy tissue and confirms the accumulation of nanoparticles. Unlike the observations made here, it was found in angiographic studies that an enhancement in the tumor caused only by perfusion will have disappeared completely after a maximum of 30 min. (p.i.).

What is claimed is:

1. A method for diagnosing atherosclerosis comprising MR imaging of a patient having been administered nanoparticles comprising an iron-containing cores a primary synthesis polymer coat and a targeting polymer secondary coat.

2. A method for diagnosing atherosclerosis comprising MR imaging of a patient having been administered a plurality of nanoparticles having an iron-containing core of magnetite or maghemite, a primary coat of a synthesis polymer of dextrans or dextran derivatives and a secondary coat of a targeting polymer non-covalently bonded to the synthesis polymer, wherein the targeting polymer is not exposed to synthesis conditions.

3. The method of claim 2, wherein the iron-containing core comprises organic salts.

4. The method of claim 3, wherein the organic salts are iron (II) gluconate, iron (III) citrate, or mixtures thereof.

5. The method of claim 2, wherein the targeting polymer comprises a peptide.

6. The method of claim 2, wherein the targeting polymer comprises an endohelin-receptor-specific-heptapeptide.

7. The method of claim 6, wherein the endothelinreceptor-specific-heptapeptide includes an amino acid sequence CHLDIIW.

8. The method of claim 2, said nanoparticles further comprising one or more additional components bonded to the secondary coat, said additional components being adsorption mediators/enhancers, pharmaceutical adjuvants, or pharmaceuticals.

9. The method according to claim 2, wherein the iron-containing core comprises 0.1 to 25% weight of non-iron metallic ions.

10. The method according to claim 9, wherein the non-iron metallic ions are paramagnetic ions or diamagnetic ions.

11. The method according to claim 2, wherein the iron-containing core and the synthesis polymer coating have a diameter less than 100 nanometers.

12. The method according to claim 2, wherein the nanoparticles have a hydrodynamic diameter of less than 10 times the diameter of the iron-containing core.

13. The method according to claim 9 wherein the targeting polymer has a weight that is between 0.5 times to 50 times the weight of the non-iron metallic ions.

14. The method according to claim 2, wherein the nanoparticles further comprise an optional absorption permitting peptide substance which is RRTVKHHVN, RRSRHH or RSKRGR.

15. The method according to claim 2, wherein the nanoparticles further comprise a pharmaceutically active compound.

16. The method according to claim 2, wherein the targeting polymer is dextran, a dextran derivative, laminarin, transferrin, or endothelin-receptor-specific heptapeptide.

* * * * *